(12) United States Patent
Park et al.

(10) Patent No.: US 10,418,566 B2
(45) Date of Patent: Sep. 17, 2019

(54) CONDENSED CYCLIC COMPOUND AND ORGANIC LIGHT-EMITTING DEVICE COMPRISING THE SAME

(71) Applicant: SAMSUNG DISPLAY CO., LTD., Yongin-si, Gyeonggi-do (KR)

(72) Inventors: Junha Park, Yongin-si (KR); Youngkook Kim, Yongin-si (KR); Munki Sim, Yongin-si (KR); Eunyoung Lee, Yongin-si (KR); Eunjae Jeong, Yongin-si (KR); Seokhwan Hwang, Yongin-si (KR); Donghyun Kim, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 182 days.

(21) Appl. No.: 14/938,770

(22) Filed: Nov. 11, 2015

(65) Prior Publication Data

US 2016/0285011 A1  Sep. 29, 2016

(30) Foreign Application Priority Data

Mar. 23, 2015  (KR) .................. 10-2015-0040211

(51) Int. Cl.
*H01L 51/00* (2006.01)
*C07F 9/6558* (2006.01)
(Continued)

(52) U.S. Cl.
CPC ........ *H01L 51/0073* (2013.01); *C07D 307/77* (2013.01); *C07F 9/65517* (2013.01);
(Continued)

(58) Field of Classification Search
None
See application file for complete search history.

(56) References Cited

U.S. PATENT DOCUMENTS

| | | |
|---|---|---|
| 5,645,948 A | 7/1997 | Shi et al. |
| 9,899,611 B2 | 2/2018 | Park et al. |
| | (Continued) | |

FOREIGN PATENT DOCUMENTS

| | | |
|---|---|---|
| CN | 103396386 A | 11/2013 |
| CN | 107251260 A | 10/2017 |
| | (Continued) | |

OTHER PUBLICATIONS

Cho et al ("Asymmetric Synthesis of Axially Chiral Biaryls by Nickel-Catalyzed Grignard Cross-Coupling of Dibenzothiophenes", Journal of Organic Chemistry (2004), vol. 69(11), pp. 3811-3823.*
(Continued)

*Primary Examiner* — Sin J Lee
(74) *Attorney, Agent, or Firm* — Lewis Roca Rothgerber Christie LLP

(57) ABSTRACT

An organic light-emitting device including a first electrode as an anode; a second electrode as a cathode and facing the first electrode; and an organic layer between the first electrode and the second electrode, the organic layer including an emission layer, a hole transport region between the first electrode and the emission layer, and an electron transport region between the emission layer and the second electrode, where at least one selected from the emission layer and the electron transport region includes at least one selected from condensed cyclic compounds represented by Formula 1:

$$A_2\text{-}(A_1)_{n1}. \qquad \text{Formula 1}$$

24 Claims, 4 Drawing Sheets

(51) Int. Cl.
*C07F 9/655* (2006.01)
*C07D 307/77* (2006.01)
*C09K 11/02* (2006.01)
*H01L 51/50* (2006.01)

(52) U.S. Cl.
CPC ........ *C07F 9/65586* (2013.01); *C09K 11/025* (2013.01); *H01L 51/0094* (2013.01); *H01L 51/006* (2013.01); *H01L 51/0058* (2013.01); *H01L 51/0061* (2013.01); *H01L 51/0085* (2013.01); *H01L 51/5012* (2013.01); *H01L 51/5072* (2013.01)

(56) References Cited

U.S. PATENT DOCUMENTS

| | | | |
|---|---|---|---|
| 2002/0055014 | A1 | 5/2002 | Okada et al. |
| 2004/0053069 | A1 | 3/2004 | Sotoyama et al. |
| 2004/0137270 | A1 | 7/2004 | Seo et al. |
| 2011/0147716 | A1 | 6/2011 | Kondakova et al. |
| 2012/0074392 | A1 | 3/2012 | Huang et al. |
| 2012/0326137 | A1 | 12/2012 | Song et al. |
| 2013/0200341 | A1 | 8/2013 | Fadhel et al. |
| 2013/0306958 | A1 | 11/2013 | Ito et al. |
| 2014/0034915 | A1 | 2/2014 | Lee et al. |
| 2014/0103325 | A1 | 4/2014 | Shin et al. |
| 2014/0183500 | A1 | 7/2014 | Ikeda et al. |
| 2015/0014673 | A1 | 1/2015 | Takeya et al. |
| 2015/0236273 | A1 | 8/2015 | Jang et al. |
| 2015/0243908 | A1 | 8/2015 | Lee et al. |
| 2016/0285011 | A1 | 9/2016 | Park et al. |
| 2017/0040549 | A1 | 2/2017 | Jeong et al. |
| 2017/0062736 | A1 | 3/2017 | Parham et al. |
| 2017/0104167 | A1* | 4/2017 | Sim ................. C09K 11/025 |
| 2017/0125689 | A1 | 5/2017 | Lee et al. |
| 2018/0076397 | A1 | 3/2018 | Frey et al. |
| 2018/0145263 | A1 | 5/2018 | Denker et al. |

FOREIGN PATENT DOCUMENTS

| | | | |
|---|---|---|---|
| JP | 10-17860 | A | 1/1998 |
| JP | 11-87067 | A | 3/1999 |
| JP | 2006-73581 | A | 3/2006 |
| JP | 4060669 | B2 | 3/2008 |
| JP | 2013-100239 | A | 5/2013 |
| JP | 2014-133713 | * | 7/2014 |
| KR | 10-0525408 | B1 | 11/2005 |
| KR | 10-2012-0138671 | A | 12/2012 |
| KR | 10-2013-0075982 | A | 7/2013 |
| KR | 10-2013-0119413 | A | 10/2013 |
| KR | 10-2014-0017400 | A | 2/2014 |
| KR | 10-2014-0032948 | A | 3/2014 |
| WO | WO 2013/125599 | A1 | 8/2013 |
| WO | WO-2014/018919 | A1 * | 1/2014 |
| WO | WO 2016/131918 | A1 * | 8/2016 |
| WO | WO-2017022751 | A1 * | 2/2017 ........... C07D 345/00 |

OTHER PUBLICATIONS

Derwent English abstract for JP 2014-133713 (2014).*
Machine-assisted English translation for JP 2014-133713 (2014) provided by JPO.*
Derwent English abstract for WO 2017/022751 A1. (Year: 2017).*
Partial English translation for WO 2017/022751 A1, provided by PTO. (Year: 2017).*
Adachi, C. et al., Confinement of charge carriers and molecular excitons within 5nmthick emitter layer in organic electroluminescent devices with a double heterostructure, AIP: Applied Physics Letters, 1990, pp. 531-533, vol. 57, No. 6, AIP Publishing LLC.
Johansson, N. et al., Solid-State Amplified Spontaneous Emission in Some Spiro-Type Molecules: A New Concept for the Design of Solid-State Lasing Molecules, Advanced Materials, 1998, pp. 1136-1141, vol. 10, No. 14, Wiley-VCH Verlag GmbH, Weinheim, Germany.
Sakamoto, Y. et al., Synthesis, Characterization, and Electron-Transport Property of Perfluorinated Phenylene Dendrimers, Journal of the American Chemical Society, 2000, pp. 1832-1833, vol. 122, American Chemical Society, U.S.
Tang, C.W. et al., Organic Electroluminescent diodes, AIP: Applied Physics Letters, 1987, pp. 913-915, vol. 51, No. 12, AIP Publishing LLC.
Tao, Y.T. et al., Sharp green electroluminescence from 1H-pyrazolo[3,4-b]quinoline-based light-emitting diodes, AIP: Applied Physics Letters, 2000, pp. 1575-1577, vol. 77, No. 11, AIP Publishing LLC.
Yamaguchi, S. et al., Diphenylamino-Substituted 2,5-Diarylsiloles for Single-Layer Organic Electroluminescent Devices, Chemistry Letters, 2001, pp. 98-99, The Chemical Society of Japan.
U.S. Office Action dated May 31, 2018, issued in U.S. Appl. No. 15/162,450 (17 pages).
Machine translation of KR-20130075982 A.
U.S. Final Office Action dated Sep. 27, 2018, issued in U.S. Appl. No. 15/162,450 (26 pages).
U.S. Office Action dated Mar. 29, 2019, issued in U.S. Appl. No. 15/162,450 (21 pages).
U.S. Advisory Action dated Dec. 13, 2018, issued in U.S. Appl. No. 15/162,450 (4 pages).

* cited by examiner

| 190 |
|-----|
| 150 |
| 110 |

| |
|---|
| 190 |
| 150 |
| 110 |
| 210 |

| 220 |
|---|
| 190 |
| 150 |
| 110 |

| 220 |
|-----|
| 190 |
| 150 |
| 110 |
| 210 |

CONDENSED CYCLIC COMPOUND AND ORGANIC LIGHT-EMITTING DEVICE COMPRISING THE SAME

CROSS-REFERENCE TO RELATED APPLICATION

This application claims priority to and the benefit of Korean Patent Application No. 10-2015-0040211, filed on Mar. 23, 2015, in the Korean Intellectual Property Office, the entire content of which is incorporated herein by reference.

BACKGROUND

1. Field

One or more aspects of embodiments of the present disclosure relate to a condensed cyclic compound and an organic light-emitting device including the same.

2. Description of the Related Art

Organic light-emitting devices (OLEDs) are self-emitting devices that have advantages such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially positioned in this order on a substrate. Holes injected from the first electrode move to the emission layer via the hole transport region, while electrons injected from the second electrode move to the emission layer via the electron transport region. Carriers such as holes and electrons then recombine in the emission layer to generate excitons. When the excitons drop from an excited state to a ground state, light is emitted.

SUMMARY

One or more aspects of embodiments of the present disclosure are directed to a novel condensed cyclic compound and an organic light-emitting device including the same.

Additional aspects will be set forth in part in the description which follows and, in part, will be apparent from the description, or may be learned by practice of the presented embodiments.

According to one or more embodiments of the present disclosure, a condensed cyclic compound is represented by Formula 1:

$$A_2\text{-}(A_1)_{n1}, \quad \text{Formula 1}$$

wherein, in Formula 1, $A_2$ may be selected from groups represented by Formulae 2A to 2E;

$A_1$ may be selected from groups represented by Formulae 2-1 to 2-4; and n1 may be an integer selected from 1 to 5, wherein, when n1 is 2 or greater, at least two $A_1$s may be the same as or different from each other:

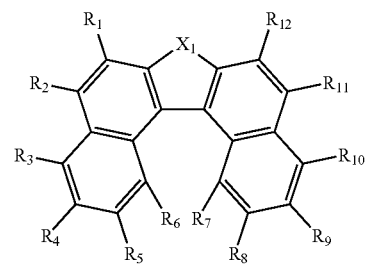

Formula 2A

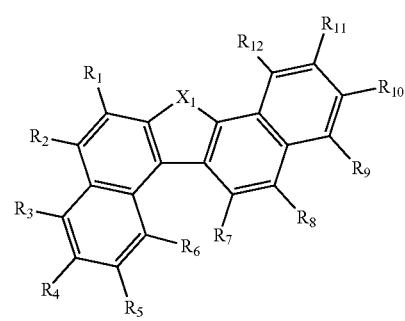

Formula 2B

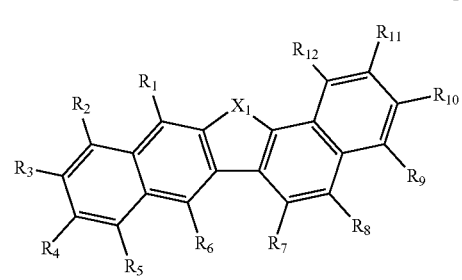

Formula 2C

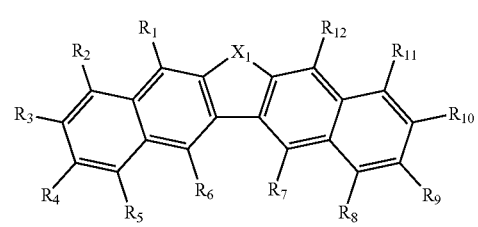

Formula 2D

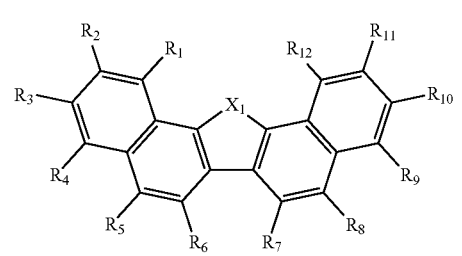

Formula 2E

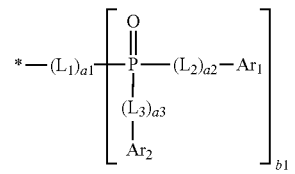

Formula 2-1

-continued

Formula 2-2

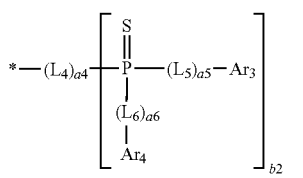

Formula 2-3

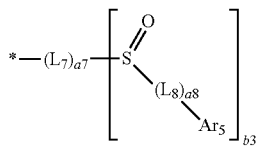

Formula 2-4

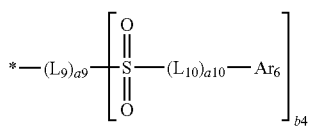

Formula 2-11

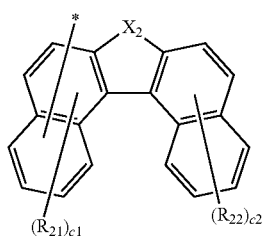

Formula 2-12

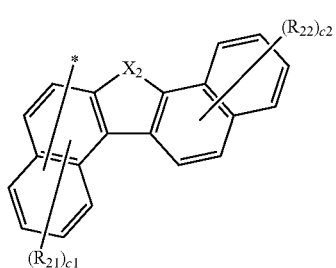

Formula 2-13

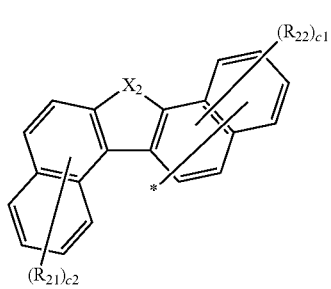

Formula 2-14

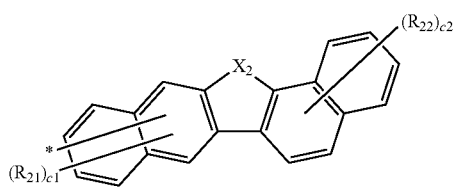

Formula 2-15

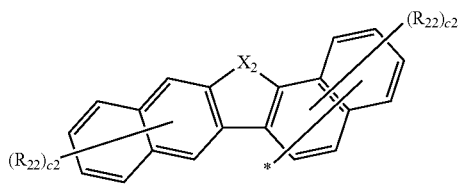

Formula 2-16

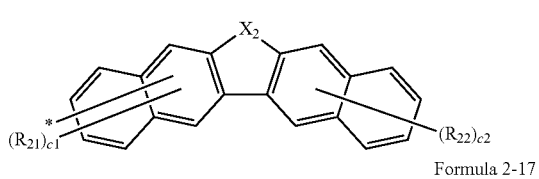

Formula 2-17

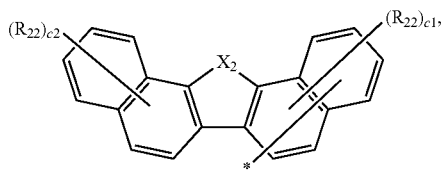

wherein, $X_1$ and $X_2$ in Formulae 2A to 2E and Formulae 2-11 to 2-17 may be each independently O or S;

$R_1$ to $R_{12}$ in Formulae 2A to 2E may be each independently selected from a binding site to $A_1$ in Formula 1, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group (e.g., a substituted or unsubstituted monovalent non-aromatic condensed polycyclic group), a substituted or unsubstituted monovalent non-aromatic condensed heteropolycyclic group (e.g., substituted or unsubstituted monovalent non-aromatic condensed heteropolycyclic group), —N($Q_1$)($Q_2$), —Si($Q_3$)($Q_4$)($Q_5$), and —B($Q_6$)($Q_7$);

$R_1$ to $R_{12}$ in Formulae 2A to 2E may each independently be a binding site to $A_1$ in Formula 1, where at least one selected from $R_1$ to $R_{12}$ is a binding site to $A_1$ and the number of binding sites is equal to n1 in Formula 1;

$L_1$ to $L_{10}$ in Formulae 2-1 to 2-4 may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a10 in Formulae 2-1 to 2-4 may be each independently an integer selected from 0 to 5;

$Ar_1$ to $Ar_6$ in Formulae 2-1 to 2-4 may each independently be selected from groups represented by Formulae 2-11 to 2-17, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b1 to b4 in Formulae 2-1 to 2-4 may be each independently an integer selected from 1 to 5;

$R_{21}$ and $R_{22}$ in Formulae 2-11 to 2-17 may each independently be hydrogen, deuterium, —F, —Cl, —Br, —I, a hydroxyl group, a cyano group, a nitro group, an amino group, an amidino group, a hydrazine group, a hydrazone group, a carboxylic group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

c1 in Formulae 2-11 to 2-17 may be an integer selected from 0 to 5; and c2 in Formulae 2-11 to 2-17 may be an integer selected from 0 to 6, wherein at least one selected from substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group (e.g., aryloxy), $C_6$-$C_{60}$ arylthio group (e.g., arylthio), $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more embodiments of the present disclosure, an organic light-emitting device includes: a first electrode; a second electrode facing the first electrode; and an organic layer between the first electrode and the second electrode, the organic layer including an emission layer, wherein the organic layer includes at least one condensed cyclic compound as described above.

BRIEF DESCRIPTION OF THE DRAWINGS

These and/or other aspects will become apparent and more readily appreciated from the following description of the embodiments, taken in conjunction with the accompanying drawings in which:

FIGS. 1 to 4 are schematic views of organic light-emitting devices according to embodiments of the present disclosure.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one selected from" and "one selected from," when preceding a list of elements, modify the entire list of elements and do not modify the individual elements of the list. Further, the use of "may" when describing embodiments of the present invention refers to "one or more embodiments of the present invention."

According to an embodiment of the present disclosure, there is provided a condensed cyclic compound represented by Formula 1:

$$A_2\text{-}(A_1)_{n1}.$$ Formula 1

In Formula 1, $A_2$ may be selected from groups represented by Formulae 2A to 2E;

$A_1$ may be selected from groups represented by Formulae 2-1 to 2-4; and n1 may be an integer selected from 1 to 5, and when n1 is 2 or greater, at least two $A_1$s may be the same as or different from each other.

Formula 2A

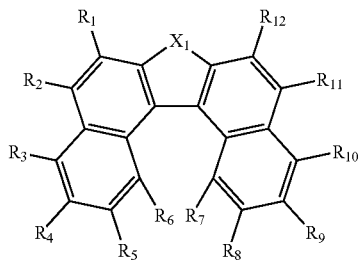

Formula 2B

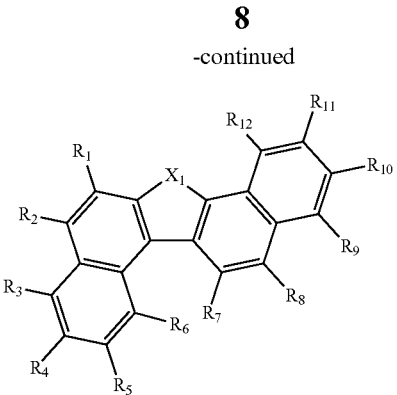

Formula 2C

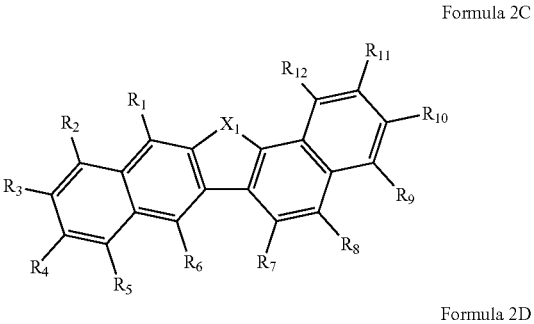

Formula 2D

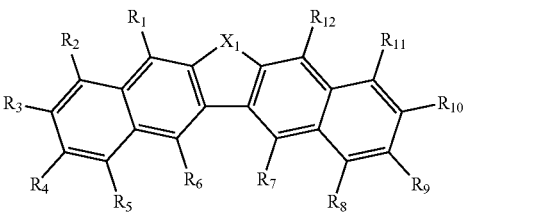

Formula 2E

Formula 2-1

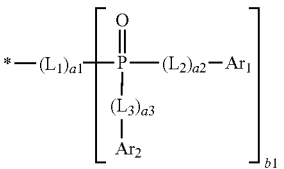

Formula 2-2

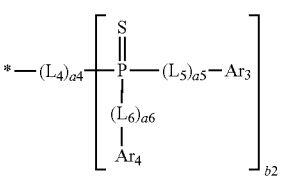

Formula 2-3

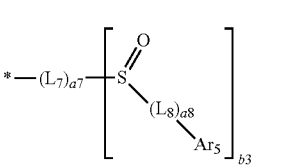

-continued

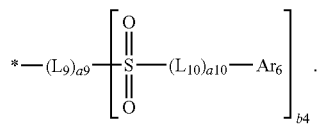

Formula 2-4

In Formulae 2A to 2E, $X_1$ may be oxygen (O) or sulfur (S).

In some embodiments, $X_1$ in Formulae 2A to 2E may be 0.

In Formulae 2A to 2E, $R_1$ to $R_{12}$ may be each independently selected from a binding site to $A_1$ in Formula 1 (e.g., a chemical bond such as a single bond coupled to $A_1$ in Formula 1), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, where $Q_1$ to $Q_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, in Formulae 2A to 2E, $R_1$ to $R_{12}$ may be each independently selected from:

a binding site to $A_1$ in Formula 1 (e.g., a chemical bond such as a single bond coupled to $A_1$ in Formula 1);

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$); and —Si($Q_3$)($Q_4$)($Q_5$), where $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, in Formulae 2A to 2E, $R_1$ to $R_{12}$ may be each independently selected from:

a binding site to $A_1$ in Formula 1 (e.g., a chemical bond such as a single bond coupled to $A_1$ in Formula 1);

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{33}$)($Q_{34}$)($Q_{35}$); and —Si($Q_3$)($Q_4$)($Q_5$), where $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In some other embodiments, in Formulae 2A to 2E, $R_1$ to $R_{12}$ may be each independently selected from a binding site to $A_1$ in Formula 1 (e.g., a chemical bond such as a single bond coupled to $A_1$ in Formula 1), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75 (for example, groups represented by Formulae 6-1 to 6-43 and/or Formulae 10-1 to 10-117), and —Si($Q_3$)($Q_4$)($Q_5$), where $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

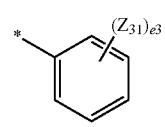

Formula 5-1

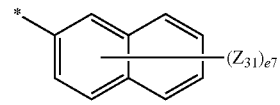

Formula 5-2

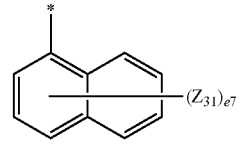

Formula 5-3

-continued
Formula 5-4
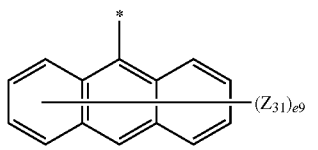
Formula 5-5
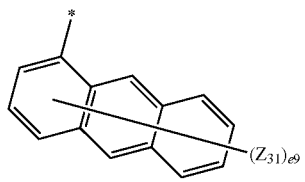
Formula 5-6
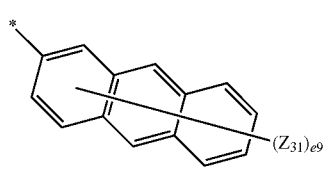
Formula 5-7
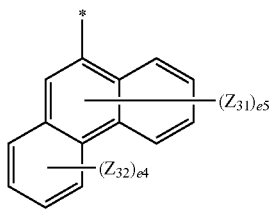
Formula 5-8
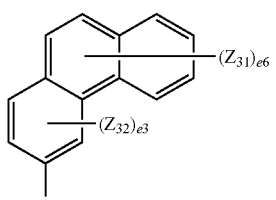
Formula 5-9
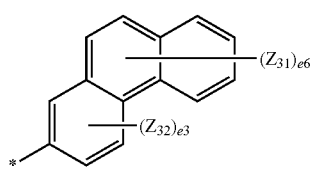
Formula 5-10
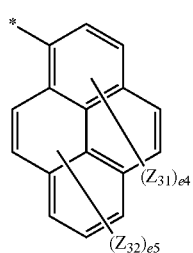
Formula 5-11
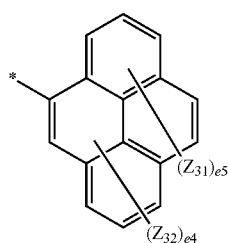
-continued
Formula 5-12
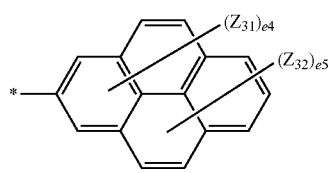
Formula 5-13
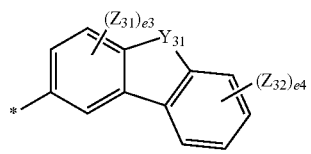
Formula 5-14
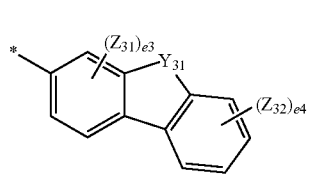
Formula 5-15
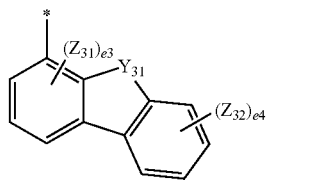
Formula 5-16
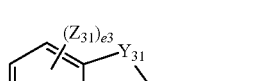
Formula 5-17
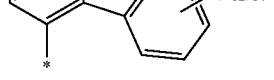
Formula 5-18
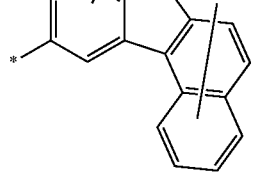
Formula 5-19
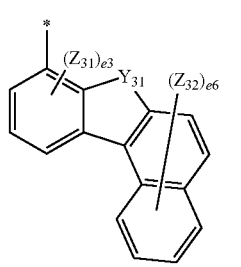

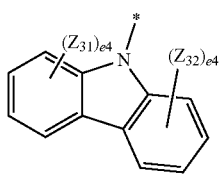
Formula 5-20
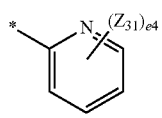
Formula 5-21
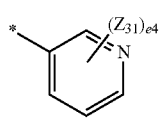
Formula 5-22
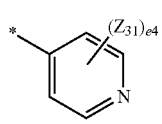
Formula 5-23
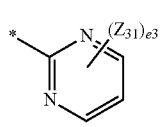
Formula 5-24
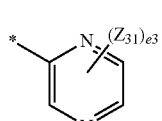
Formula 5-25
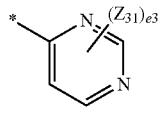
Formula 5-26
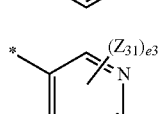
Formula 5-27
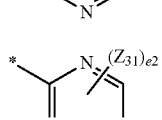
Formula 5-28
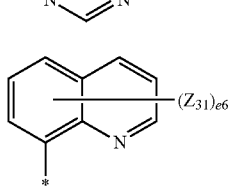
Formula 5-29
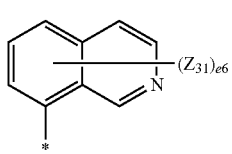
Formula 5-30
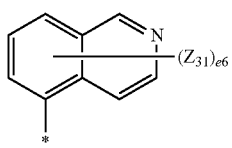
Formula 5-31
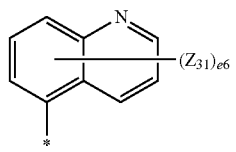
Formula 5-32
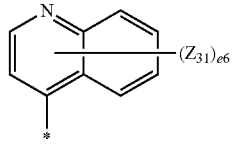
Formula 5-33
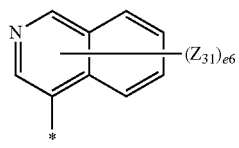
Formula 5-34
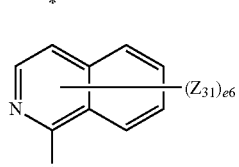
Formula 5-35
Formula 5-36
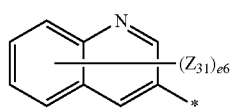
Formula 5-37
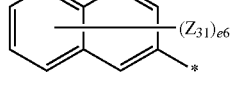
Formula 5-38
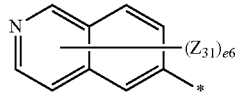
Formula 5-39
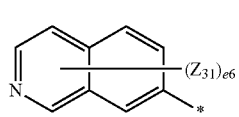
Formula 5-40
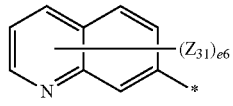
Formula 5-41
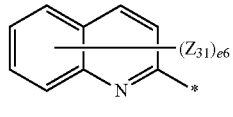
Formula 5-42
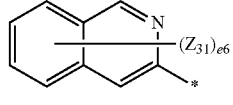
Formula 5-43
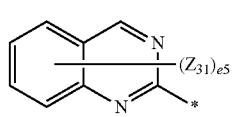

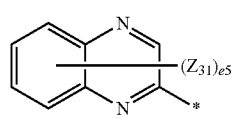 Formula 5-44
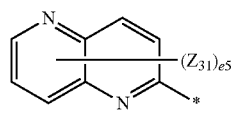 Formula 5-45
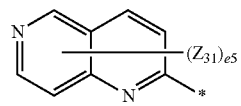 Formula 5-46
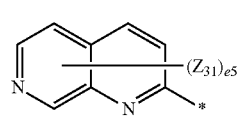 Formula 5-47
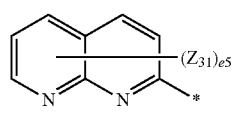 Formula 5-48
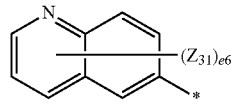 Formula 5-49
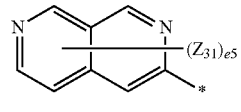 Formula 5-50
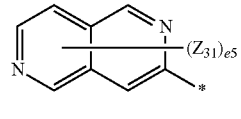 Formula 5-51
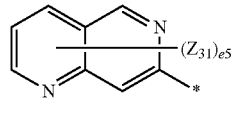 Formula 5-52
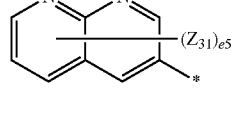 Formula 5-53
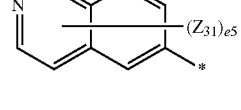 Formula 5-54
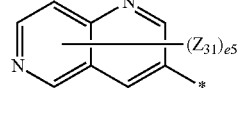 Formula 5-55
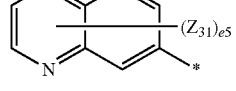 Formula 5-56
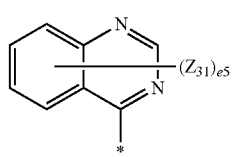 Formula 5-57
Formula 5-58
Formula 5-59
Formula 5-60
Formula 5-61
Formula 5-62
Formula 5-63
Formula 5-64
Formula 5-65
Formula 5-66

-continued

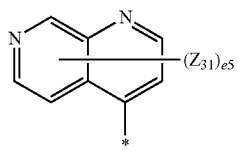
Formula 5-67

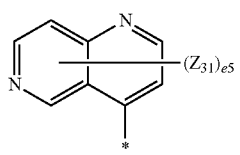
Formula 5-68

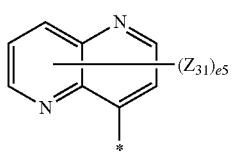
Formula 5-69

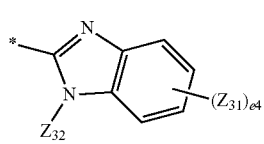
Formula 5-70

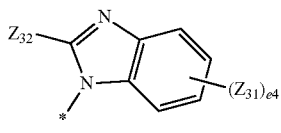
Formula 5-71

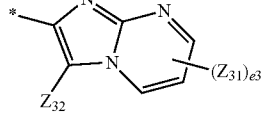
Formula 5-72

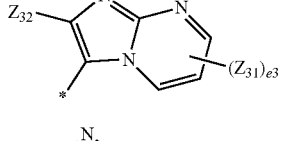
Formula 5-73

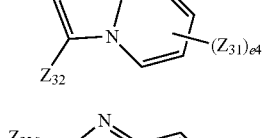
Formula 5-74

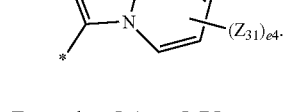
Formula 5-75

In Formulae 5-1 to 5-75, $Y_{31}$ may be selected from O, S, $C(Z_{33})(Z_{34})$, $N(Z_{35})$, and $Si(Z_{36})(Z_{37})$, $Z_{31}$ to $Z_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, and a naphthyl group, e2 may be an integer selected from 1 and 2,
e3 may be an integer selected from 1 to 3,
e4 may be an integer selected from 1 to 4,
e5 may be an integer selected from 1 to 5,
e6 may be an integer selected from 1 to 6,
e7 may be an integer selected from 1 to 7,
e8 may be an integer selected from 1 to 8,
e9 may be an integer selected from 1 to 9, and
* may be a binding site with an adjacent atom.

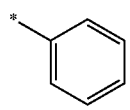
Formula 6-1

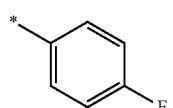
Formula 6-2

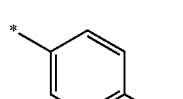
Formula 6-3

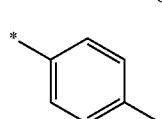
Formula 6-4

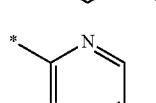
Formula 6-5

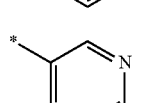
Formula 6-6

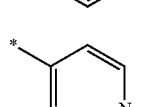
Formula 6-7

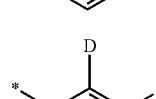
Formula 6-8

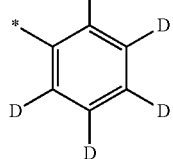
Formula 6-9

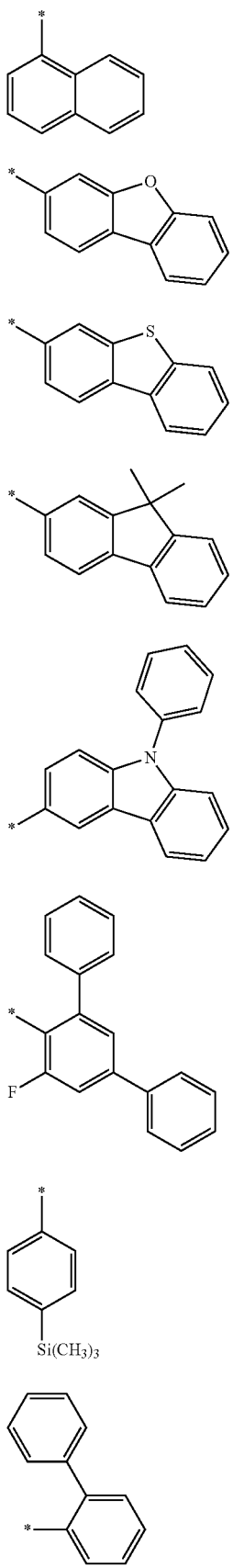
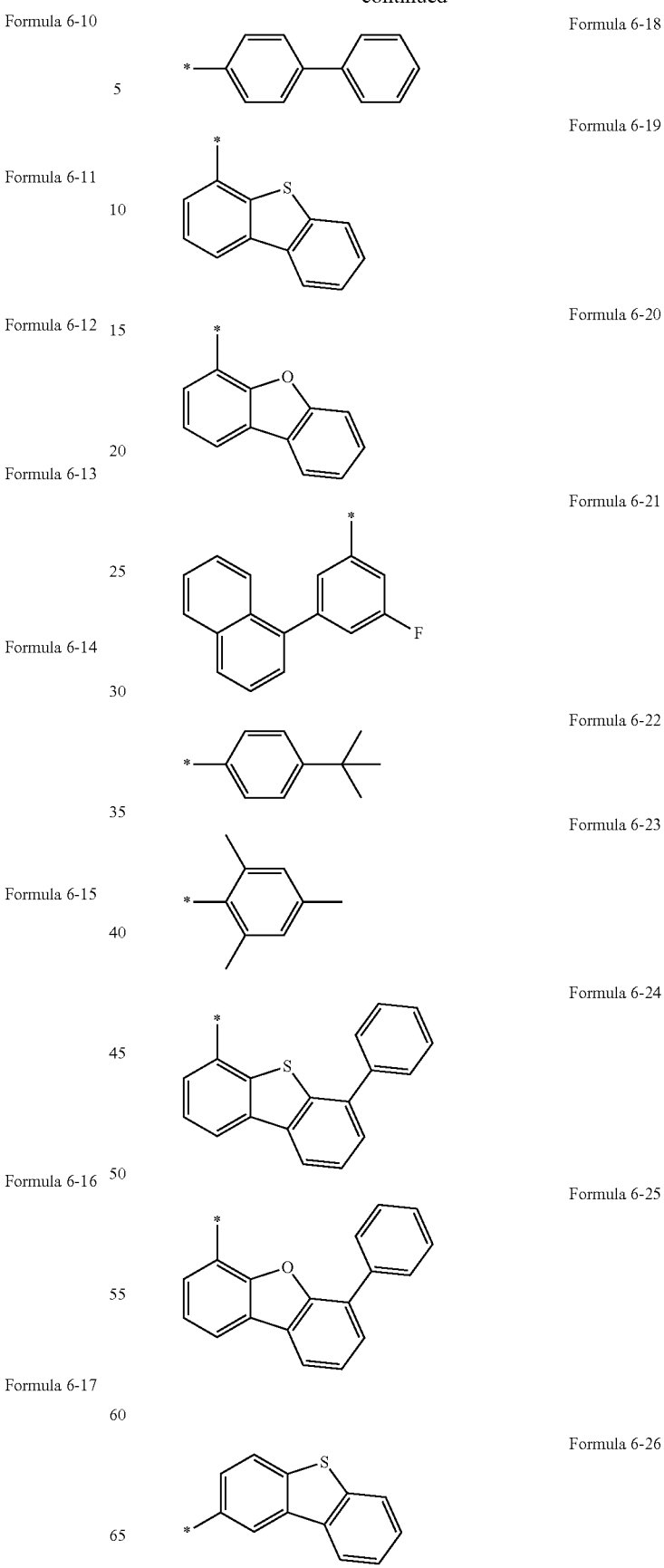

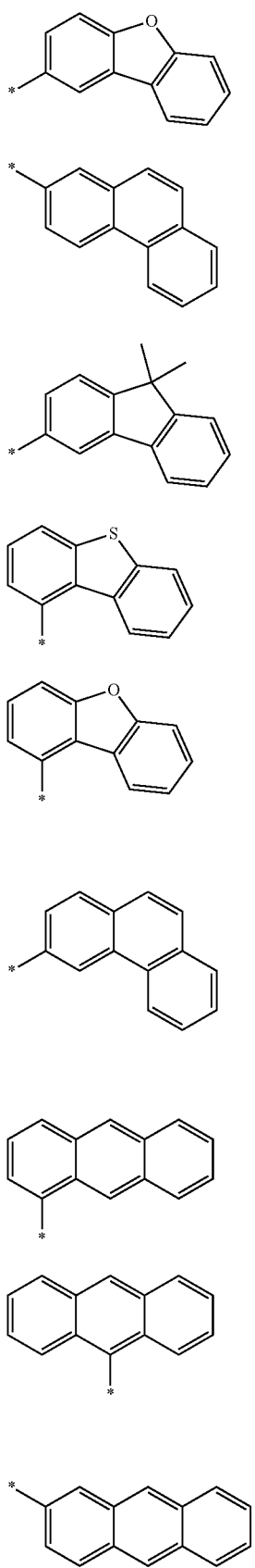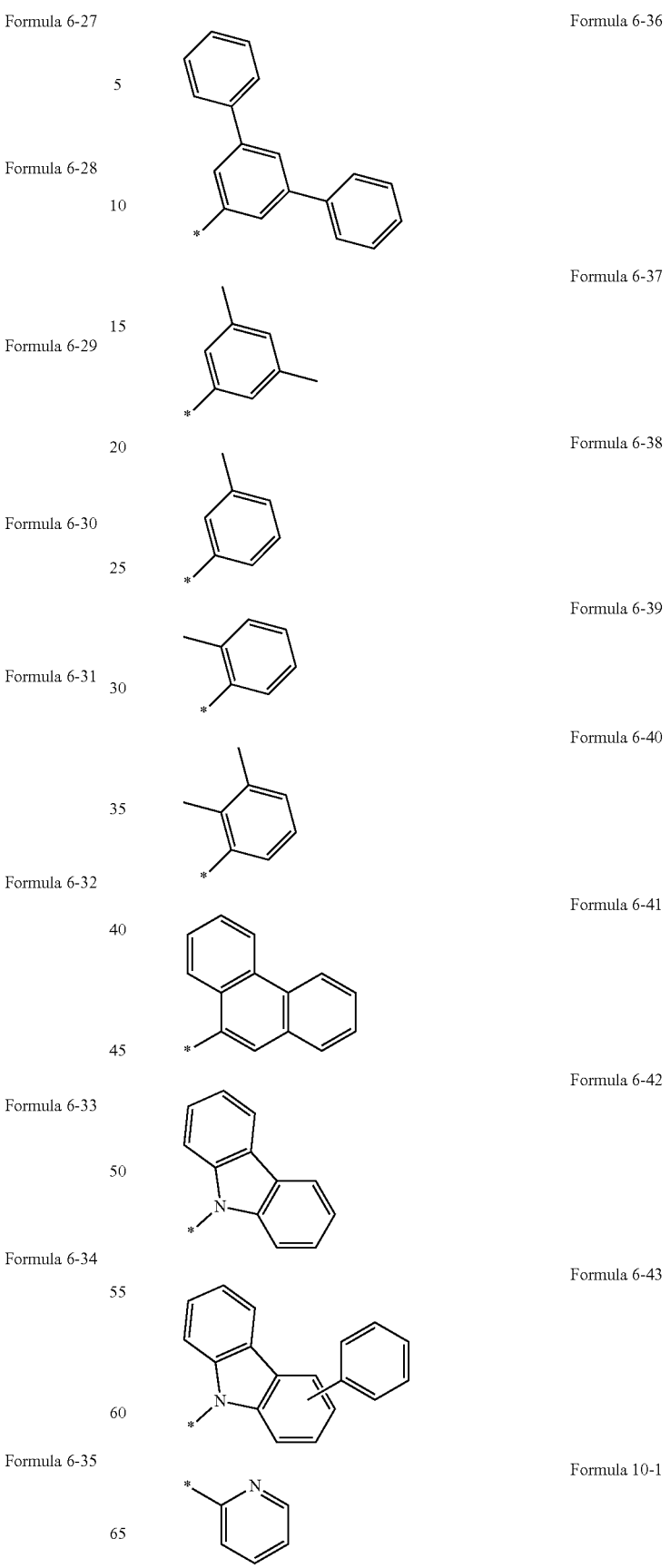

Formula 10-2

Formula 10-3

Formula 10-4

Formula 10-5

Formula 10-6

Formula 10-7

Formula 10-8

Formula 10-9

Formula 10-10

Formula 10-11

Formula 10-12

Formula 10-13

Formula 10-14

Formula 10-15

Formula 10-16

Formula 10-17

Formula 10-18

Formula 10-19

Formula 10-20

Formula 10-21

Formula 10-22
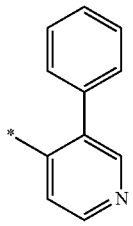
Formula 10-23
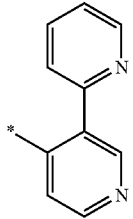
Formula 10-24
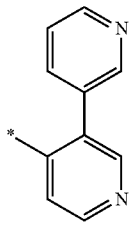
Formula 10-25
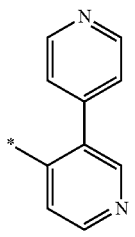
Formula 10-26
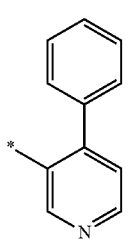
Formula 10-27
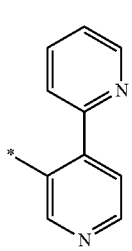
Formula 10-28
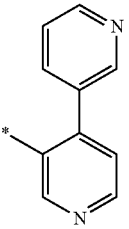
Formula 10-29
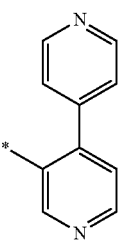
Formula 10-30
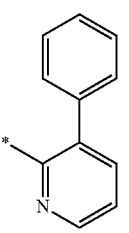
Formula 10-31
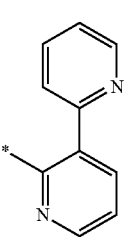
Formula 10-32
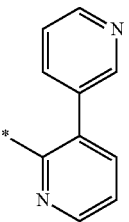
Formula 10-33
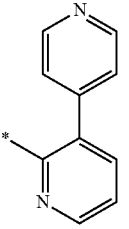

Formula 10-34
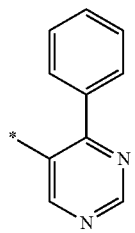
Formula 10-35
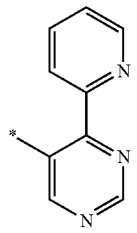
Formula 10-36
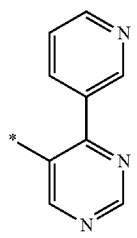
Formula 10-37
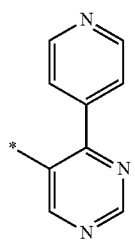
Formula 10-38
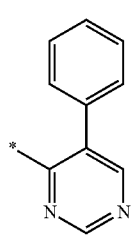
Formula 10-39
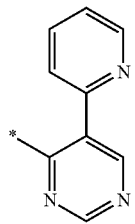
Formula 10-40
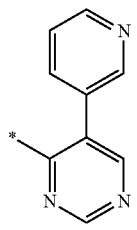
Formula 10-41
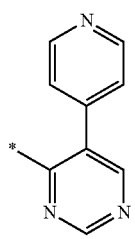
Formula 10-42
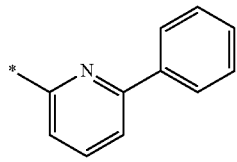
Formula 10-43
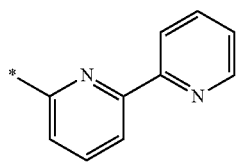
Formula 10-44
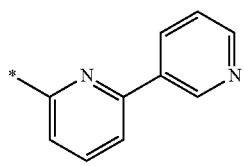
Formula 10-45
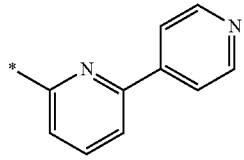
Formula 10-46
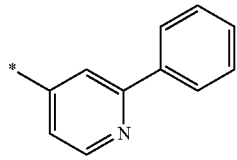
Formula 10-47
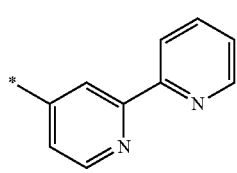

Formula 10-48
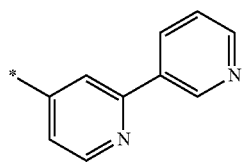
Formula 10-49
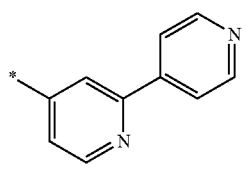
Formula 10-50
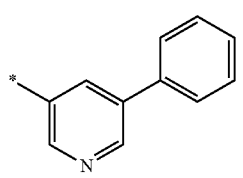
Formula 10-51
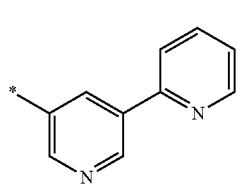
Formula 10-52
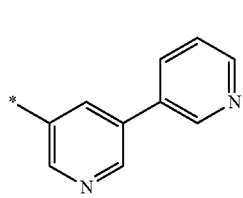
Formula 10-53
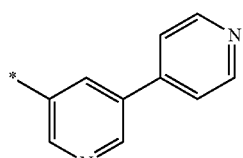
Formula 10-54
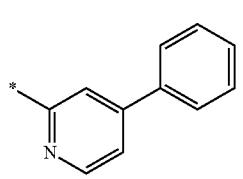
Formula 10-55
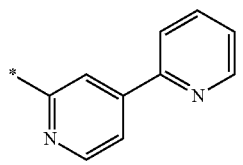
Formula 10-56
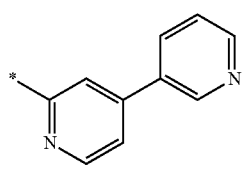
Formula 10-57
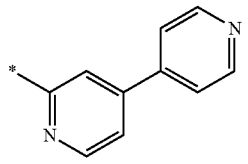
Formula 10-58
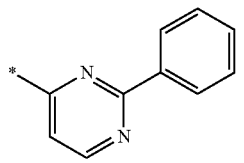
Formula 10-59
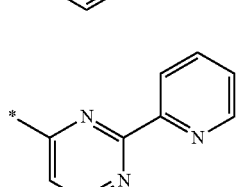
Formula 10-60
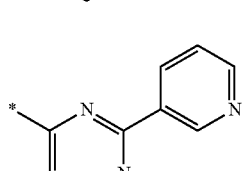
Formula 10-61
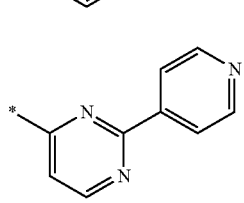
Formula 10-62
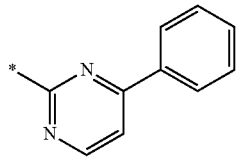
Formula 10-63
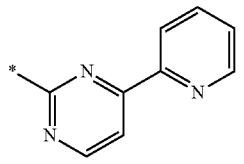
Formula 10-64
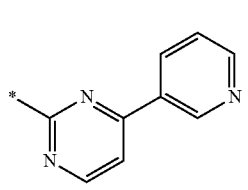
Formula 10-65
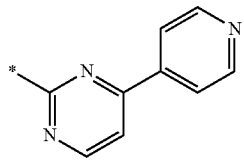

Formula 10-66
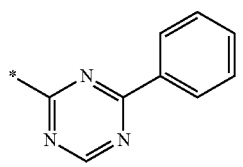
Formula 10-67
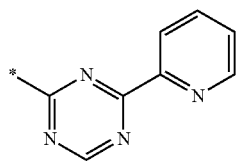
Formula 10-68
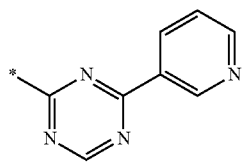
Formula 10-69
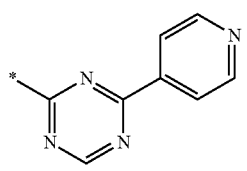
Formula 10-70
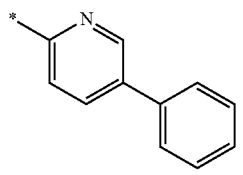
Formula 10-71
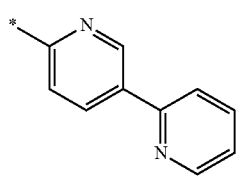
Formula 10-72
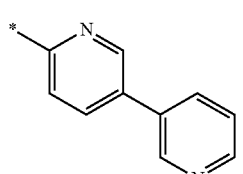
Formula 10-73
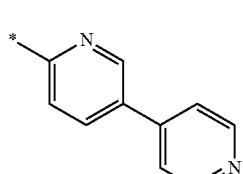
Formula 10-74
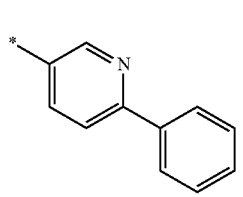
Formula 10-75
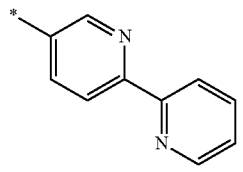
Formula 10-76
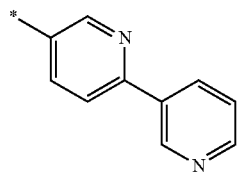
Formula 10-77
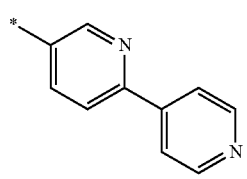
Formula 10-78
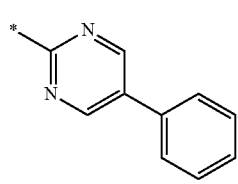
Formula 10-79
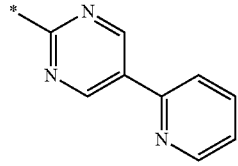
Formula 10-80
Formula 10-81
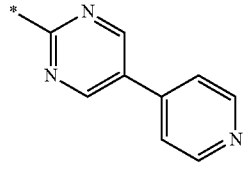
Formula 10-82
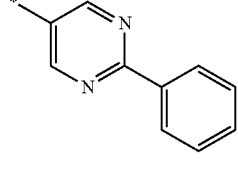
Formula 10-83
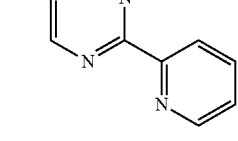

Formula 10-84
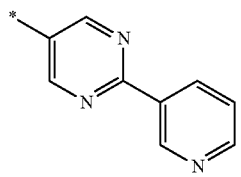
Formula 10-85
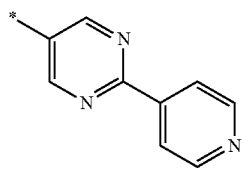
Formula 10-86
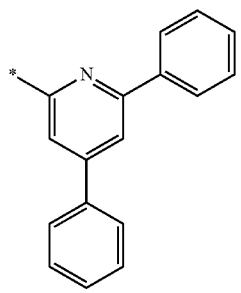
Formula 10-87
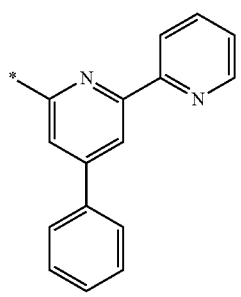
Formula 10-88
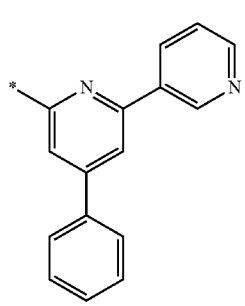
Formula 10-89
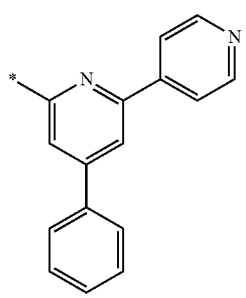
Formula 10-90
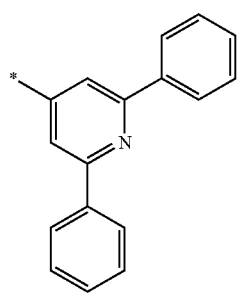
Formula 10-91
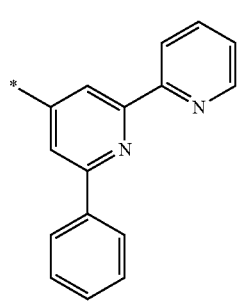
Formula 10-92
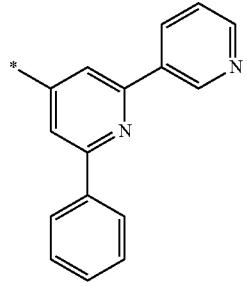
Formula 10-93
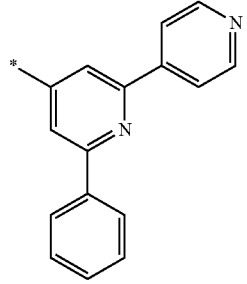
Formula 10-94
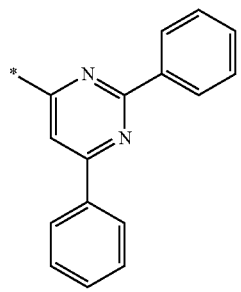

Formula 10-95
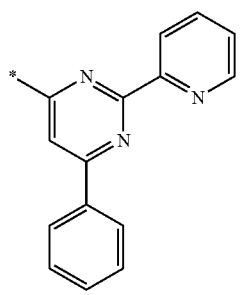
Formula 10-96
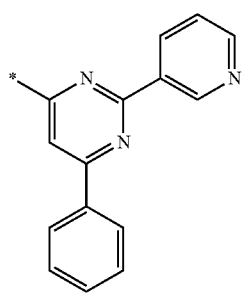
Formula 10-97
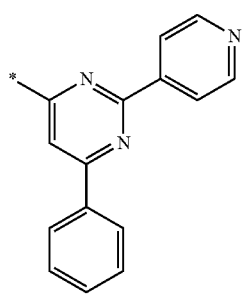
Formula 10-98
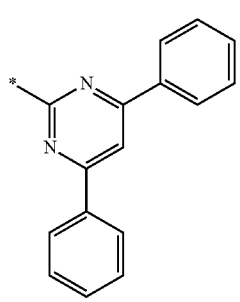
Formula 10-99
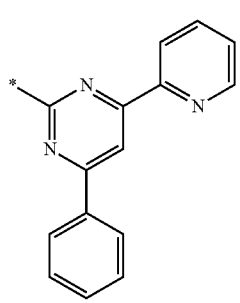
Formula 10-100

Formula 10-101
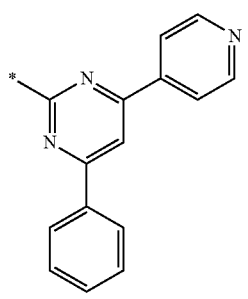
Formula 10-102
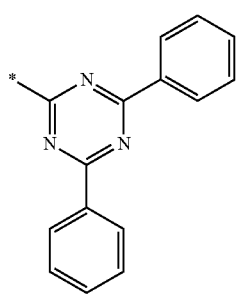
Formula 10-103
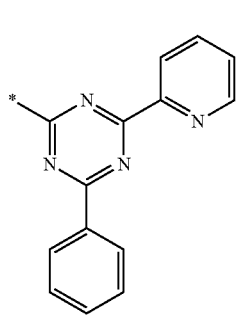
Formula 10-104
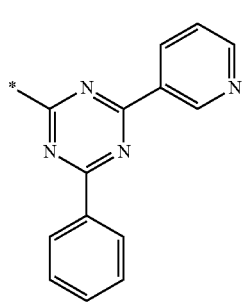

Formula 10-105
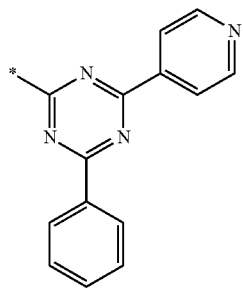

Formula 10-106
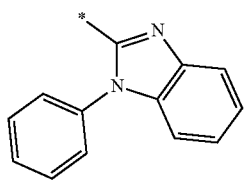

Formula 10-107
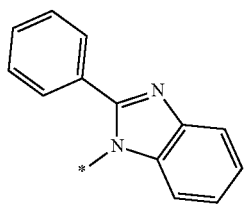

Formula 10-108
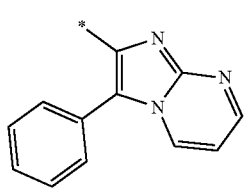

Formula 10-109
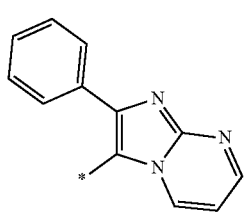

Formula 10-110
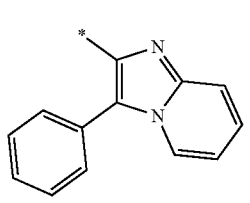

Formula 10-111
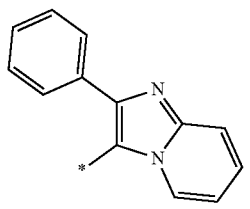

Formula 10-112
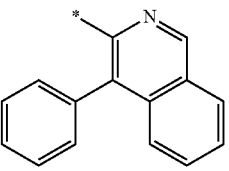

Formula 10-113
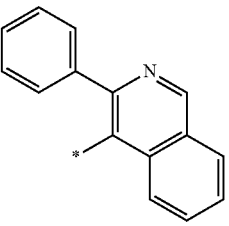

Formula 10-114
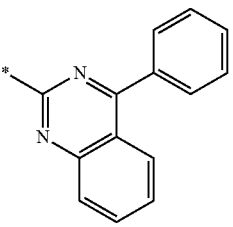

Formula 10-115
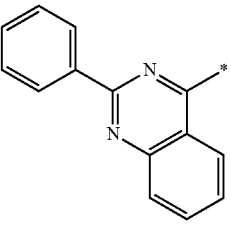

Formula 10-116
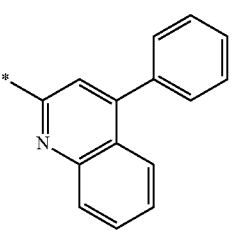

Formula 10-117
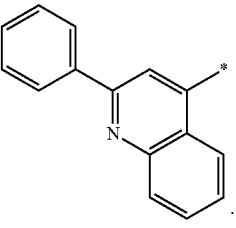

In Formulae 6-1 to 6-43 and Formulae 10-1 to 10-117, * is a binding site with an adjacent atom.

In some embodiments, in Formulae 2A to 2E, $R_1$ to $R_{12}$ may be each independently selected from a binding site to $A_1$ in Formula 1 (e.g., a chemical bond such as a single bond coupled to $A_1$ in Formula 1), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formulae 2A to 2E, $R_1$ to $R_{12}$ may each independently be a binding site to $A_1$ in Formula 1, where at least one selected from $R_1$ to $R_{12}$ is a binding site to $A_1$ and the number of binding sites is equal to n1 in Formula 1.

In Formula 1, n1 may be an integer selected from 1 to 5. In some embodiments, n1 in Formula 1 may be 1 or 2. For example, n1 in Formula 1 may be 1. However, embodiments of the present disclosure are not limited thereto.

In Formulae 2-1 to 2-4, $L_1$ to $L_{10}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formulae 2-1 to 2-4, $L_1$ to $L_{10}$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), where $Q_{33}$ to $Q_{35}$ may be each independently selected from a $C_1$-$C_{10}$ alkyl group, a $C_1$-$C_{10}$ alkoxy group, a phenyl group, and a naphthyl group.

For example, in Formulae 2-1 to 2-4, $L_1$ to $L_{10}$ may be each independently selected from groups represented by Formula 3-1 to Formula 3-42.

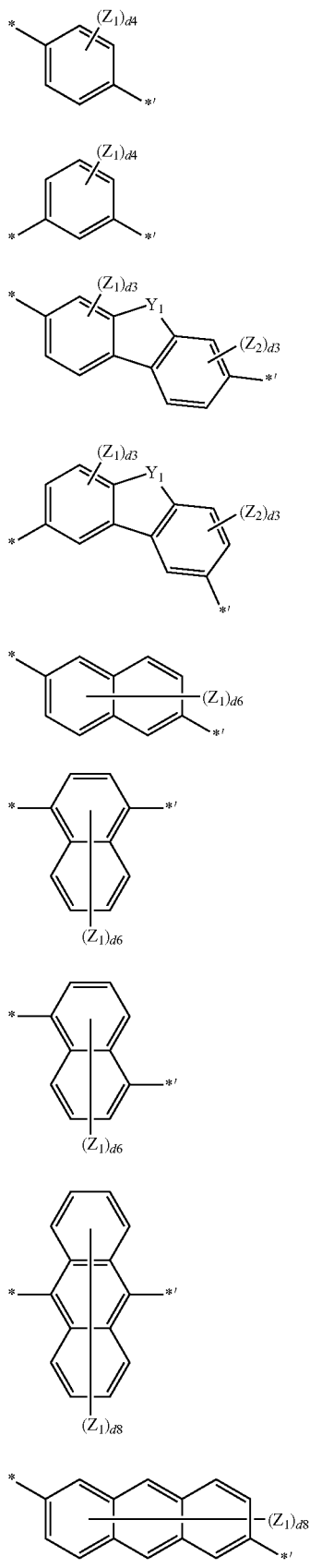

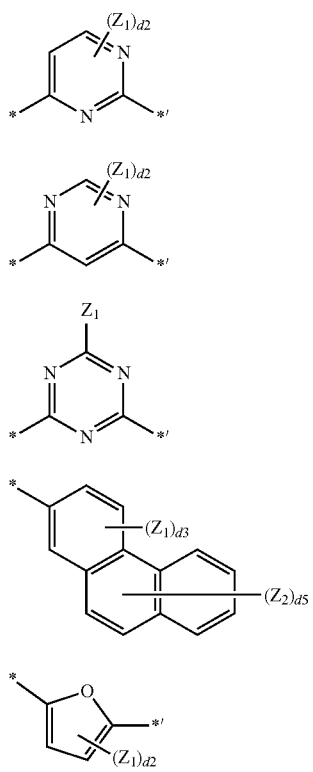
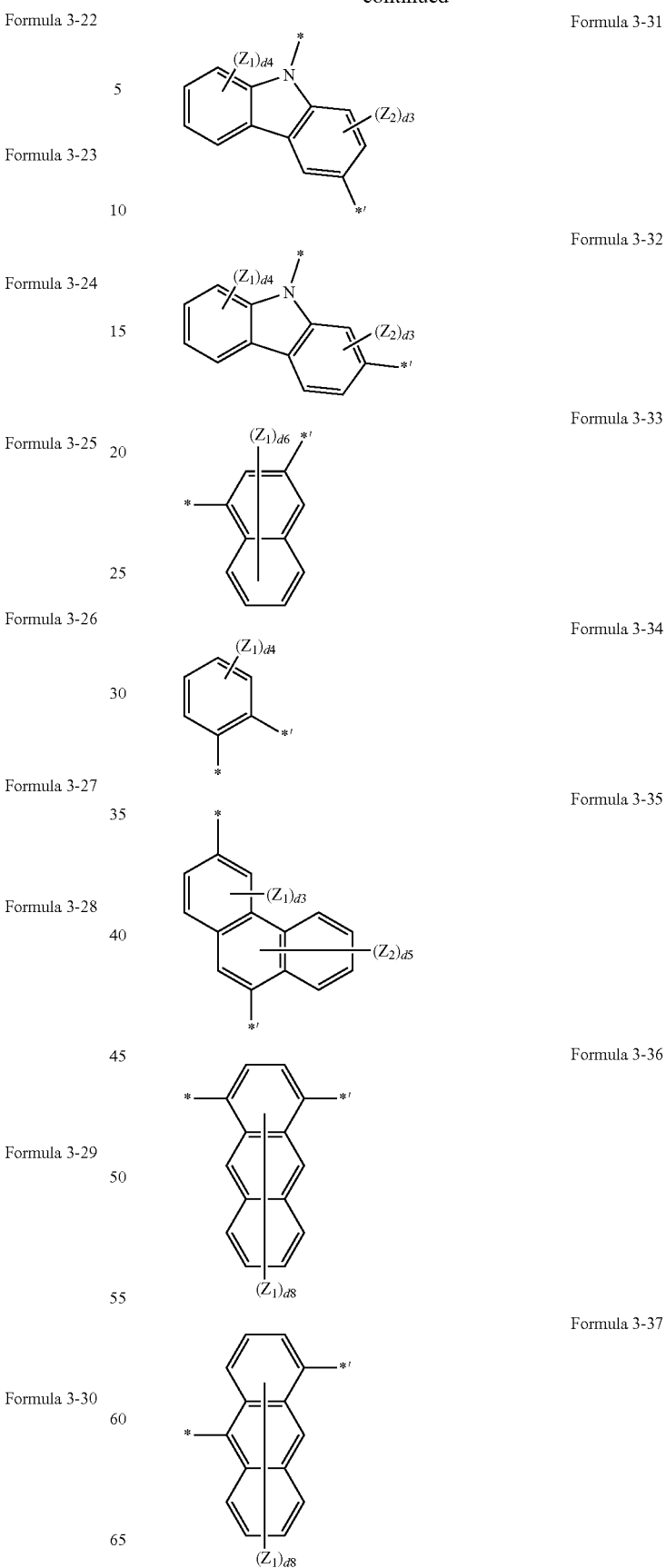

-continued

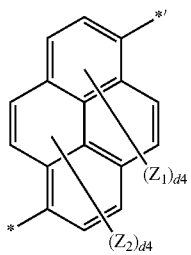
Formula 3-38

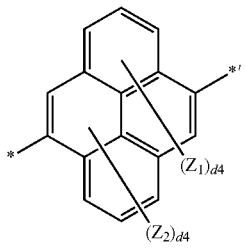
Formula 3-39

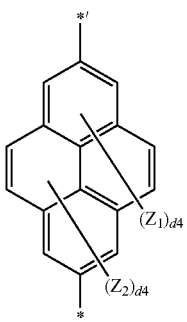
Formula 3-40

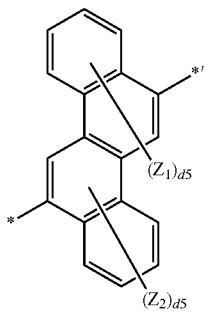
Formula 3-41

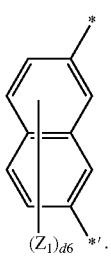
Formula 3-42

In Formulae 3-1 to 3-42, $Y_1$ may be selected from O, S, $C(Z_3)(Z_4)$, $N(Z_5)$, and $Si(Z_6)(Z_7)$, $Z_1$ to $Z_7$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{33})(Q_{34})(Q_{35})$, where $Q_{33}$ to $Q_{35}$ may be each independently selected from a $C_1$-$C_{10}$ alkyl group, a $C_1$-$C_{10}$ alkoxy group, a phenyl group, and a naphthyl group, d2 may be 1 or 2,
d3 may be an integer selected from 1 to 3,
d4 may be an integer selected from 1 to 4,
d5 may be an integer selected from 1 to 5,
d6 may be an integer selected from 1 to 6,
d8 may be an integer selected from 1 to 8, and
* and *' may each be a binding site with an adjacent atom.

In some embodiments, in Formulae 2-1 to 2-4, $L_1$ to $L_{10}$ may be each independently selected from groups represented by Formula 4-1 to Formula 4-36. However embodiments of the present disclosure are not limited thereto.

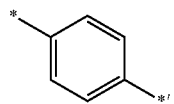
Formula 4-1

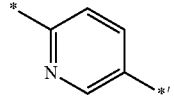
Formula 4-2

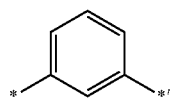
Formula 4-3

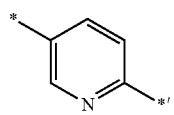
Formula 4-4

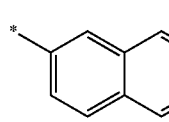
Formula 4-5

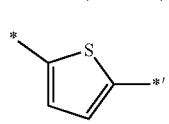
Formula 4-6

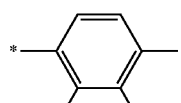
Formula 4-7

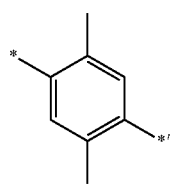
Formula 4-8

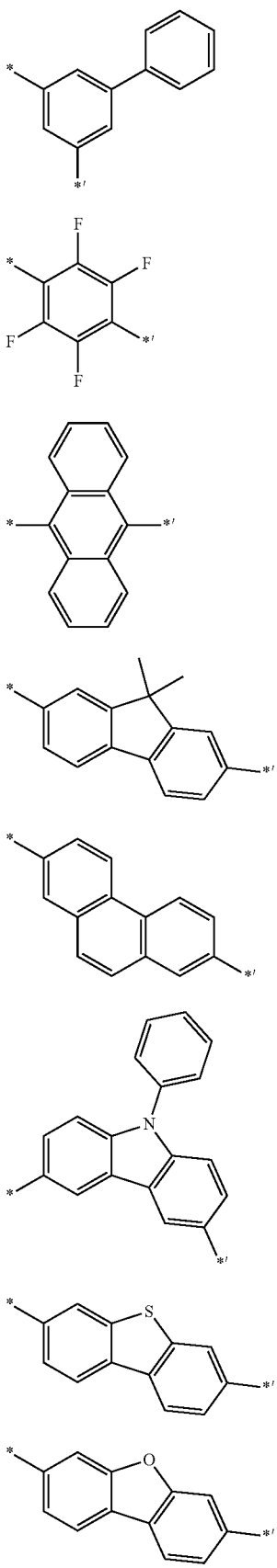
Forumla 4-9
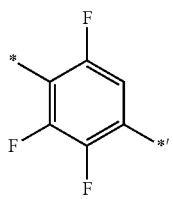
Formula 4-17
Formula 4-10
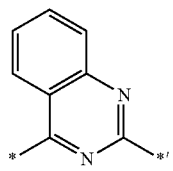
Formula 4-18
Formula 4-11
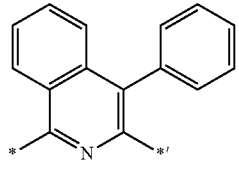
Formula 4-19
Formula 4-12
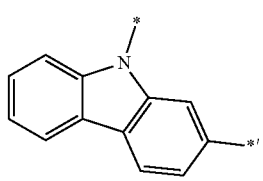
Formula 4-20
Formula 4-13
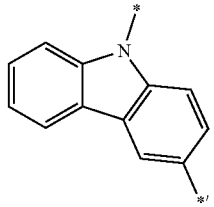
Formula 4-21
Formula 4-14
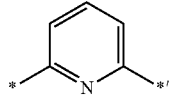
Formula 4-22
Formula 4-23
Formula 4-15
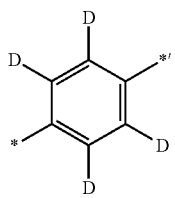
Formula 4-24
Formula 4-16
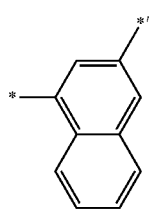
Formula 4-25

-continued

Formula 4-26

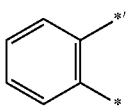

Formula 4-27

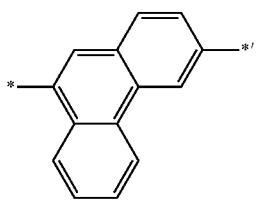

Formula 4-28

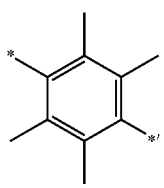

Formula 4-29

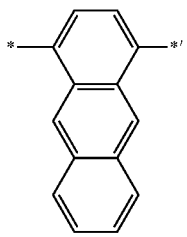

Formula 4-30

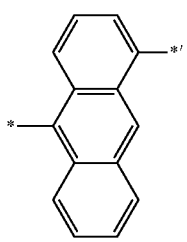

Formula 4-31

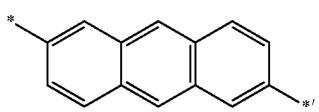

Formula 4-32

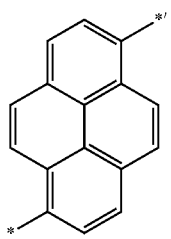

Formula 4-33

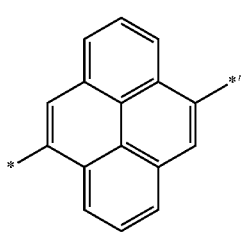

Formula 4-34

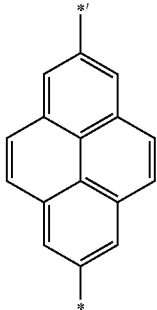

Formula 4-35

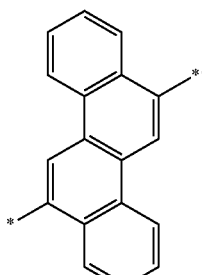

Formula 4-36

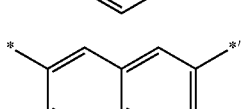

In Formulae 4-1 and 4-36, * and *′ may each be a binding site with an adjacent atom.

In Formulae 2-1 to 2-4, a1 to a10 may each independently be an integer selected from 0 to 5. When a1 is 0, *-(L$_1$)$_{a1}$-* may be a single bond. When a1 is 2 or greater, at least two L$_1$s may be the same as or different from each other. In Formulae 2-1 to 2-4, each of a2 to a10 may be understood based on the description of a1 and the respective structures of Formulae 2-1 to 2-4.

For example, in Formulae 2-1 to 2-4 a1, a4, a7, and a9 may be each independently 0, 1, 2, or 3. In some embodiments, a1, a4, a7, and a9 in Formulae 2-1 to 2-4 may be each independently 1, 2, or 3. In some embodiments, a1, a4, a7, and a9 in Formulae 2-1 to 2-4 may be each independently 1 or 2. However, embodiments of the present disclosure are not limited thereto.

In some embodiments, in Formulae 2-1 to 2-4, a2, a3, a5, a6, a8, and a10 may be each independently 0, 1, or 2. However, embodiments of the present disclosure are not limited thereto.

In Formulae 2-1 to 2-4, Ar$_1$ to Ar$_6$ may each independently be selected from groups represented by Formulae 2-11 to 2-17, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

Formula 2-11

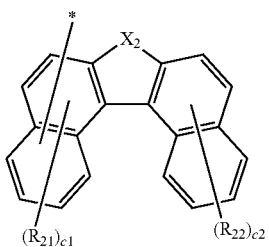

Formula 2-12

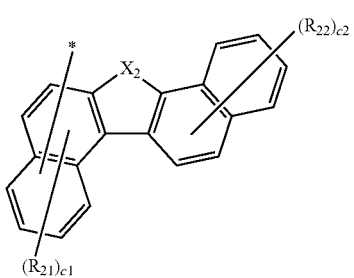

Formula 2-13

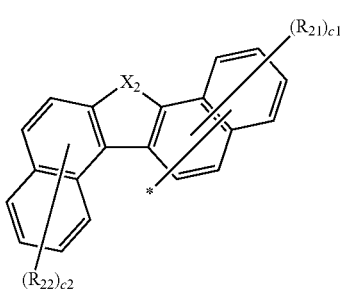

Formula 2-14

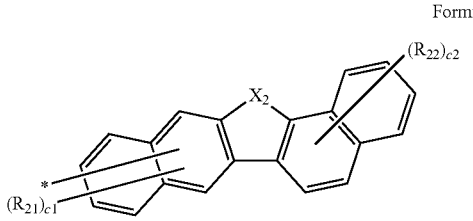

Formula 2-15

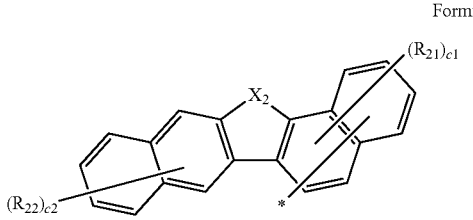

Formula 2-16

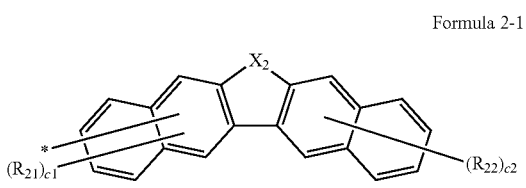

Formula 2-17

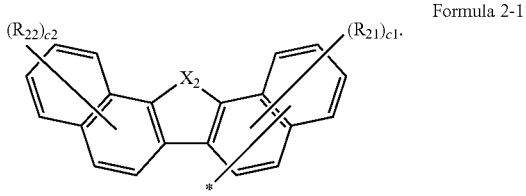

For example, in Formulae 2-1 to 2-4, $Ar_1$ to $Ar_6$ may be each independently selected from:

groups represented by Formulae 2-11 to 2-17 (for example, groups represented by Formulae 2-11(1), 2-11(2), 2-12(1), 2-12(2), 2-14(1), 2-16(1), and/or 2-17(1));

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group and —Si($Q_{33}$)($Q_{34}$)($Q_{35}$), where $Q_{33}$ to $Q_{35}$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

Formula 2-11(1)

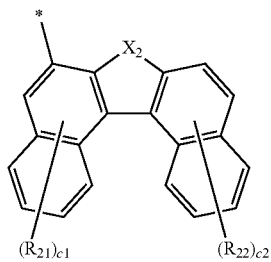

Formula 2-11(2)

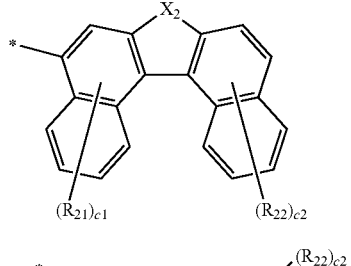

Formula 2-12(1)

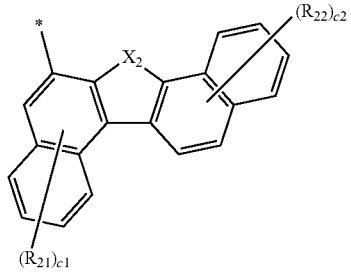

Formula 2-12(2)

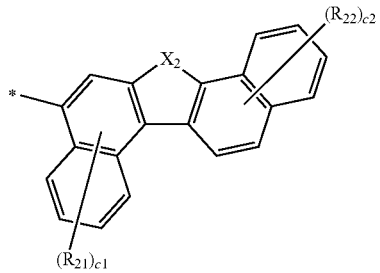

Formula 2-14(1)

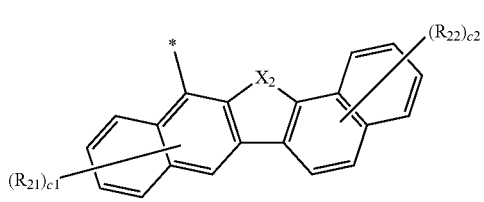

Formula 2-16(1)

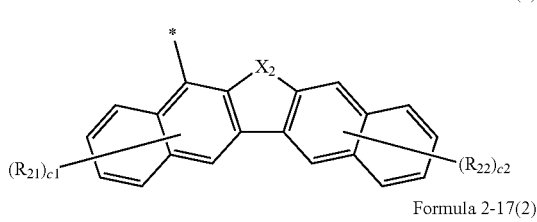

Formula 2-17(2)

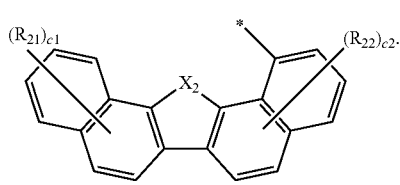

In some embodiments, in Formulae 2-1 to 2-4, $Ar_1$ to $Ar_6$ may be each independently selected from:

groups represented by Formulae 2-11 to 2-17 (for example, groups represented by Formulae 2-11(1), 2-11(2), 2-12(1), 2-12(2), 2-14(1), 2-16(1), and/or 2-17(1));

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), where $Q_{33}$ to $Q_{35}$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In Formulae 2-11 to 2-17 (for example, Formulae 2-11(1), 2-11(2), 2-12(1), 2-12(2), 2-14(1), 2-16(1), and 2-17(1)), $R_{21}$ and $R_{22}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$) where $Q_1$ to $Q_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, in Formula 2-11 to 2-17 (for example, Formulae 2-11(1), 2-11(2), 2-12(1), 2-12(2), 2-14(1), 2-16(1), and 2-17(1)), $R_{21}$ and $R_{22}$ may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$); and —Si($Q_3$)($Q_4$)($Q_5$), where $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, in Formulae 2-11 to 2-17 (for example, Formulae 2-11(1), 2-11(2), 2-12(1), 2-12(2), 2-14(1), 2-16(1), and 2-17(1)), $R_{21}$ and $R_{22}$ may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —$Si(Q_{33})(Q_{34})(Q_{35})$; and —$Si(Q_3)(Q_4)(Q_5)$, where $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In Formulae 2-11 to 2-17 (for example, Formulae 2-11(1), 2-11(2), 2-12(1), 2-12(2), 2-14(1), 2-16(1), and 2-17(1)), c1 may be an integer selected from 0 to 5, and c2 may be an integer selected from 0 to 6. For example, c1 and c2 may be each independently 0, 1, or 2. However, embodiments of the present disclosure are not limited thereto.

In Formulae 2-1 to 2-4, b1 to b4 may be each independently an integer selected from 1 to 5. For example, b1 to b4 may be each independently 1 or 2. However, embodiments of the present disclosure are not limited thereto.

In some embodiments, $R_1$ to $R_{12}$ in Formulae 2A to 2E may be each independently selected from a binding site to $A_1$ in Formula 1 (e.g., a chemical bond such as a single bond coupled to $A_1$ in Formula 1), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75, and —$Si(Q_3)(Q_4)(Q_5)$;

$Ar_1$ to $Ar_6$ in Formulae 2-1 to 2-4 may be each independently selected from groups represented by Formulae 2-11 to 2-17 and groups represented by Formulae 5-1 to 5-75; and $R_{21}$ and $R_{22}$ in Formulae 2-11 to 2-17 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75, and —$Si(Q_3)(Q_4)(Q_5)$, where $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In some other embodiments, $R_1$ to $R_{12}$ in Formulae 2A to 2E may be each independently selected from a binding site to $A_1$ in Formula 1 (e.g., a chemical bond such as a single bond coupled to $A_1$ in Formula 1), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 6-1 to 6-43, groups represented by Formulae 10-1 to 10-117, and —$Si(Q_3)(Q_4)(Q_5)$;

$Ar_1$ to $Ar_6$ in Formulae 2-1 to 2-4 may be each independently selected from groups represented by Formulae 2-11 to 2-17, groups represented by Formulae 6-1 to 6-43, and groups represented by Formulae 10-1 to 10-117; and $R_{21}$ and $R_{22}$ in Formulae 2-11 to 2-17 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 6-1 to 6-43, groups represented by Formulae 10-1 to 10-117, and —$Si(Q_3)(Q_4)(Q_5)$, where $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In some embodiments, the condensed cyclic compound of Formula 1 may be represented by one of Formulae 2A-1 to 2E-1.

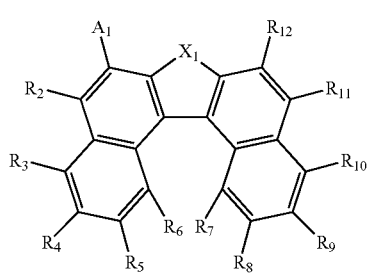

Formula 2A-1

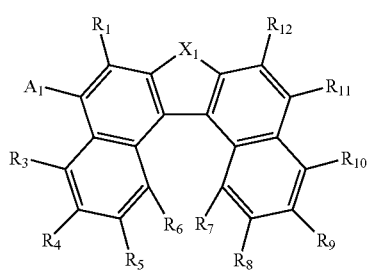

Formula 2A-2

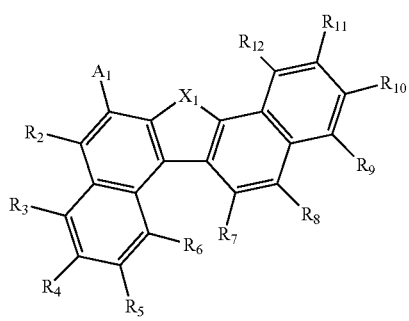

Formula 2B-1

Formula 2B-2
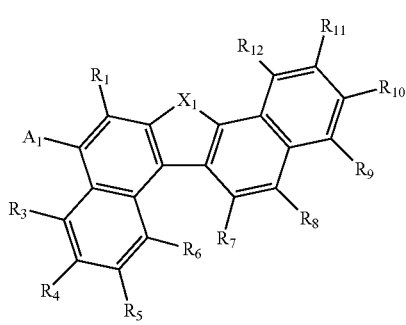

Formula 2D-1
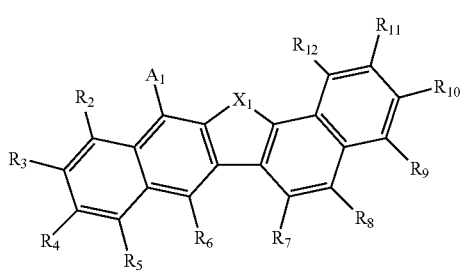

Formula 2E-1
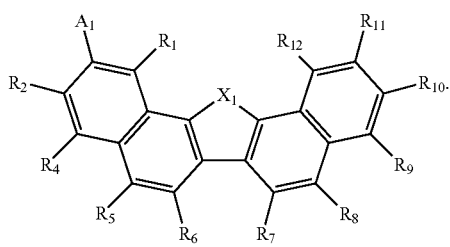

In Formula 2A-1 to 2E-1, $X_1$, $R_1$ to $R_{12}$, and $A_1$ may be defined the same as those described herein.

For example, in Formulae 2A-1 to 2E-1, $X_1$ may be O, and $R_1$ to $R_{12}$ may be each independently selected from a binding site to $A_1$ in Formula 1, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75 (for example, the groups represented by Formulae 6-1 to 6-43 and/or the groups represented by Formulae 10-1 to 10-117), and —Si($Q_3$)($Q_4$)($Q_5$), where $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In some embodiments, the condensed cyclic compound of Formula 1 may be represented by one of Formulae 1(1) to 1(8).

Formula 1(1)
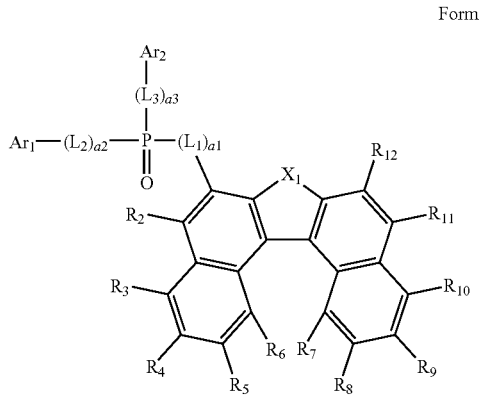

Formula 1(2)
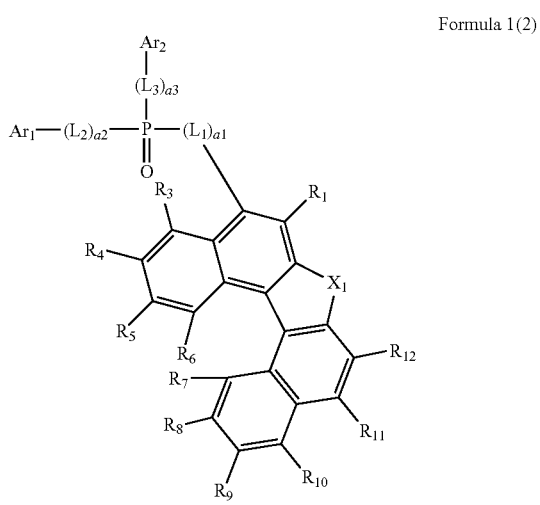

Formula 1(3)
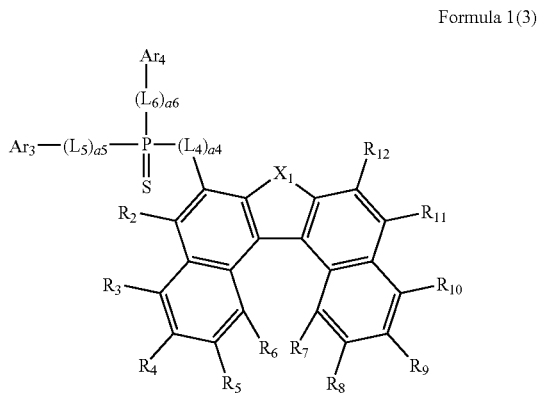

-continued

Formula 1(4)

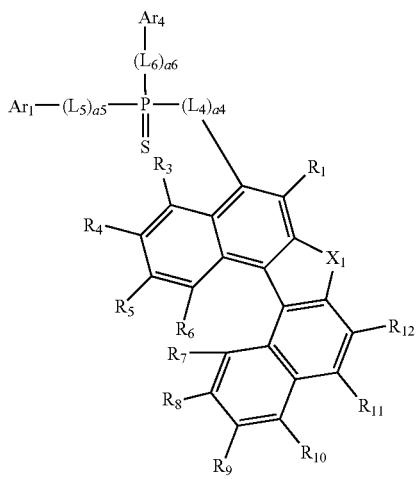

Formula 1(5)

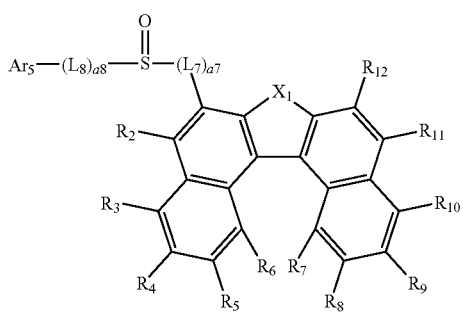

Formula 1(6)

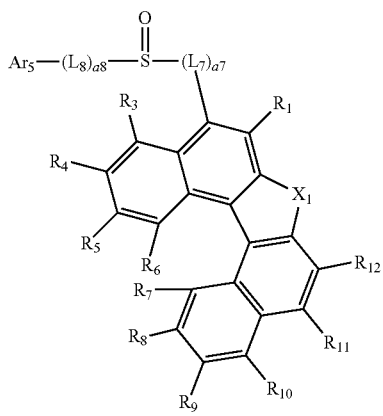

Formula 1(7)

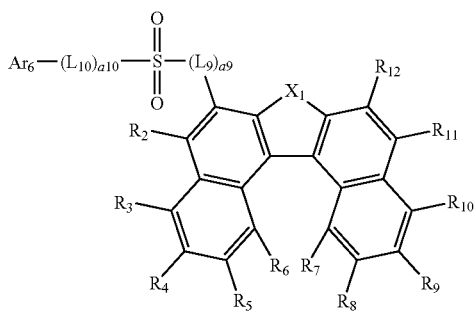

-continued

Formula 1(8)

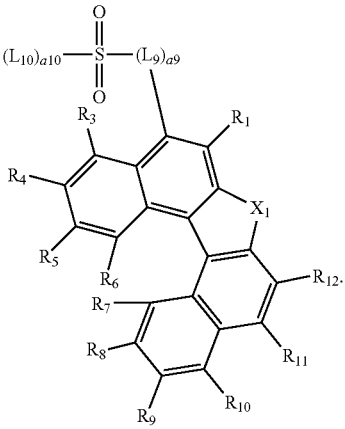

In Formulae 1(1) to 1(8), $X_1$, $R_1$ to $R_{12}$, $L_1$ to $L_{10}$, a1 to a10, and $Ar_1$ to $Ar_6$ may be defined the same as those described herein.

For example, in Formulae 1(1) to 1(8), $X_1$ may be O, $L_1$ to $L_{10}$ may be each independently selected from the groups represented by Formulae 3-1 to 3-42, a1, a4, a7, and a9 may be each independently 1 or 2, a2, a3, a5, a6, a8, and a10 may be each independently 0, 1, or 2, $R_1$ to $R_{12}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, the groups represented by Formulae 5-1 to 5-75 (for example, the groups represented by Formulae 6-1 to 6-43 and/or Formulae 10-1 to 10-117), and —Si($Q_3$)($Q_4$)($Q_5$), $Ar_1$ to $Ar_6$ may be each independently selected from the groups represented by Formulae 2-11 to 2-17 (for example, the groups represented by Formulae 2-11(1), 2-11(2), 2-12(1), 2-12(2), 2-14(1), 2-16(1), and/or 2-17(1)), and the groups represented by Formulae 5-1 to 5-75 (for example, the groups represented by Formulae 6-1 to 6-43 and/or Formulae 10-1 to 10-117), and $R_{21}$ and $R_{22}$ in Formulae 2-11 to 2-17 (for example, Formulae 2-11(1), 2-11(2), 2-12(1), 2-12(2), 2-14(1), 2-16(1), and 2-17(1)) may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, the groups represented by Formulae 5-1 to 5-75 (for example, the groups represented by Formulae 6-1 to 6-43 and/or Formulae 10-1 to 10-117), and —Si($Q_3$)($Q_4$)($Q_5$), where $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the present disclosure are not limited thereto.

In some embodiments, the condensed cyclic compound of Formula 1 may be one of Compounds 1 to 45. However, embodiments of the present disclosure are not limited thereto.

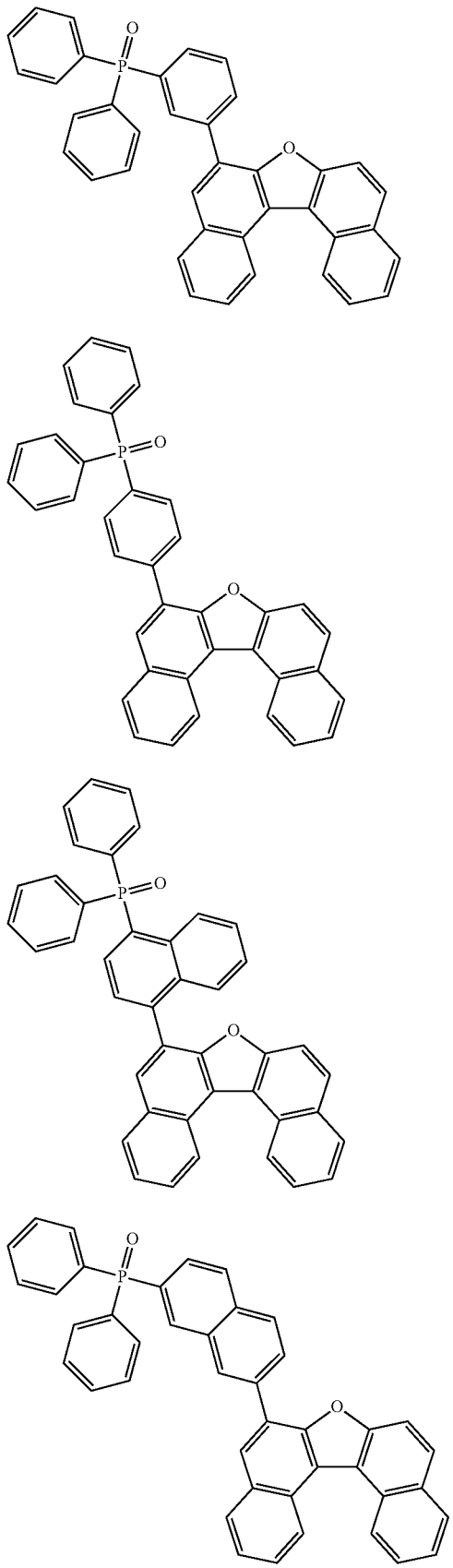
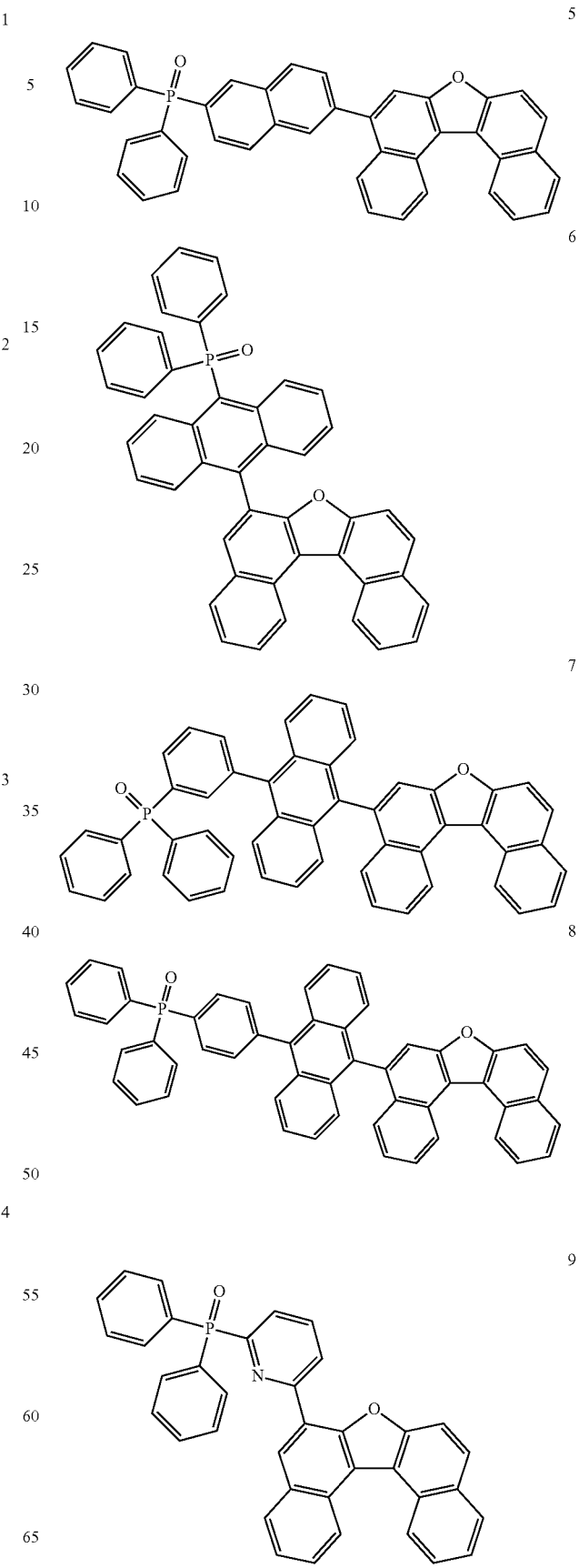

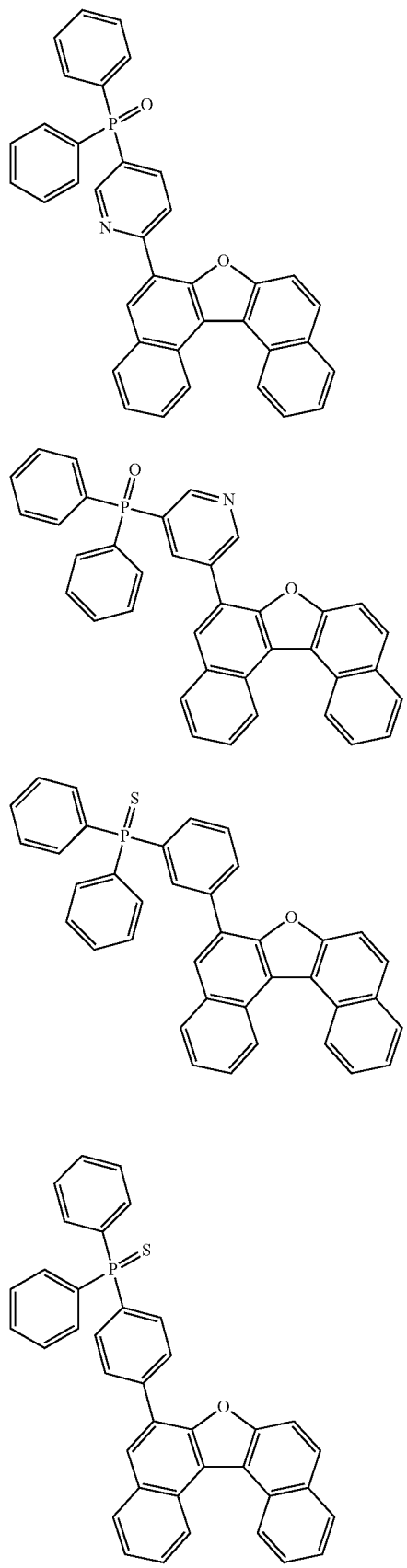
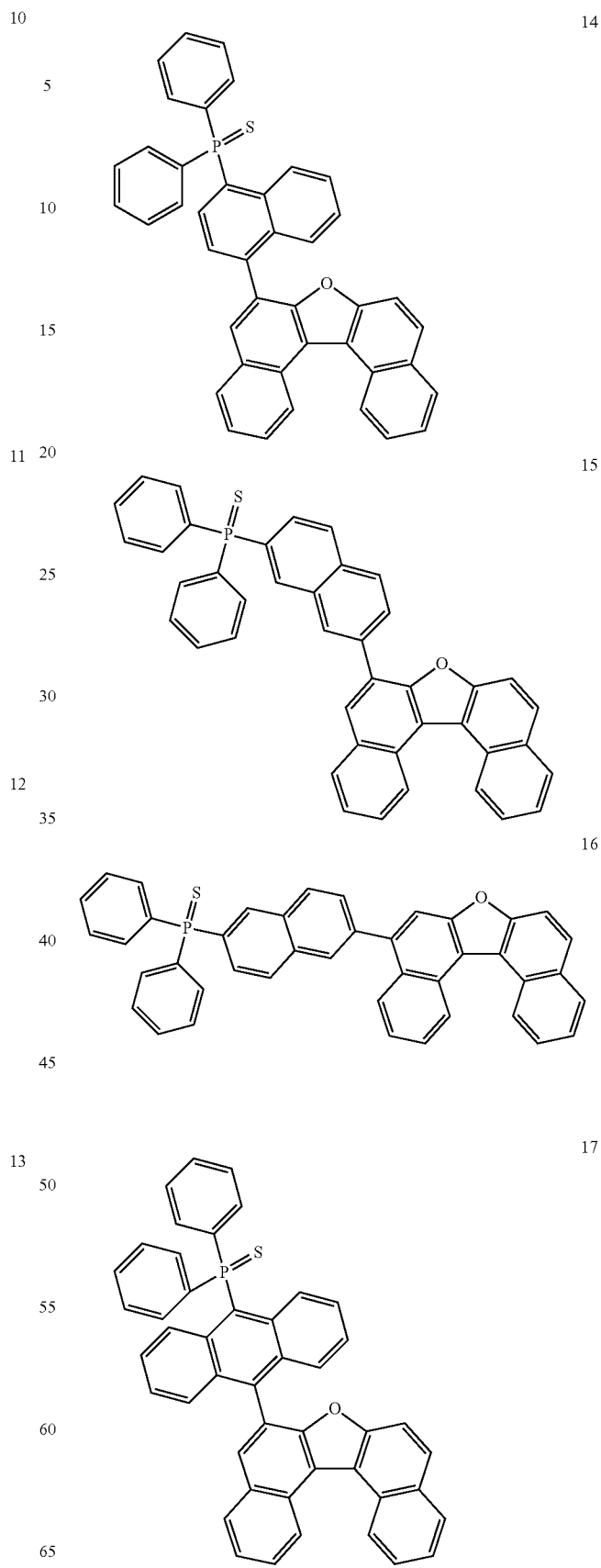

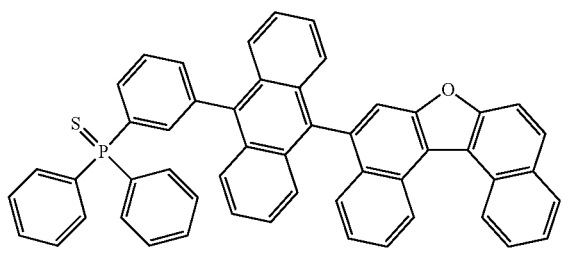
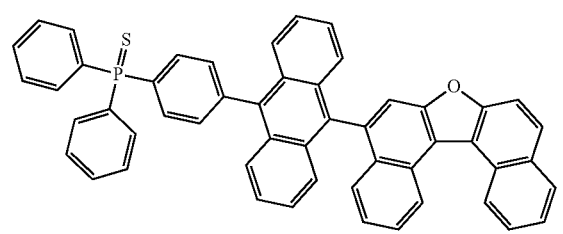
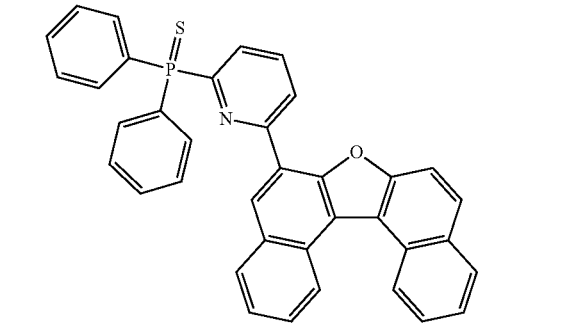
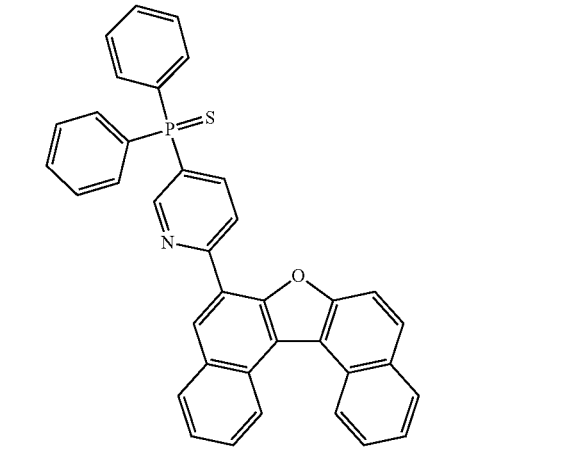
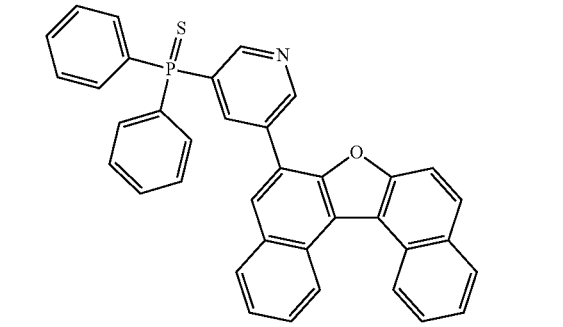
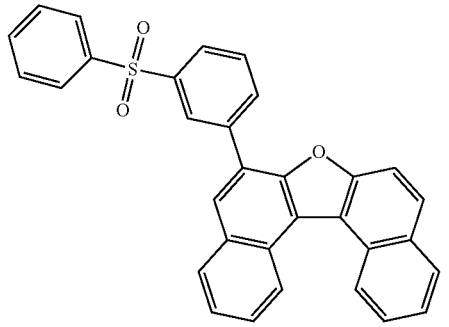
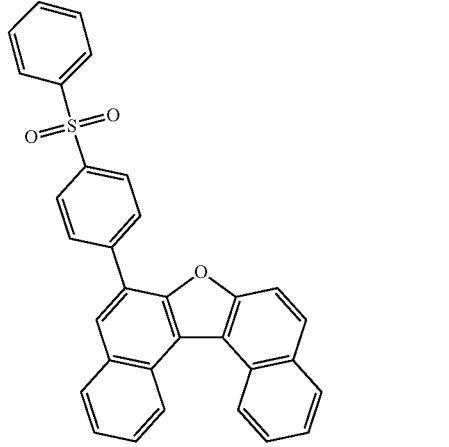
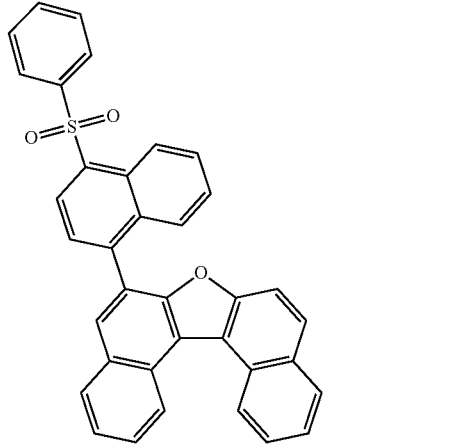
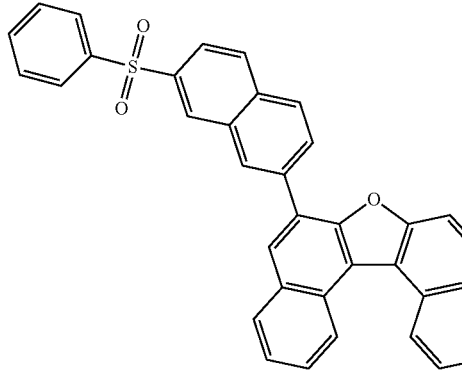

27
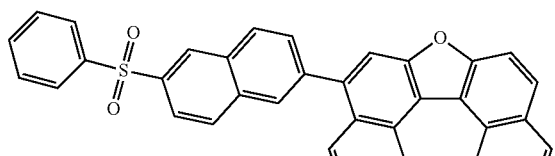
28
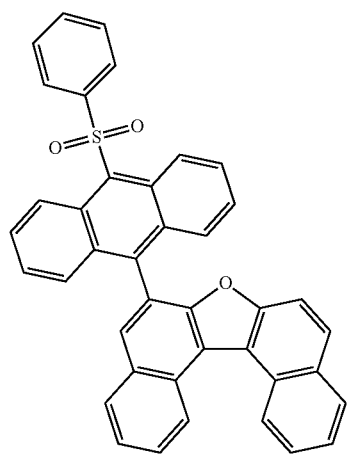
29
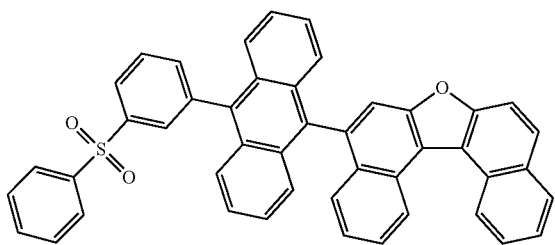
30
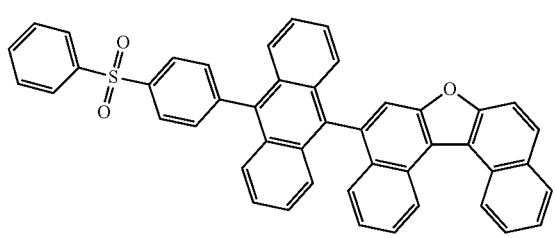
31
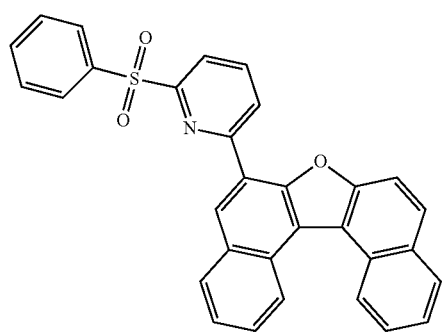
32
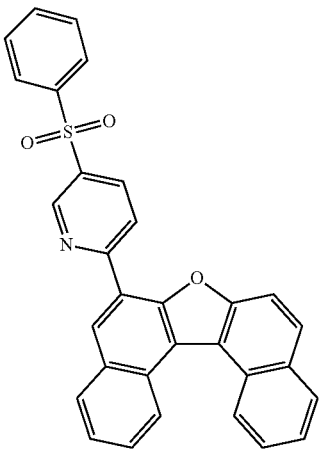
33
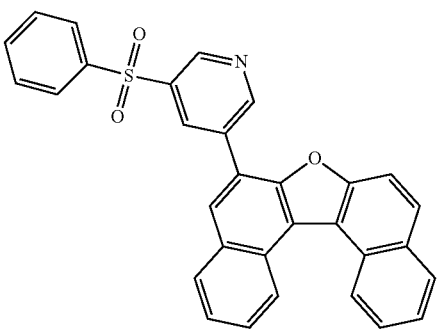
34
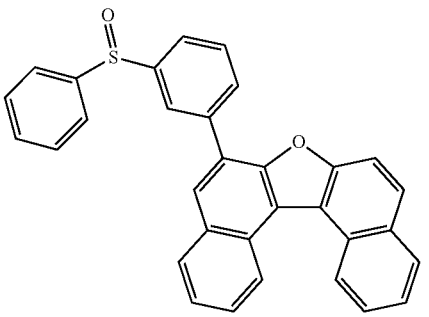
35
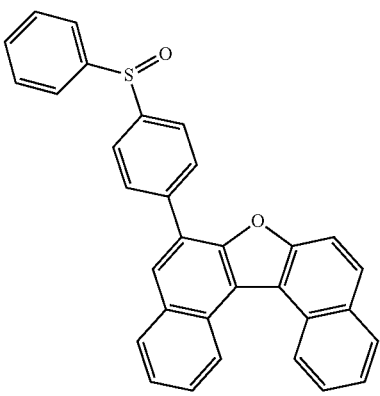

36
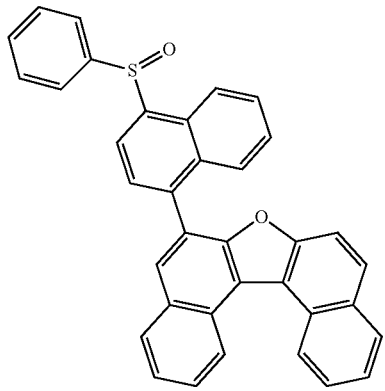
37
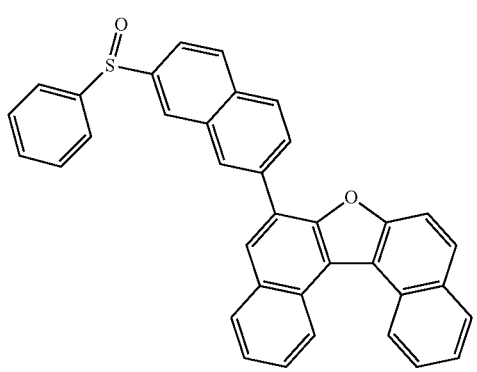
38
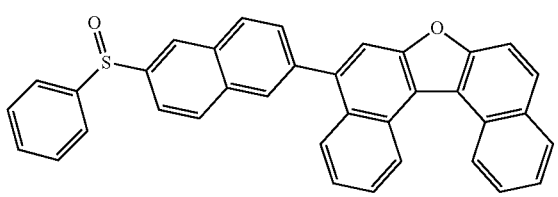
39
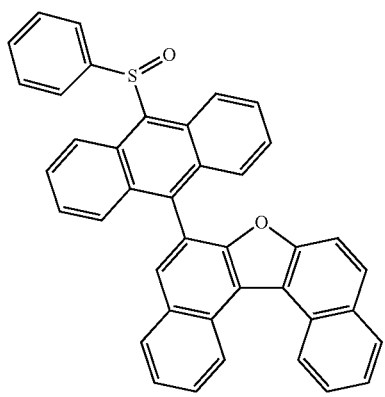
40
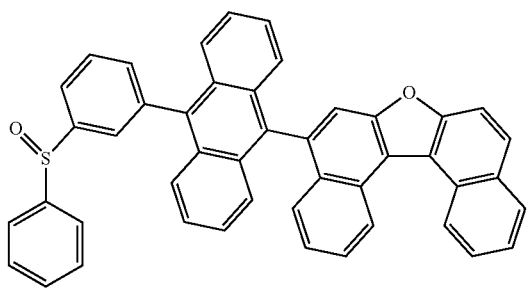
41
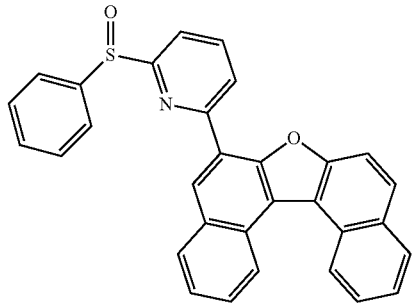
42
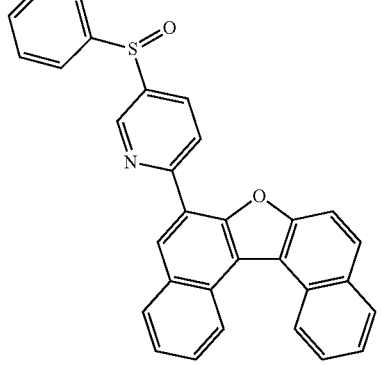
43
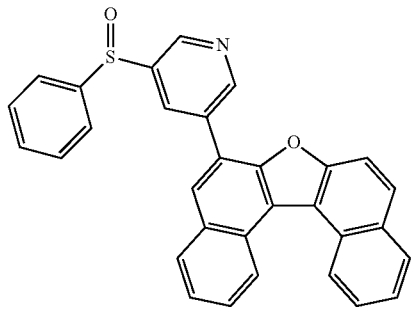
44

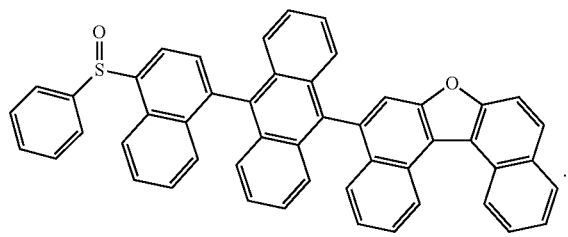

In the condensed cyclic compound of Formula 1, $A_2$ may be selected from the groups represented by Formulae 2A to 2E that include cores having a long conjugation length. Accordingly, the condensed cyclic compound of Formula 1 may have improved electron transport ability.

In the condensed cyclic compound of Formula 1, $A_1$ may be selected from the groups represented by Formulae 2-1 to 2-4. The groups represented by Formulae 2-1 to 2-4 may form an intramolecular dipole in the condensed cyclic compound of Formula 1, and consequentially may improve the electron transport ability of the condensed cyclic compound of Formula 1. Due to the groups represented by Formulae 2-1 to 2-4, the condensed cyclic compound of Formula 1 may have a bulky structure, and thus improve amorphous characteristics when included in a film. Therefore, an electronic device, for example, an organic light-emitting device, including the condensed cyclic compound of Formula 1, may have improved long lifetime characteristics.

A synthesis method of the condensed cyclic compound of Formula 1 should be apparent to one of ordinary skill in the art based on the examples that are described below.

At least one selected from the condensed cyclic compounds of Formula 1 may be used between a pair of electrodes of an organic light-emitting device. For example, the condensed cyclic compound of Formula 1 may be included in at least one selected from an electron transport region and an emission layer of an organic light-emitting device. In some embodiments, the condensed cyclic compound of Formula 1 may be used as a material for capping layers positioned outside a pair of electrodes of an organic light-emitting device (e.g., positioned on the sides of the first and/or second electrode, opposite from the organic layer).

According to some embodiments of the present disclosure, an organic light-emitting device includes: a first electrode; a second electrode facing the first electrode; and an organic layer between the first electrode and the second electrode, the organic layer including an emission layer and further including at least one selected from the condensed cyclic compounds of Formula 1.

As used herein, the expression "(an organic layer) may include at least one selected from the condensed cyclic compounds of Formula 1" may indicate that "(the organic layer) may include one of the condensed cyclic compounds of Formula 1 or at least two different types (kinds) of the condensed cyclic compounds of Formula 1."

For example, the organic layer may include only Compound 1 as the at least one selected from the condensed cyclic compounds of Formula 1. For example, Compound 1 may be in an electron transport layer of the organic light-emitting device. In some embodiments, the organic layer may include Compounds 1 and 2 as the at least one selected from the condensed cyclic compounds of Formula 1. For example, Compounds 1 and 2 may be in the same layer (for example, both in the electron transport layer) or in different layers (for example, Compound 1 may be in the electron transport layer, and Compound 2 may be in the emission layer).

In some embodiments, the organic layer may include i) a hole transport region between the first electrode (e.g., an anode) and the emission layer and including at least one selected from a hole injection layer, a hole transport layer, a buffer layer, and an electron blocking layer, and ii) an electron transport region between the emission layer and the second electrode (e.g., a cathode) and including at least one selected from a hole blocking layer, an electron transport layer, and an electron injection layer. At least one selected from the electron transport region and the emission layer may include the at least one selected from the condensed cyclic compounds of Formula 1. For example, the electron transport region of the organic light-emitting device may include an electron transport layer, and the electron transport layer may include the at least one selected from the condensed cyclic compounds of Formula 1. In some embodiments, the emission layer of the organic light-emitting device may include the at least one selected from the condensed cyclic compounds of Formula 1. The condensed cyclic compound of Formula 1 in the emission layer may serve as a host, and the emission layer may further include a dopant. For example, the dopant may be a phosphorescent dopant or a fluorescent dopant.

In some embodiments, the organic light-emitting device may further include at least one selected from a first capping layer and a second capping layer, the first capping layer being positioned on an optical path along which light generated in the emission layer passes outwards through the first electrode, and the second capping layer being positioned on an optical path along which light generated in the emission layer passes outwards through the second electrode, and at least one selected from the first and second capping layers may include the at least one selected from the condensed cyclic compounds of Formula 1.

For example, the organic light-emitting device may have i) a stack structure in which the first electrode, the organic layer, the second electrode, and the second capping layer are sequentially stacked upon one another in the stated order, ii) a stack structure in which the first capping layer, the first electrode, the organic layer, and the second electrode are sequentially stacked upon one another in the stated order, or iii) a stack structure in which the first capping layer, the first electrode, the organic layer, the second electrode, and the second capping layer are sequentially stacked upon one another in the stated order, where at least one selected from the first and second capping layers may include the at least one selected from the condensed cyclic compounds of Formula 1.

As used herein, the term "organic layer" may refer to a single layer and/or a plurality of layers positioned between the first and second electrodes of the organic light-emitting device. A material in the "organic layer" is not limited to an organic material.

Figure 1:
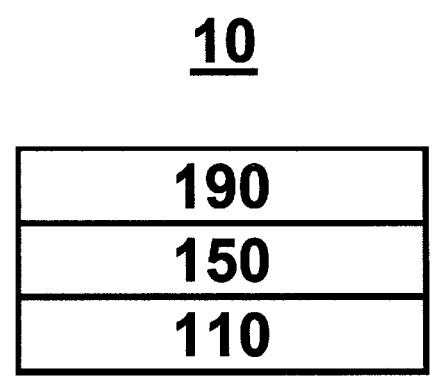

Hereinafter, a structure of an organic light-emitting device according to one or more embodiments of the present disclosure and a method of manufacturing the same will now be described with reference to FIG. 1.

FIG. 1 is a schematic sectional view of an organic light-emitting device according to an embodiment of the present disclosure. Referring to FIG. 1, the organic light-emitting device 10 includes a first electrode 110, an organic layer 150, and a second electrode 190.

A substrate may be positioned under the first electrode 110 or on the second electrode 190 in FIG. 1. The substrate may be a glass or transparent plastic substrate with good mechanical strength, thermal stability, transparency, surface smoothness, ease of handling, and/or water resistance.

For example, the first electrode 110 may be formed by depositing or sputtering a first electrode-forming material on the substrate. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and/or ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but is not limited thereto.

The organic layer 150 may be positioned on the first electrode 110. The organic layer 150 may include an emission layer (EML).

The organic layer 150 may further include a hole transport region between the first electrode and the EML, and an electron transport region between the EML and the second electrode.

For example, the hole transport region may include at least one selected from a hole injection layer (HIL), a hole transport layer (HTL), a buffer layer, and an electron blocking layer (EBL). For example, the electron transport layer may include at least one selected from a hole blocking layer (HBL), an electron transport layer (ETL), and an electron injection layer (EIL). However, embodiments of the present disclosure are not limited thereto.

The hole transport region may have a single-layered structure including a single material, a single-layered structure including a plurality of materials, or a multi-layered structure including a plurality of layers including different materials.

In some embodiments, the hole transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially stacked on the first electrode 110 in the order stated above. However, embodiments of the present disclosure are not limited thereto.

When the hole transport region includes a HIL, the HIL may be formed on the first electrode 110 by using any of a variety of suitable methods, for example, by using vacuum deposition, spin coating, casting, Langmuir-Blodgett (LB) deposition, inkjet printing, laser printing, laser induced thermal imaging (LITI), and/or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 5 pm and a heat treatment temperature of about 800° C. to about 200° C.

When the hole transport region includes a HTL, the HTL may be formed on the first electrode 110 or the HIL by using any of a variety of suitable methods, for example, by using vacuum deposition, spin coating, casting, Langmuir-Blodgett (LB) deposition, inkjet printing, laser printing, laser induced thermal imaging (LITI), and/or the like. When the HTL is formed using vacuum deposition and/or spin coating, the conditions for deposition and coating may be similar to the above-described deposition and coating conditions for forming the HIL, and accordingly will not be described in detail.

For example, the hole transport region may include at least one selected from the condensed cyclic compounds of Formula 1. For example, the hole transport region may include a HTL, and the HTL may include the at least one selected from the condensed cyclic compounds of Formula 1.

In some embodiments, the hole transport region may include at least one selected from m-MTDATA, TDATA, 2-TNATA, NPB, 6-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate)(PEDOT/PSS), polyaniline/camphor sulfonic acid (Pani/CSA), polyaniline/poly(4-styrenesulfonate) (PANI/PSS), a compound represented by Formula 201, and a compound represented by Formula 202.

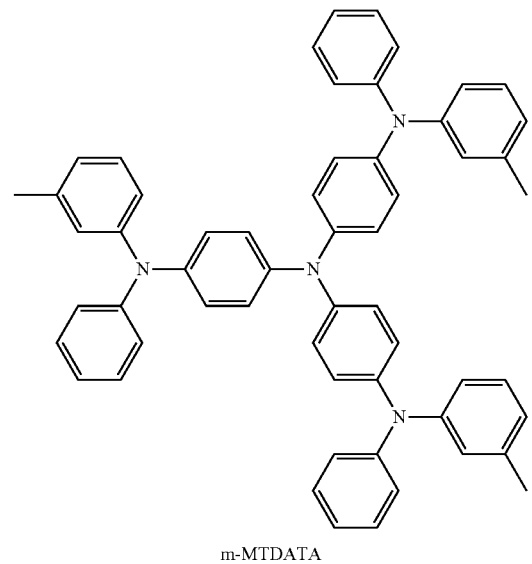

m-MTDATA

-continued
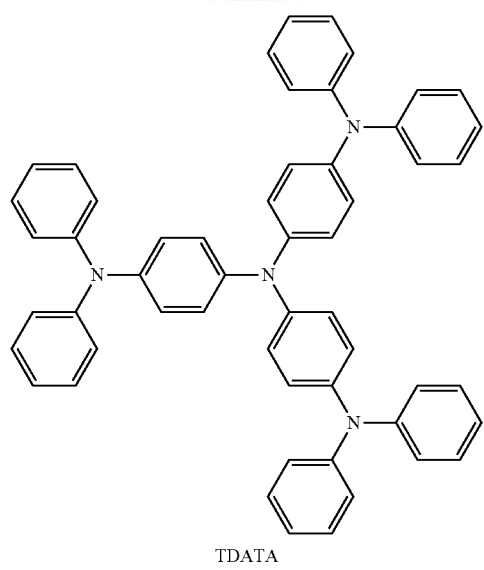
TDATA
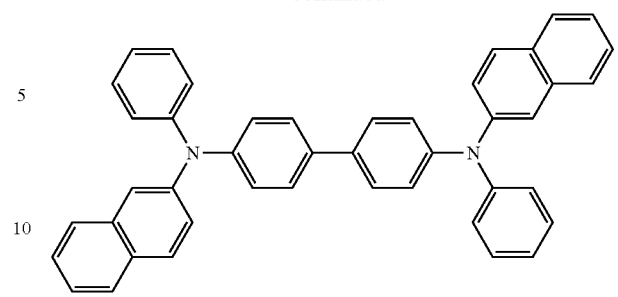
β-NPB
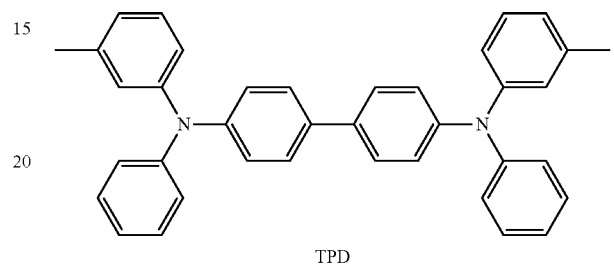
TPD
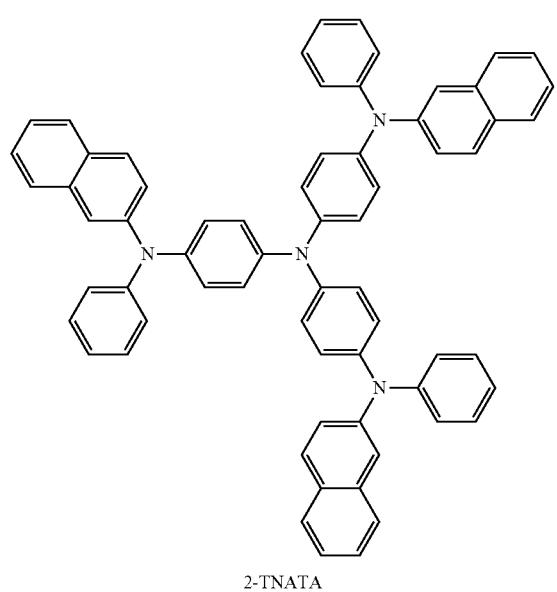
2-TNATA
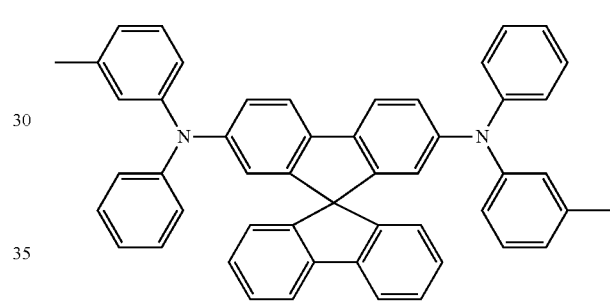
Spiro-TPD
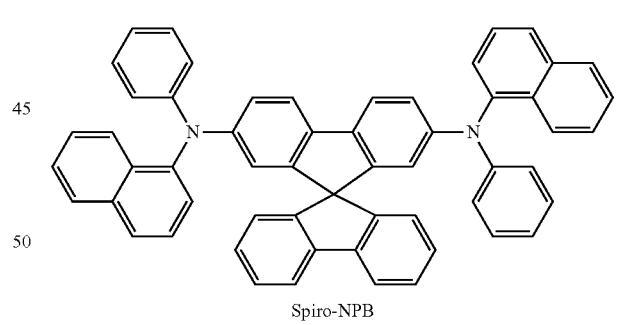
Spiro-NPB
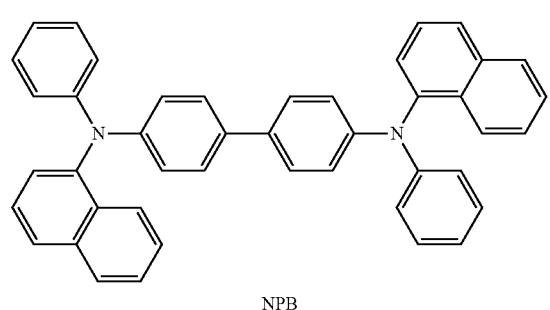
NPB
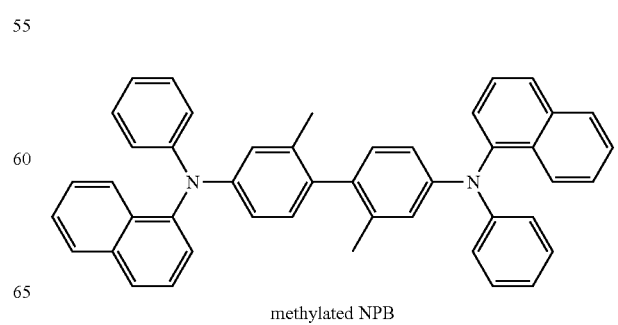
methylated NPB -continued

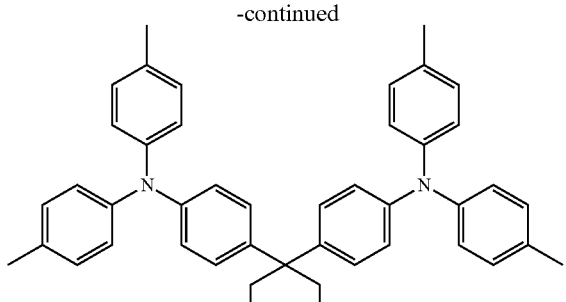

TAPC

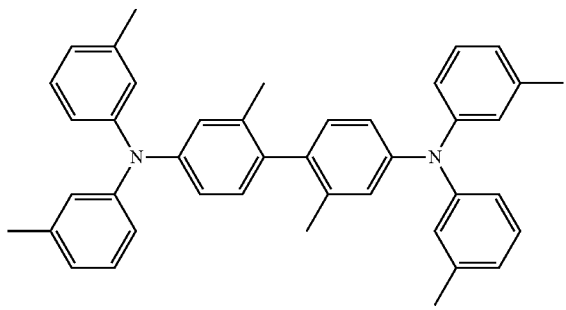

HMTPD

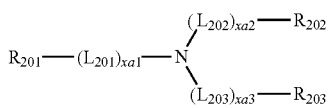

Formula 201

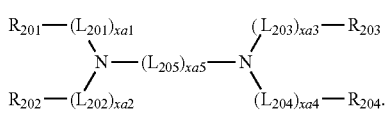

Formula 202

In Formulae 201 and 202, $L_{201}$ to $L_{205}$ may be each independently defined as $L_1$ described above in conjunction with Formula 1, xa1 to xa4 may be each independently selected from 0, 1, 2, and 3, xa5 may be selected from 1, 2, 3, 4, and 5, and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2, xa5 may be 1, 2, or 3, and $R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, embodiments of the present disclosure are not limited thereto.

The compound of Formula 201 may be represented by Formula 201A:

Formula 201A

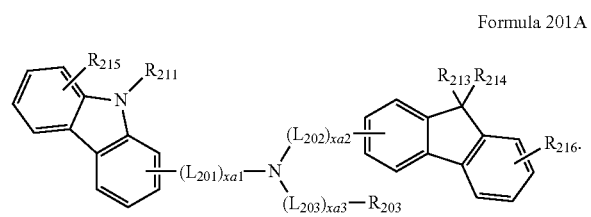

For example, the compound of Formula 201 may be represented by Formula 201A-1, but is not limited thereto:

The compound of Formula 202 may be represented by Formula 202A, but is not limited thereto:

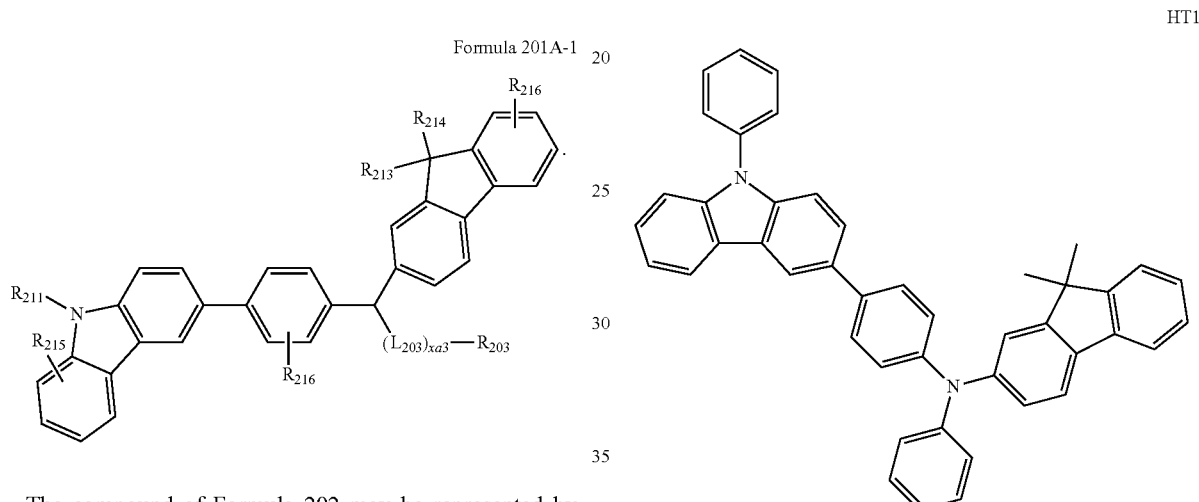

In Formulae 201A, 201A-1, and 202A, $L_{201}$ to $L_{203}$, xa1 to xa3, xa5, and $R_{202}$ to $R_{204}$ may be defined as described in conjunction with Formulae 201 and 202;

$R_{211}$ and $R_{212}$ may be each independently defined as $R_{203}$ described in conjunction with Formula 201; and $R_{213}$ to $R_{216}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201, and the compound represented by Formula 202 may each independently include compounds HT1 to HT20, but are not limited thereto.

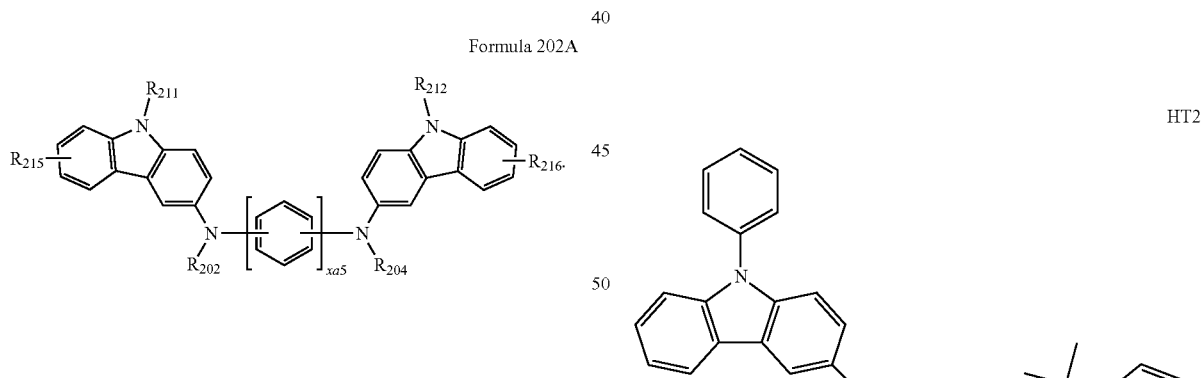

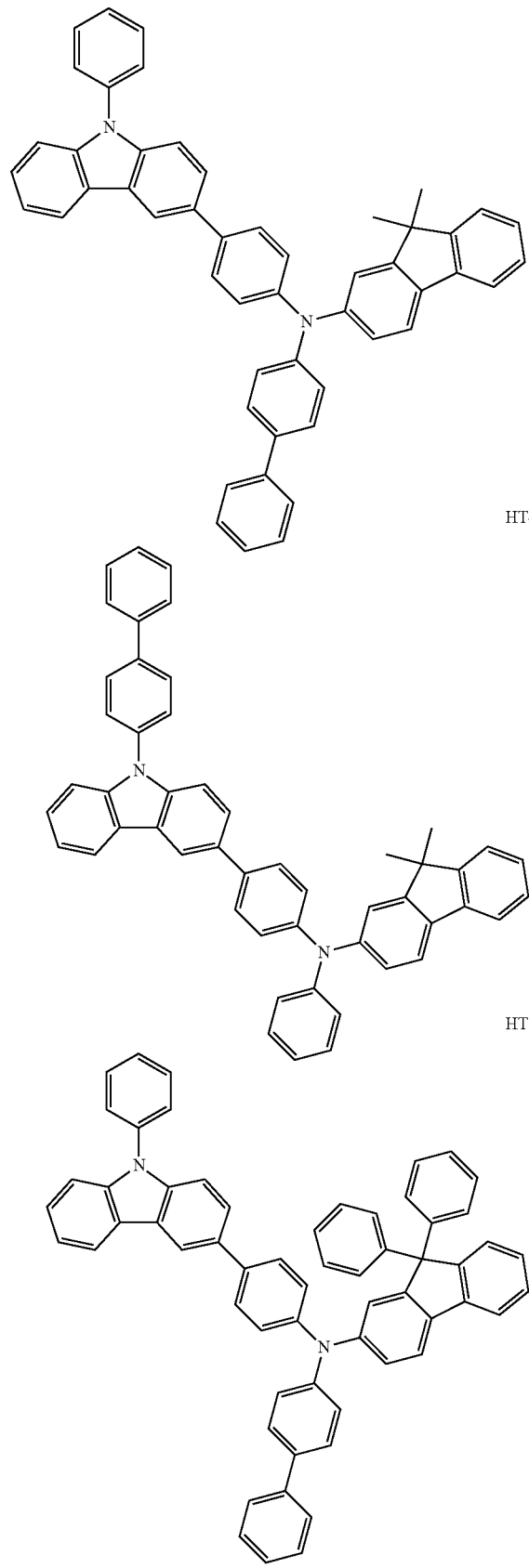
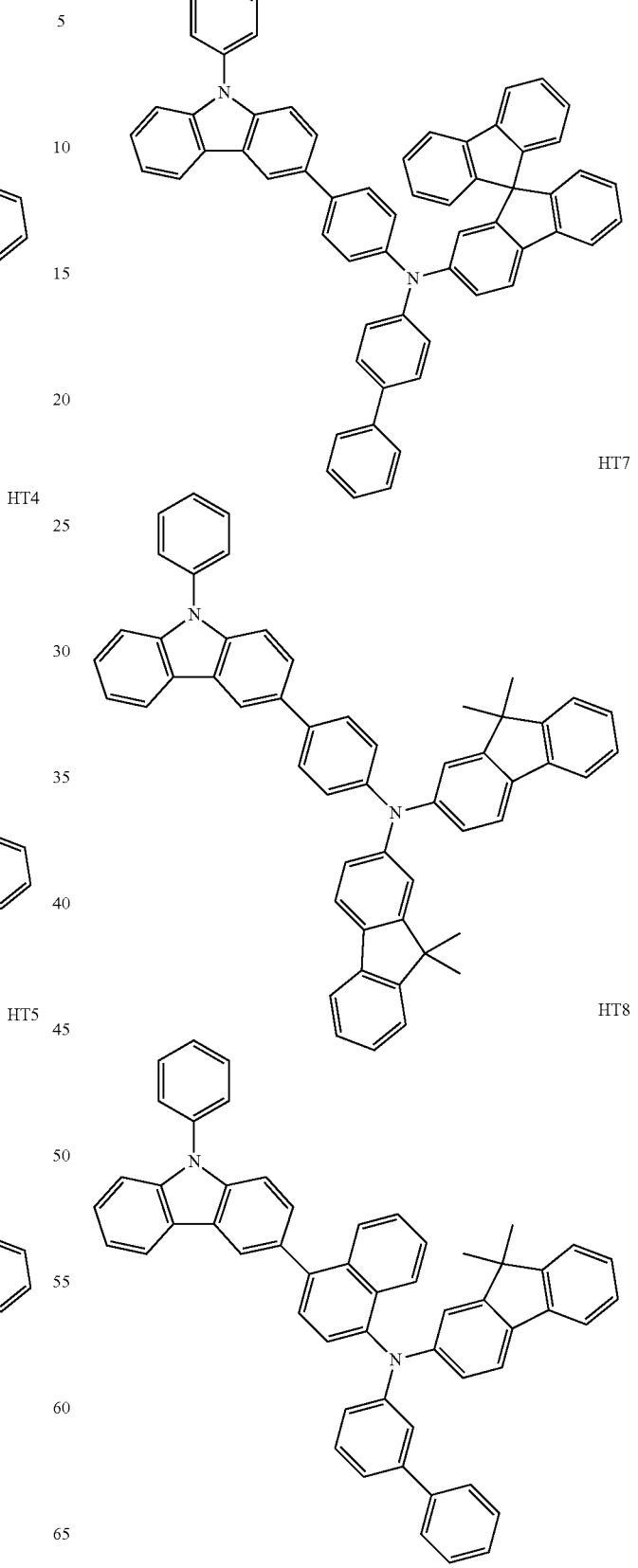

-continued
HT9
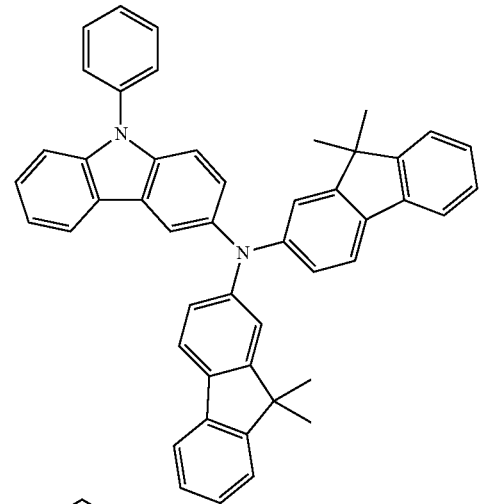
HT10
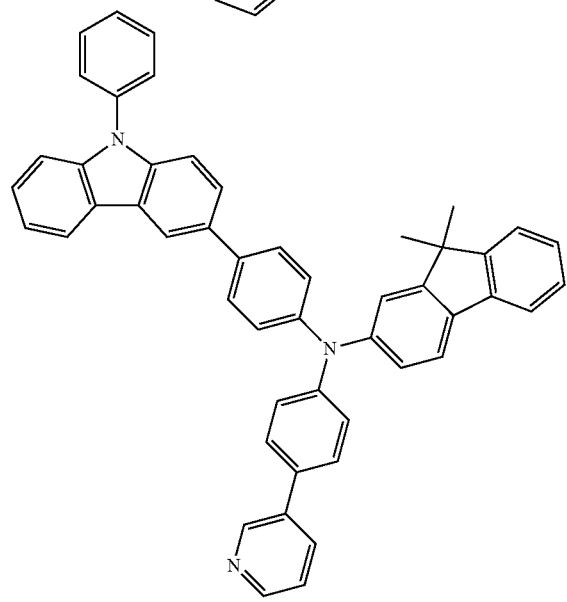
HT11
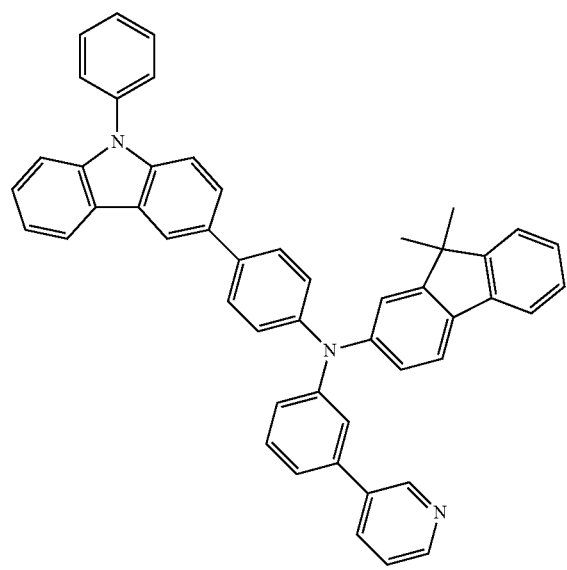
-continued
HT12
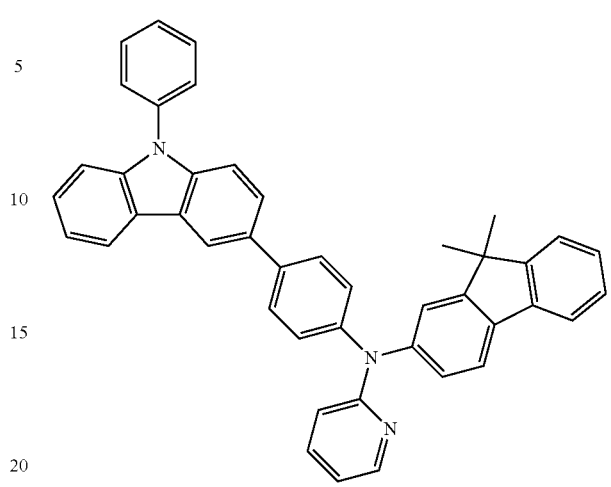
HT13
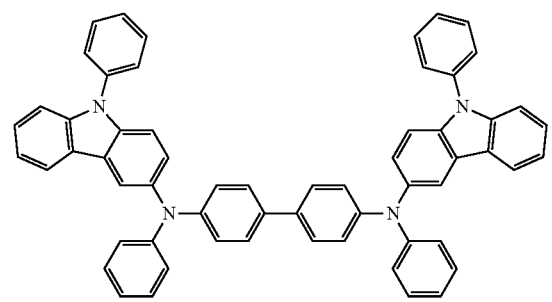
HT14
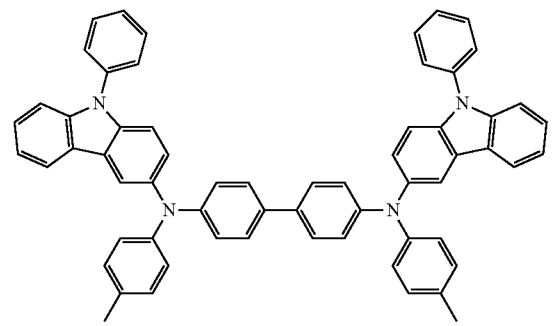
HT15
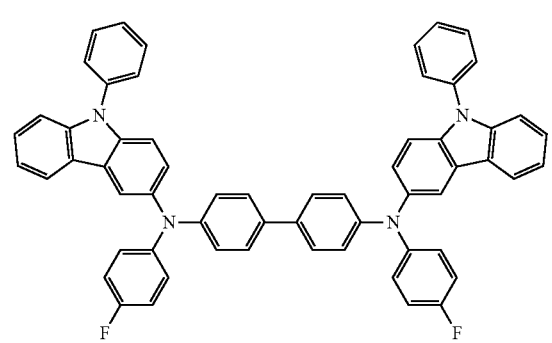

HT16

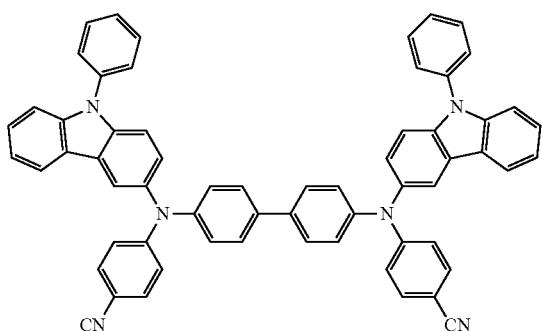

HT17

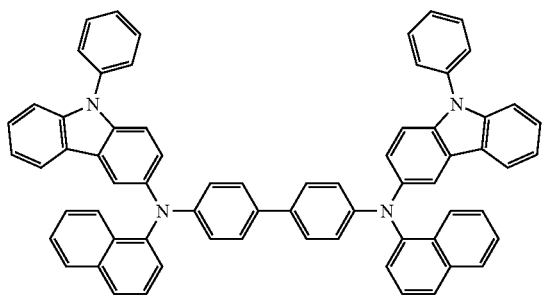

HT18

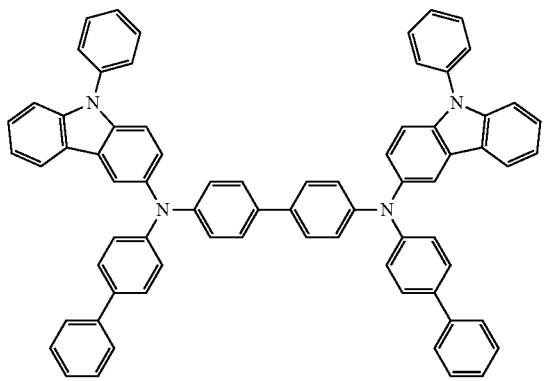

HT19

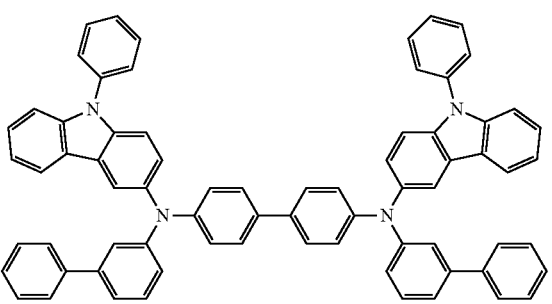

HT20

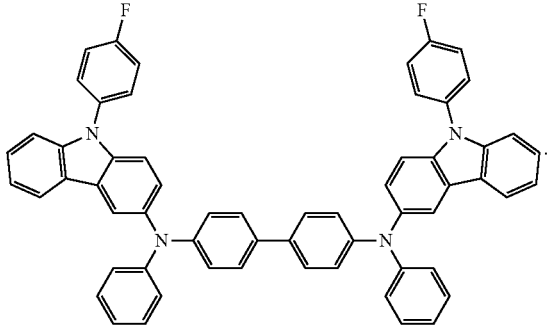

The thickness of the hole transport region may be from about 100 Å to about 10,000 Å, and in some embodiments, from about 100 Å to about 1,000 Å. When the hole transport region includes a HIL and a HTL, the thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within any of these ranges, satisfactory hole transport characteristics may be obtained without a substantial increase in driving voltage.

The hole transport region may further include a charge-generating material to improve conductivity, in addition to the materials described above. The charge-generating material may be homogeneously or inhomogeneously dispersed in the hole transport region.

The charge-generating material may be, for example, a p-dopant. The p-dopant may be selected from quinone derivatives, metal oxides, and compounds with a cyano group, but is not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-TCNQ), and/or the like; metal oxides such as tungsten oxide, molybdenum oxide, and/or the like; and Compound HT-D1 below.

Compound HT-D1

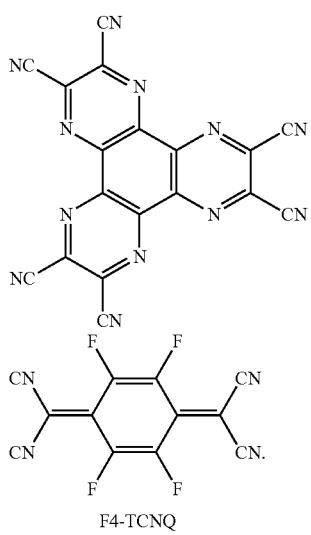

F4-TCNQ

The hole transport region may further include at least one selected from a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be any material used in the hole transport region. The EBL may block migration of electrons from the electron transport region into the EML.

The EML may be formed on the first electrode 110 or the hole transport region by using any of a variety of suitable methods, for example, by using vacuum deposition, spin coating, casting, Langmuir-Blodgett (LB) deposition, inkjet printing, laser printing, laser induced thermal imaging (LITI), and/or the like. When the EML is formed using vacuum deposition and/or spin coating, the deposition and coating conditions for forming the EML may be similar to the above-described deposition and coating conditions for forming the HIL, and accordingly will not be described in detail When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material, and thus may emit white light.

The EML may include a host and a dopant. The host may include at least one selected from the condensed cyclic compounds of Formula 1.

In some embodiments, the host may include a compound represented by Formula 301:

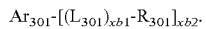

$$Ar_{301}\text{-}[(L_{301})_{xb1}\text{-}R_{301}]_{xb2}. \quad \text{Formula 301}$$

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), where $Q_{301}$ to $Q_{303}$ may be each independently selected from hydrogen, $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{301}$ may be defined the same as $L_1$ described herein;

$R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a carbazole group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group. However, embodiments of the present disclosure are not limited thereto.

For example, the host may include a compound represented by Formula 301A:

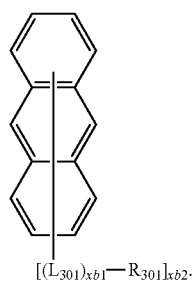

Formula 301A $[(L_{301})_{xb1}\text{—}R_{301}]_{xb2}$.

$L_{301}$, $R_{301}$, xb1, and xb2 in Formula 301A may be defined the same as those described herein.

In some embodiments, the compound of Formula 301 may be at least one selected from Compounds H1 to H42. However, embodiments of the present disclosure are not limited thereto.

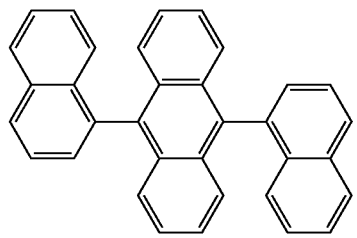

H1

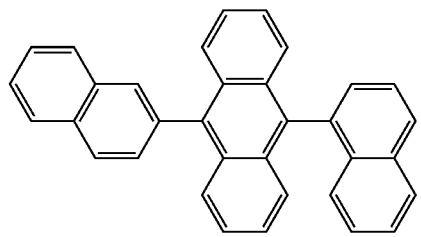

H2

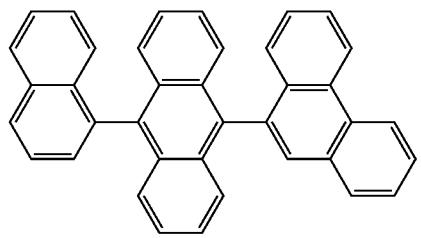

H3

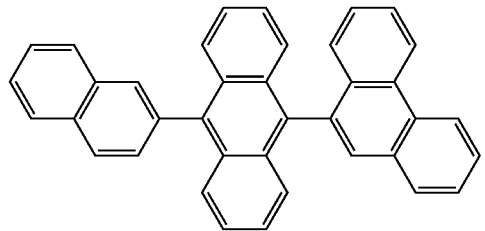

H4

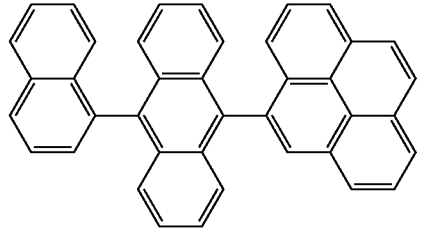

H5

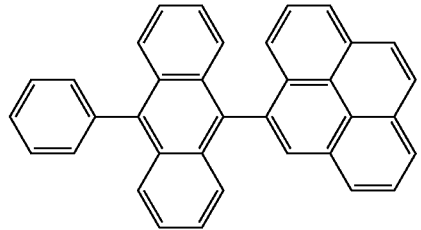

H6

-continued
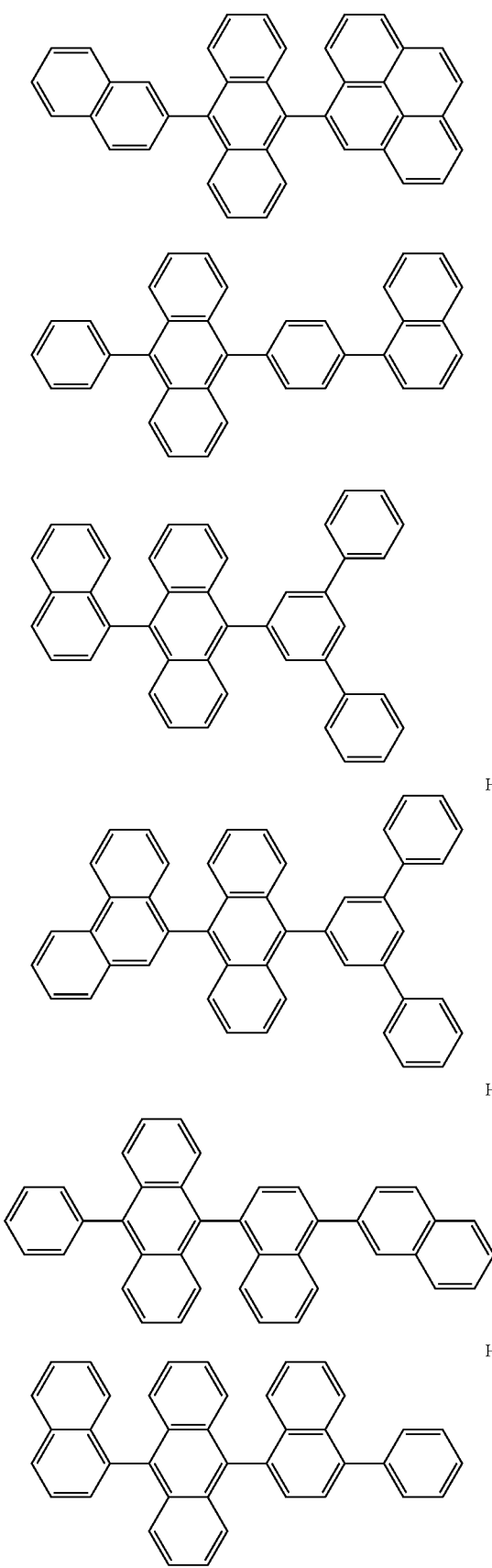
H7
H8
H9
H10
H11
H12
-continued
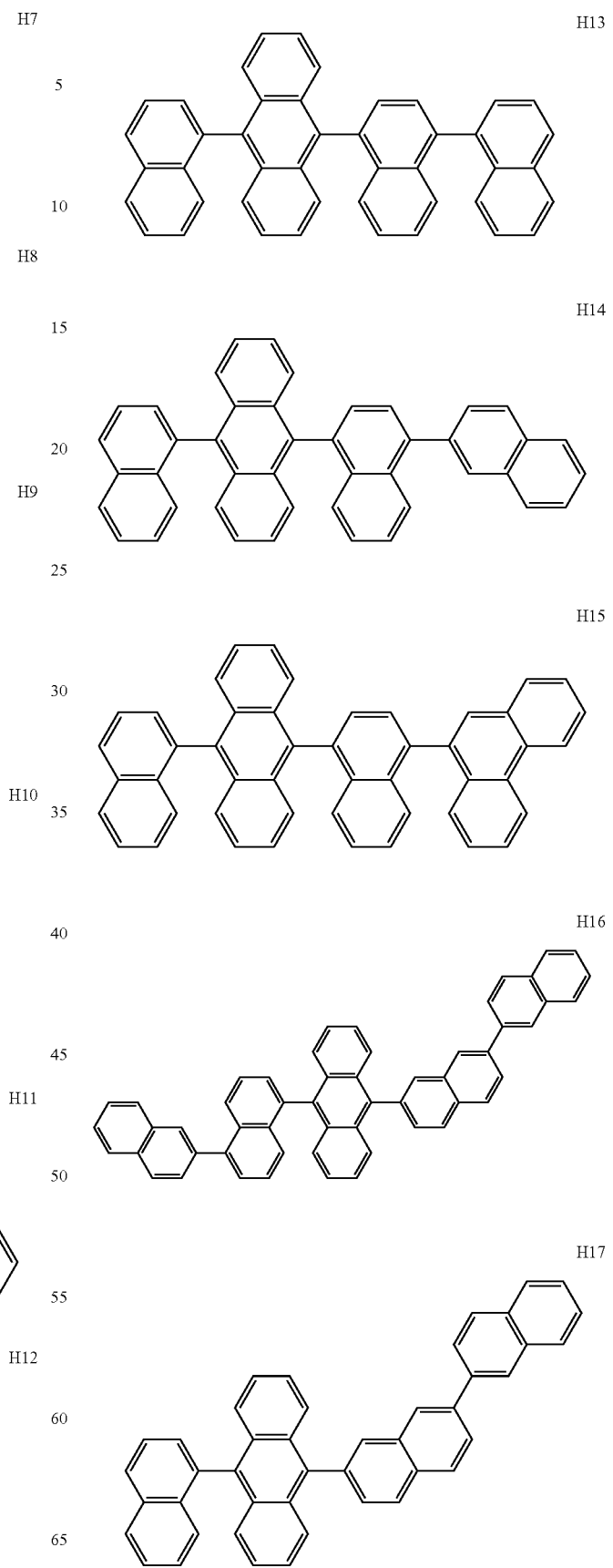
H13
H14
H15
H16
H17

H18
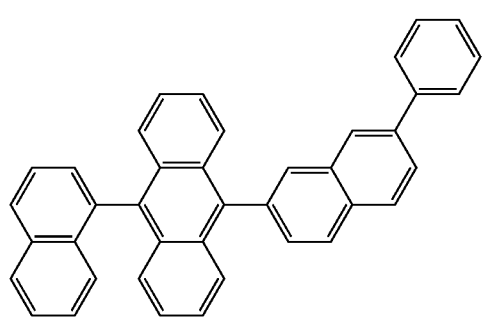
H19
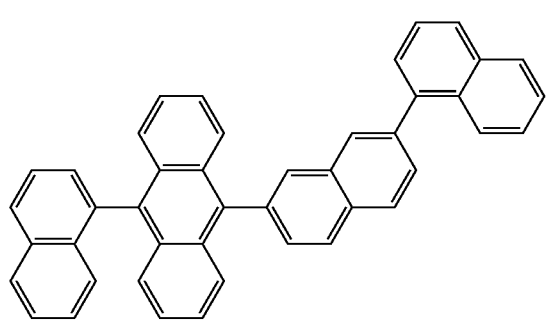
H20
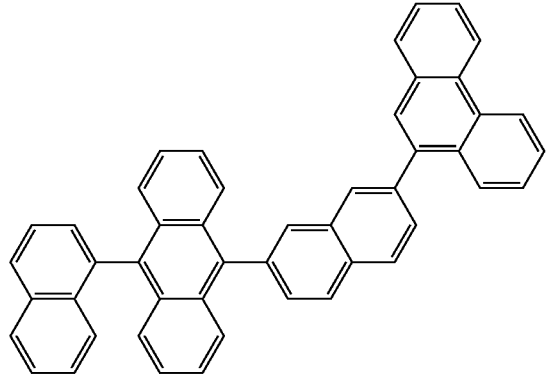
H21
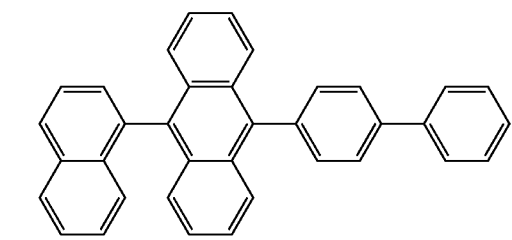
H22
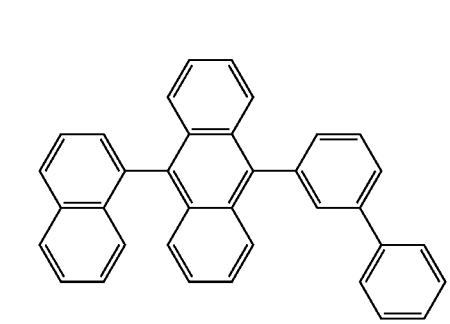
H23
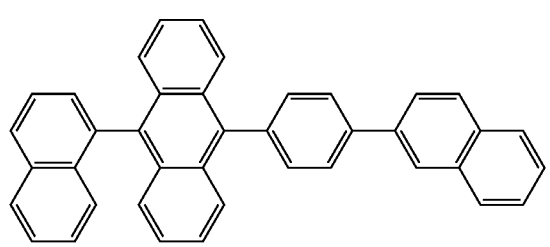
H24
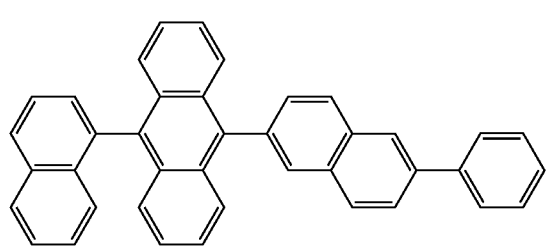
H25
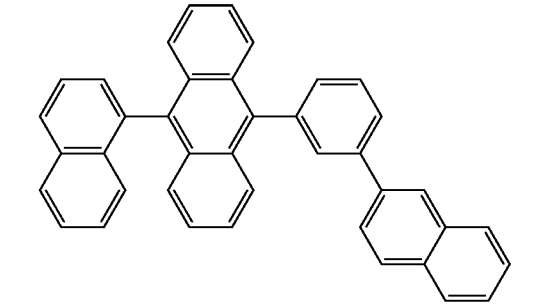
H26
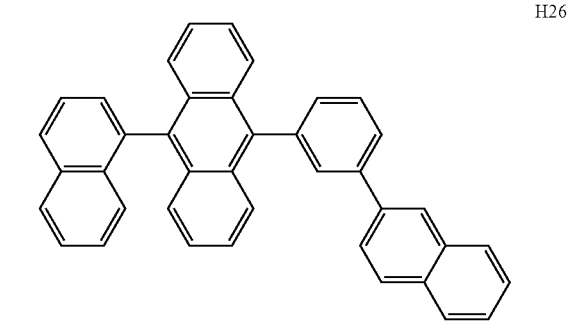
H27
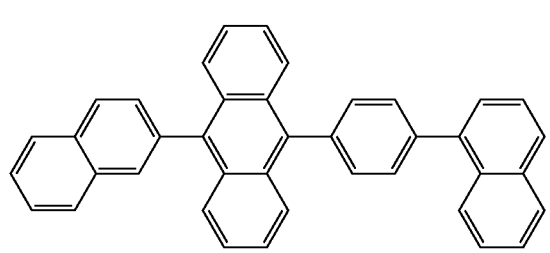

101
-continued
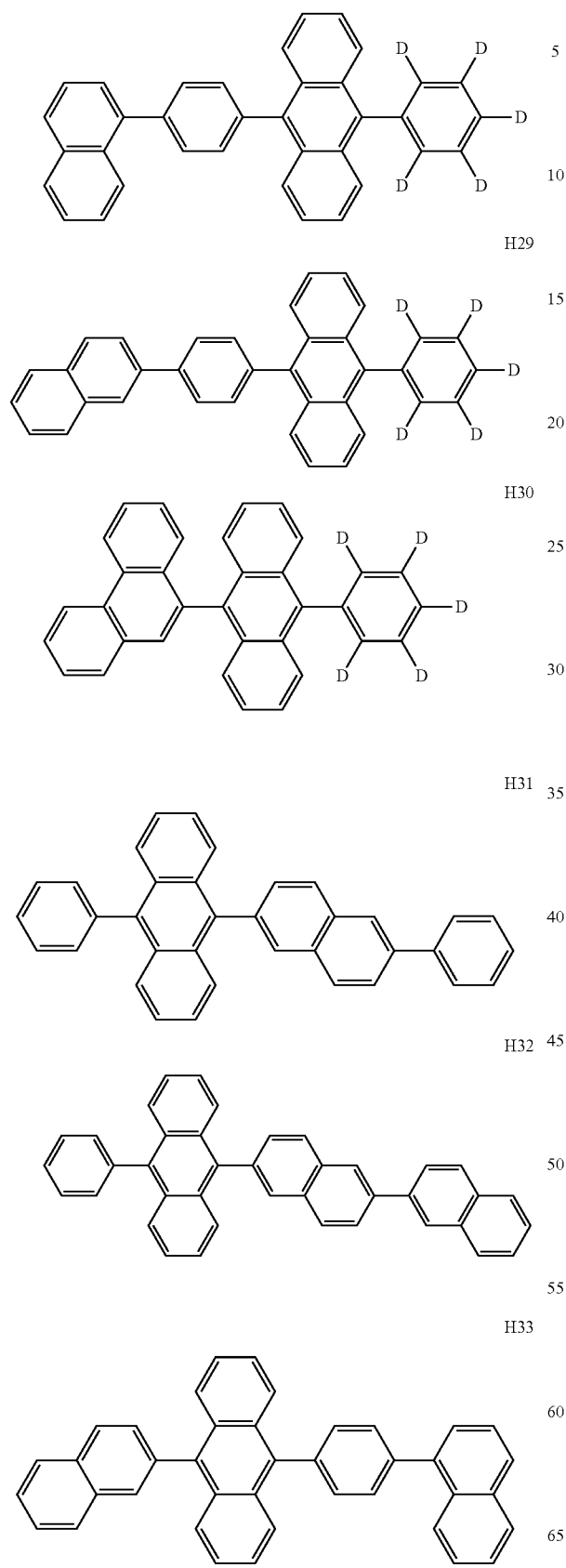
102
-continued
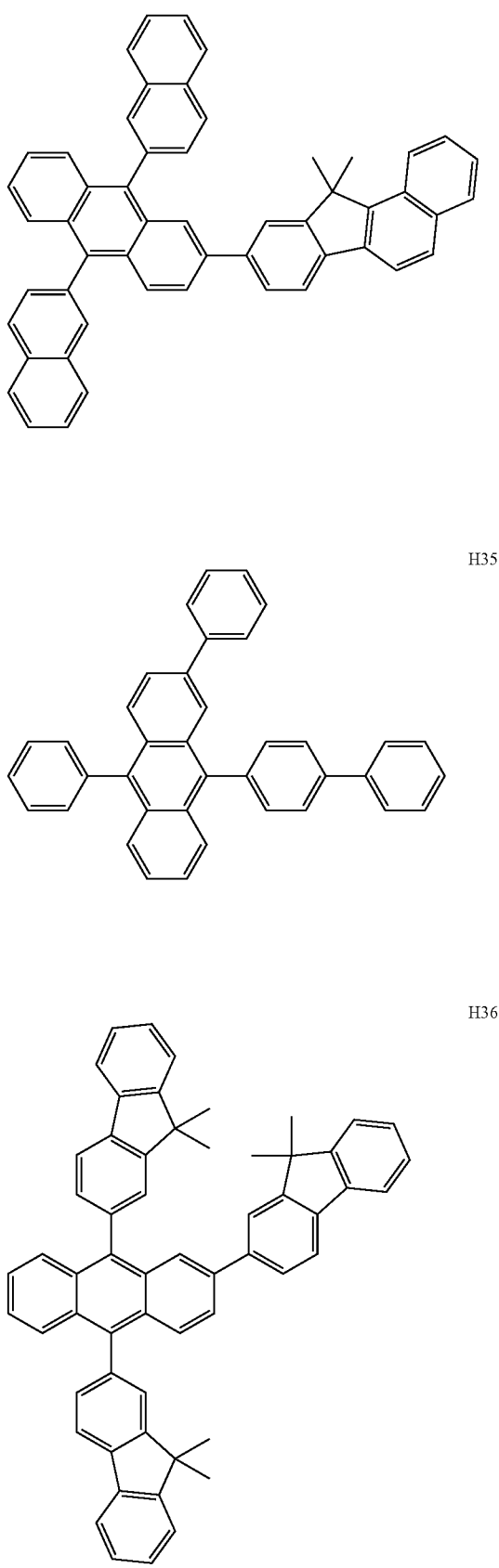

H37
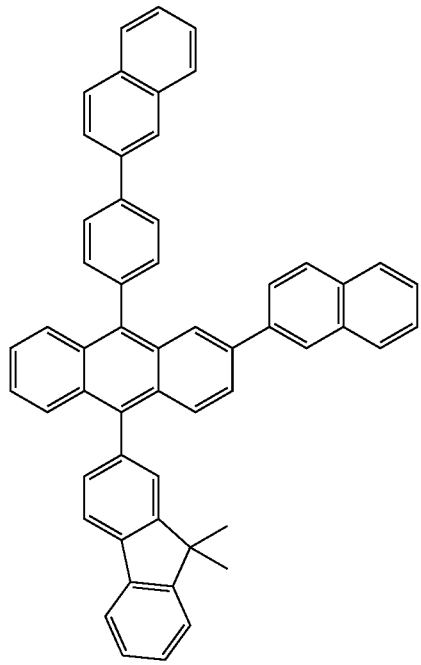
H38
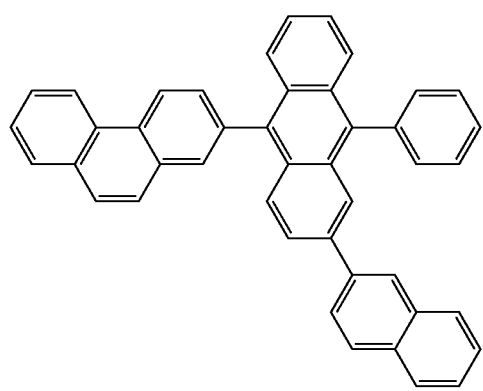
H39
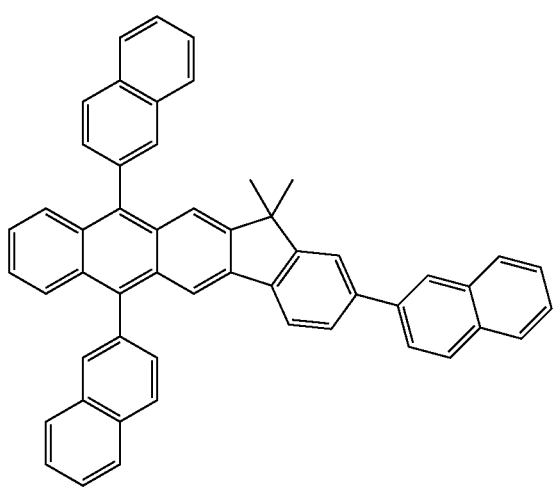
H40
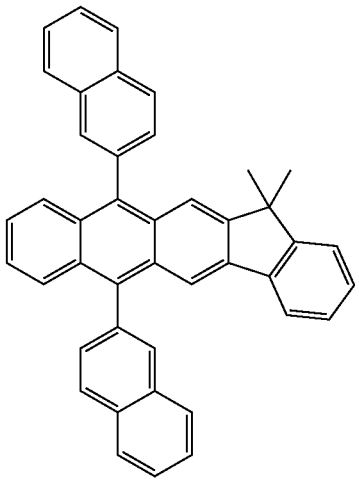
H41
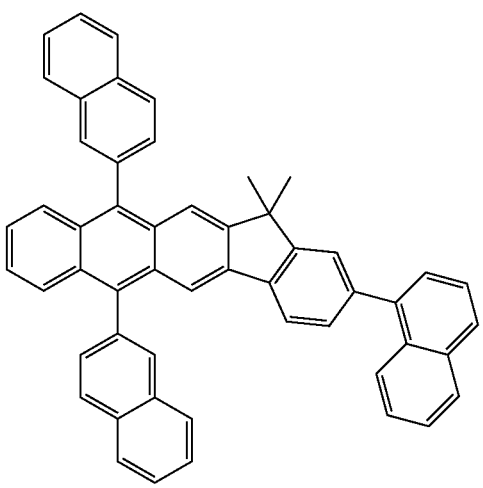
H42
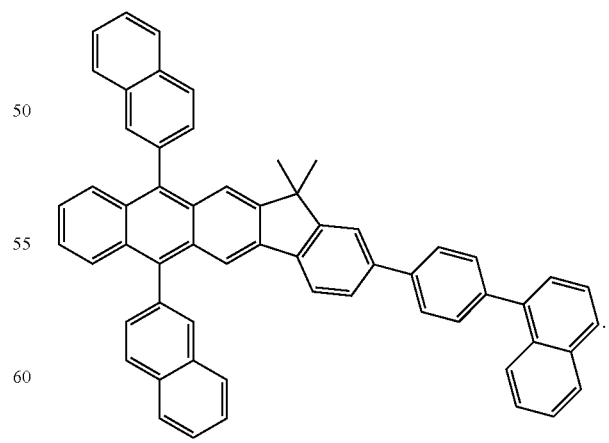
In some embodiments, the host may include at least one selected from Compounds H43 to H49. However, embodiments of the present disclosure are not limited thereto.

H43
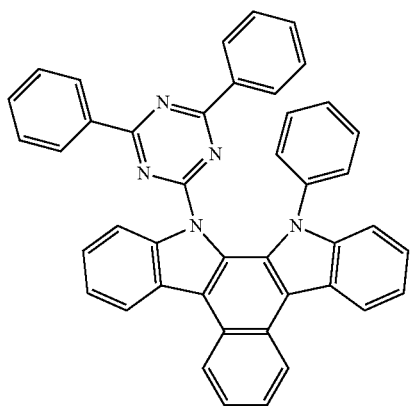
H44
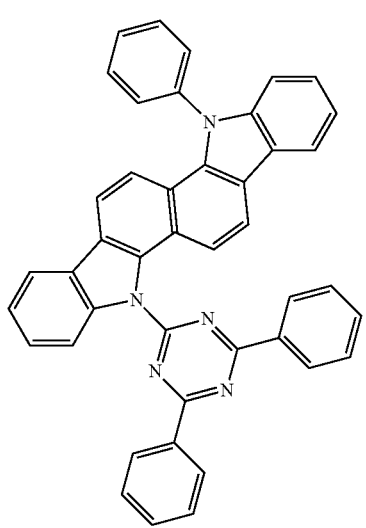
H45
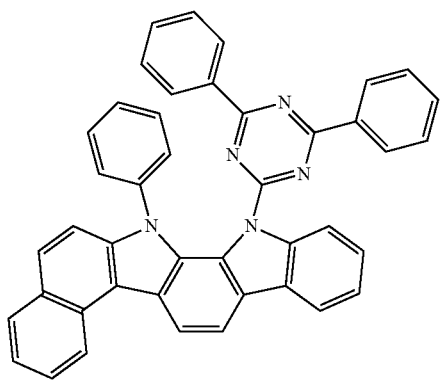
H46
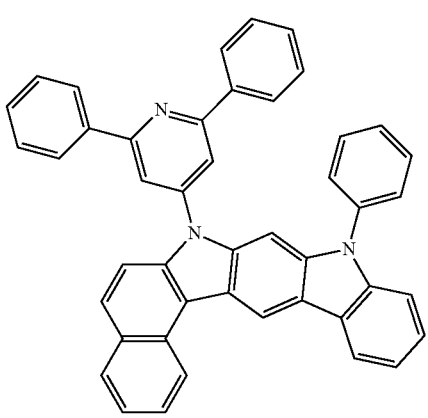
H47
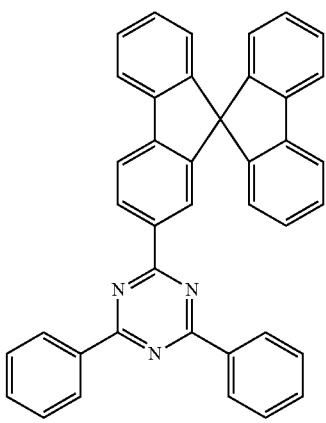
H48
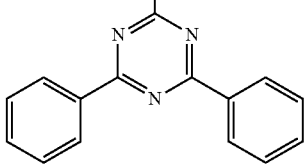
H49
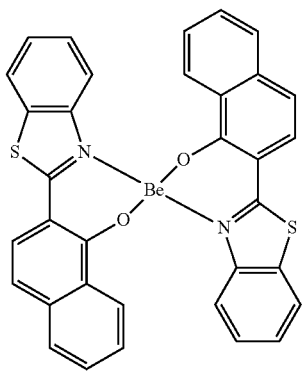
In some embodiments, the host may include one of the following compounds illustrated below. However, embodiments of the present disclosure are not limited thereto.

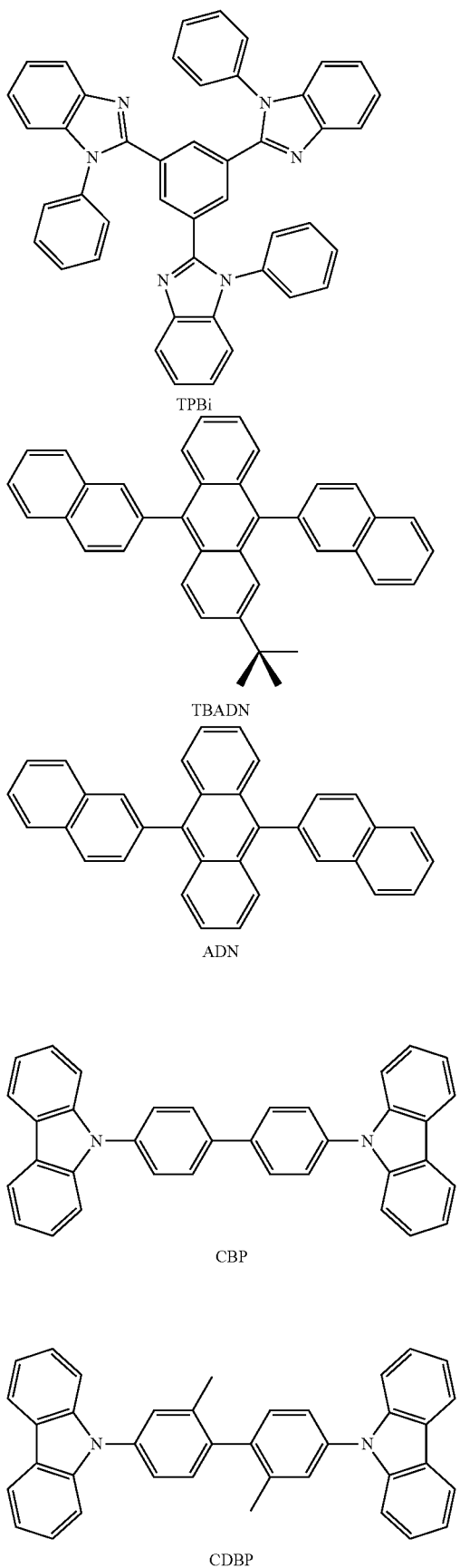

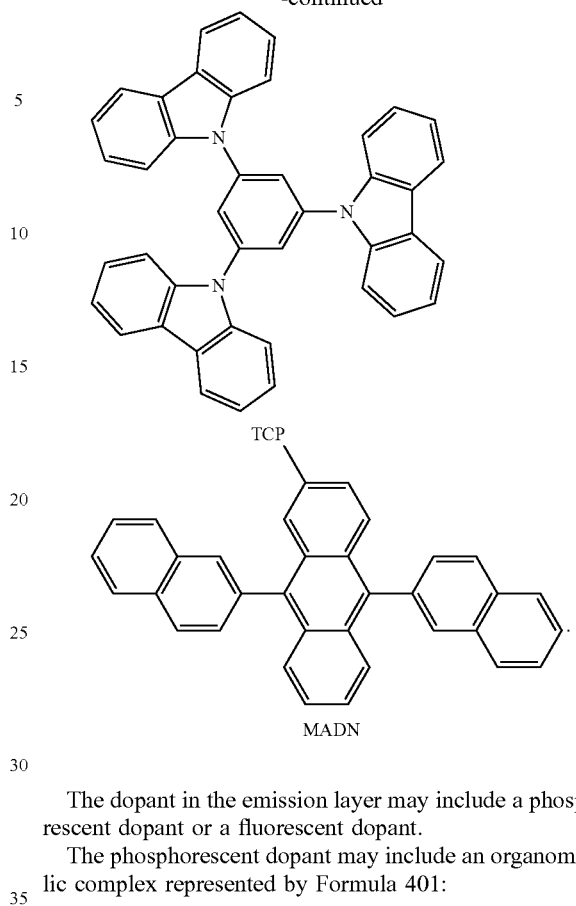

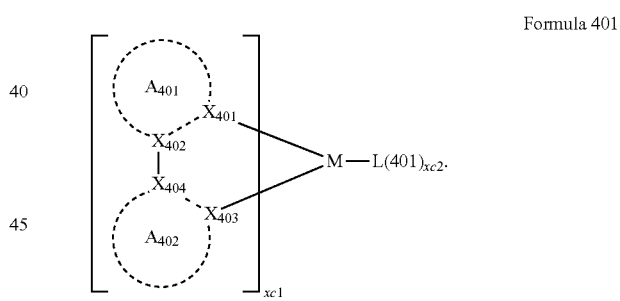

The dopant in the emission layer may include a phosphorescent dopant or a fluorescent dopant.

The phosphorescent dopant may include an organometallic complex represented by Formula 401:

Formula 401

$$\left[\begin{array}{c} A_{401} \\ X_{402} \\ X_{404} \\ A_{402} \end{array} \begin{array}{c} X_{401} \\ X_{403} \end{array} M - L(401)_{xc2}\right]_{xc1}$$

In Formula 401,

M may iridium (Ir), platinum (Pt), osmium (Os), titanium (Ti), zirconium (Zr), hafnium (Hf), europium (Eu), terbium (Tb), or thulium (Tm);

$X_{401}$ to $X_{404}$ may be each independently a nitrogen (N) or a carbon (C);

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$), and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3; and xc2 may be 0, 1, 2, or 3, where $Q_{401}$ to $Q_{407}$, $Q_{411}$ to $Q_{417}$ and $Q_{421}$ to $Q_{427}$ may be each independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group.

For example, in Formula 401, $L_{401}$ may be a monovalent, divalent, or trivalent organic ligand. For example, $L_{401}$ in Formula 401 may be selected from a halogen ligand (for example, Cl and/or F), a diketone ligand (for example, acetylacetonate, 1,3-diphenyl-1,3-propanedionate, 2,2,6,6-tetramethyl-3,5-heptanedionate, and/or hexafluoroacetonate), a carboxylic acid ligand (for example, picolinate, dimethyl-3-pyrazolecarboxylate, and/or benzoate), a carbon monoxide ligand, an isonitrile ligand, a cyano ligand, and a phosphorous ligand (for example, phosphine and/or phosphite). However, embodiments of the present disclosure are not limited thereto.

When $A_{401}$ in Formula 401 has at least two substituent groups, the at least two substituent groups of $A_{401}$ may be linked (e.g., coupled) to each other to form a saturated or unsaturated ring.

When $A_{402}$ in Formula 401 has at least two substituents groups, the at least two substituent groups of $A_{402}$ 2 may be linked (e.g., coupled) to each other to form a saturated or unsaturated ring.

When xc1 in Formula 401 is 2 or greater, a plurality of ligands in Formula 401 may be identical to or different from each other. When xc1 in Formula 1 is 2 or greater, $A_{401}$ and/or $A_{402}$ of one ligand may be respectively linked to $A_{401}$ and/or $A_{402}$ of an adjacent ligand, directly (e.g., via a chemical bond such as a single bond) or via a linking group (for example, a $C_1$-$C_5$ alkylene group, —N(R')— (where R' is a $C_1$-$C_{10}$ alkyl group or a $C_6$-$C_{20}$ aryl group), and/or C(=O)—).
The phosphorescent dopant may include at least one selected from Compounds PD1 to PD75, but is not limited thereto.
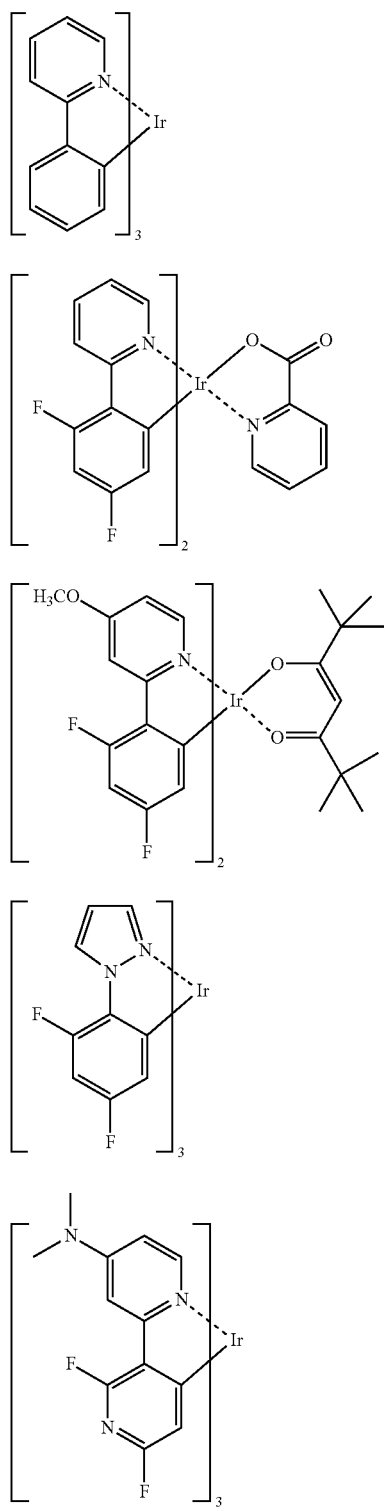
PD1
PD2
PD3
PD4
PD5
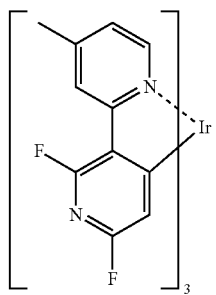
PD6
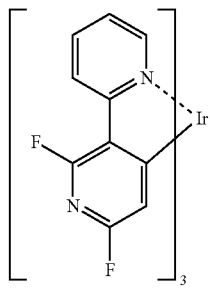
PD7
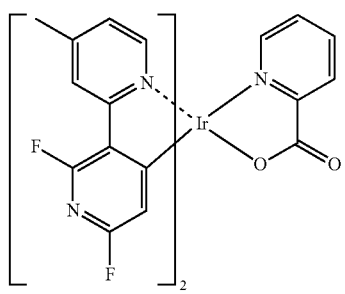
PD8
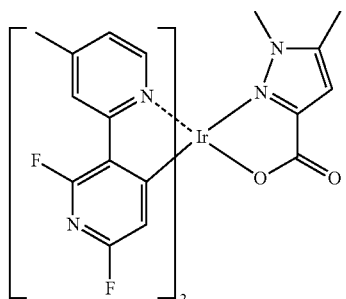
PD9
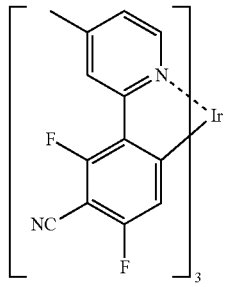
PD10

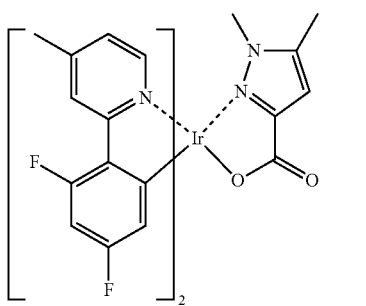
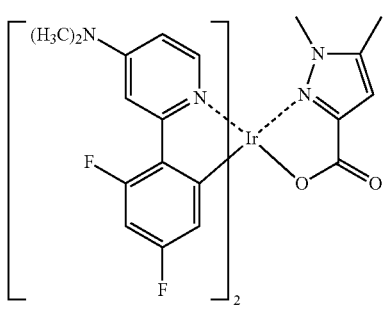
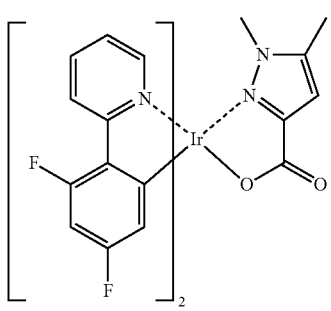
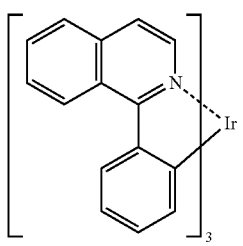
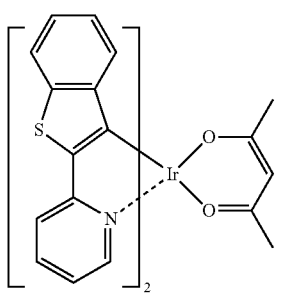
PD11
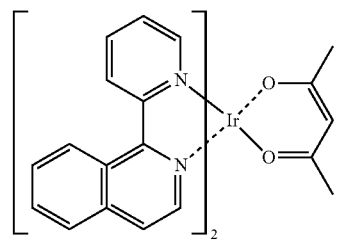
PD12
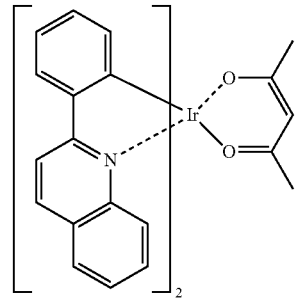
PD13
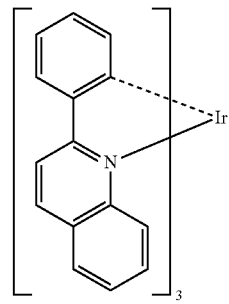
PD14
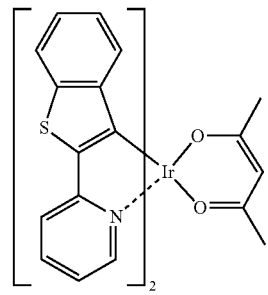
PD15
PD16
PD17
PD18
PD19
PD20
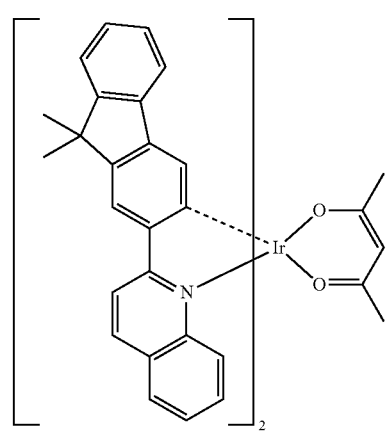

PD21 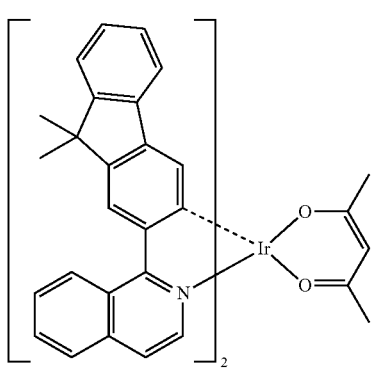
PD22 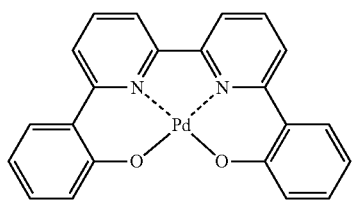
PD23 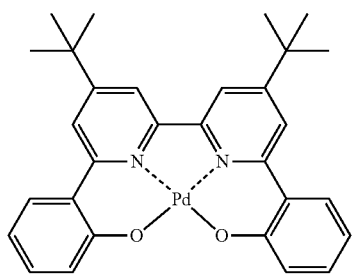
PD24 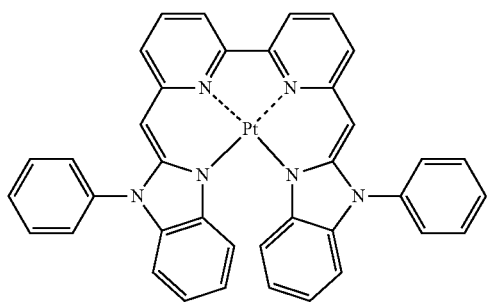
PD25 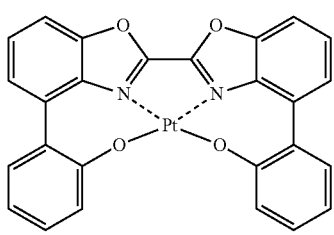
PD26 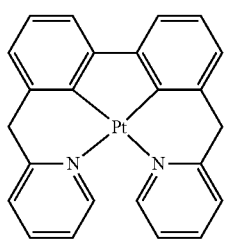
PD27 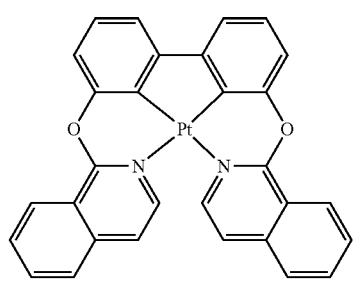
PD28 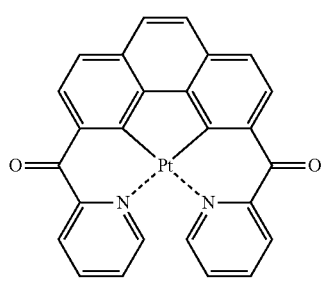
PD29 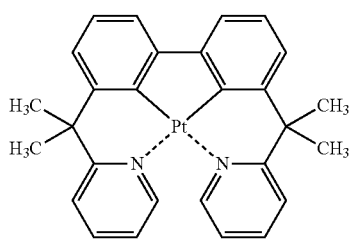
PD30 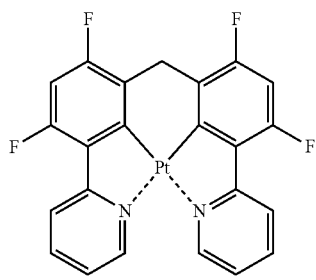
PD31 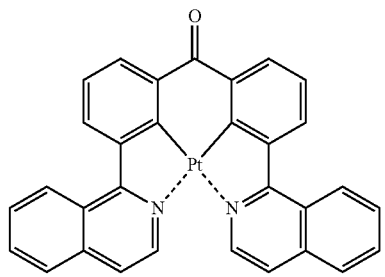
PD32 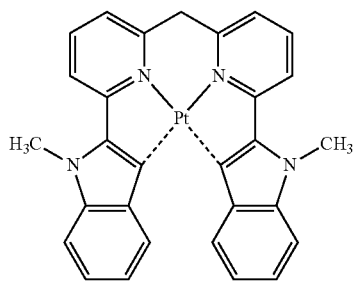

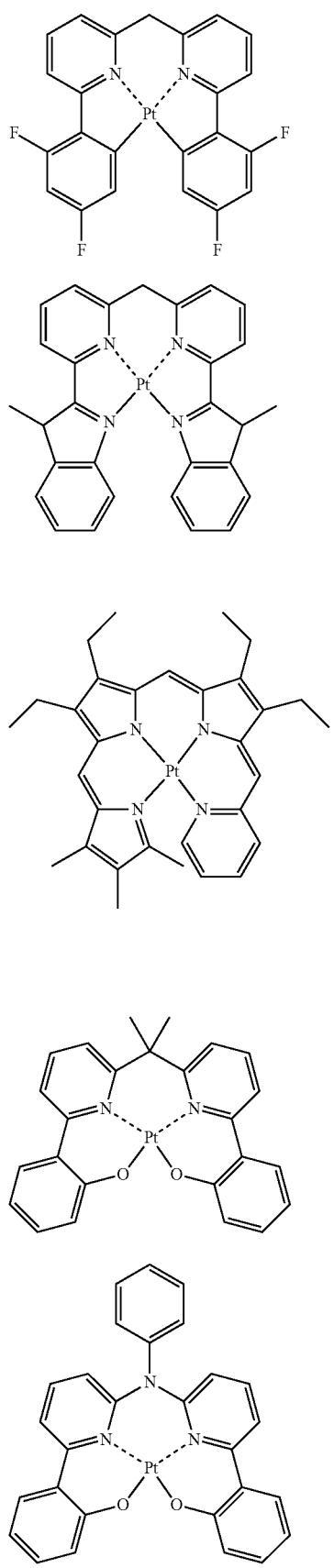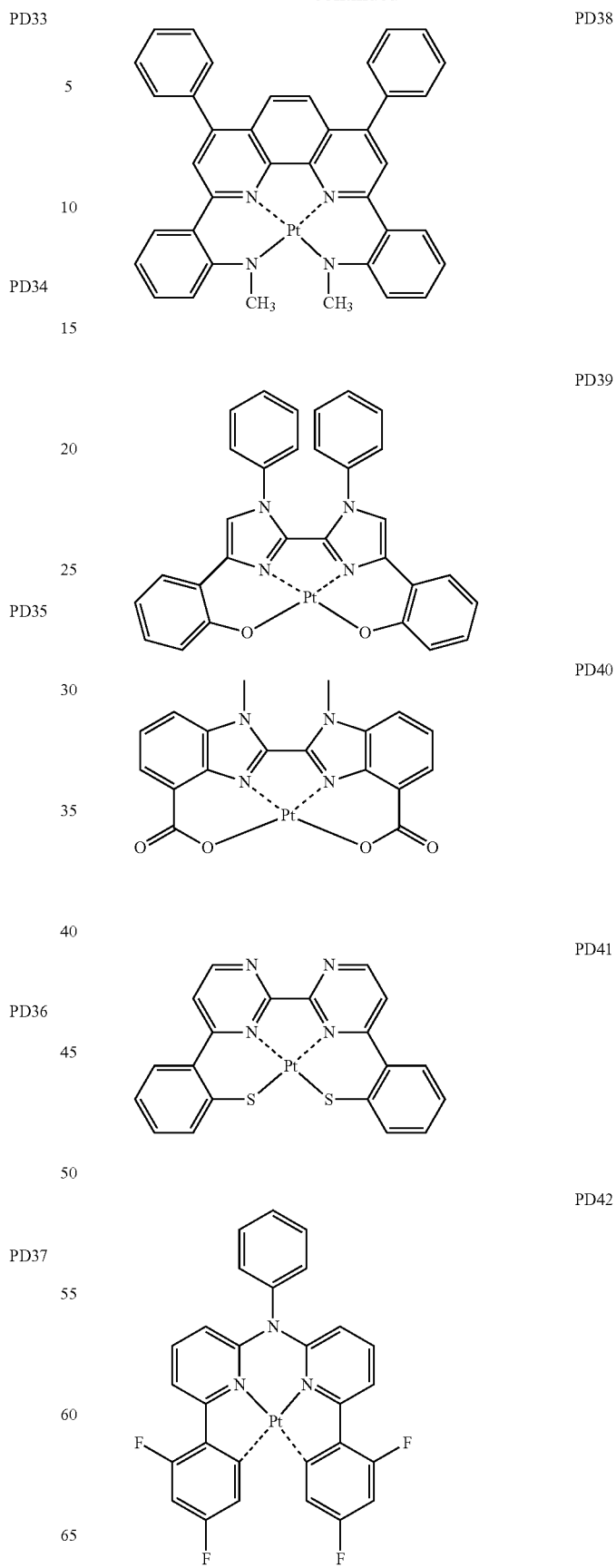

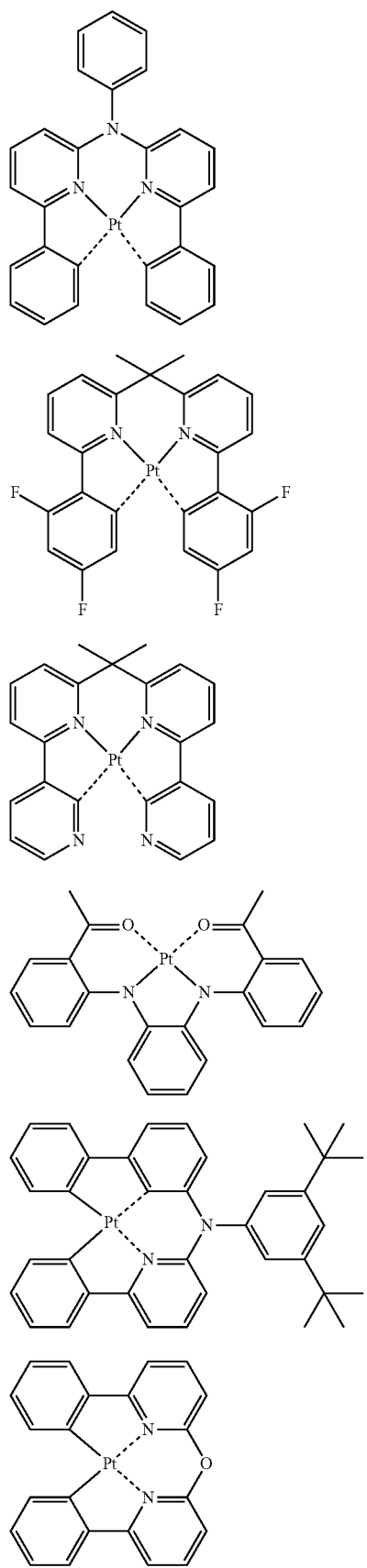
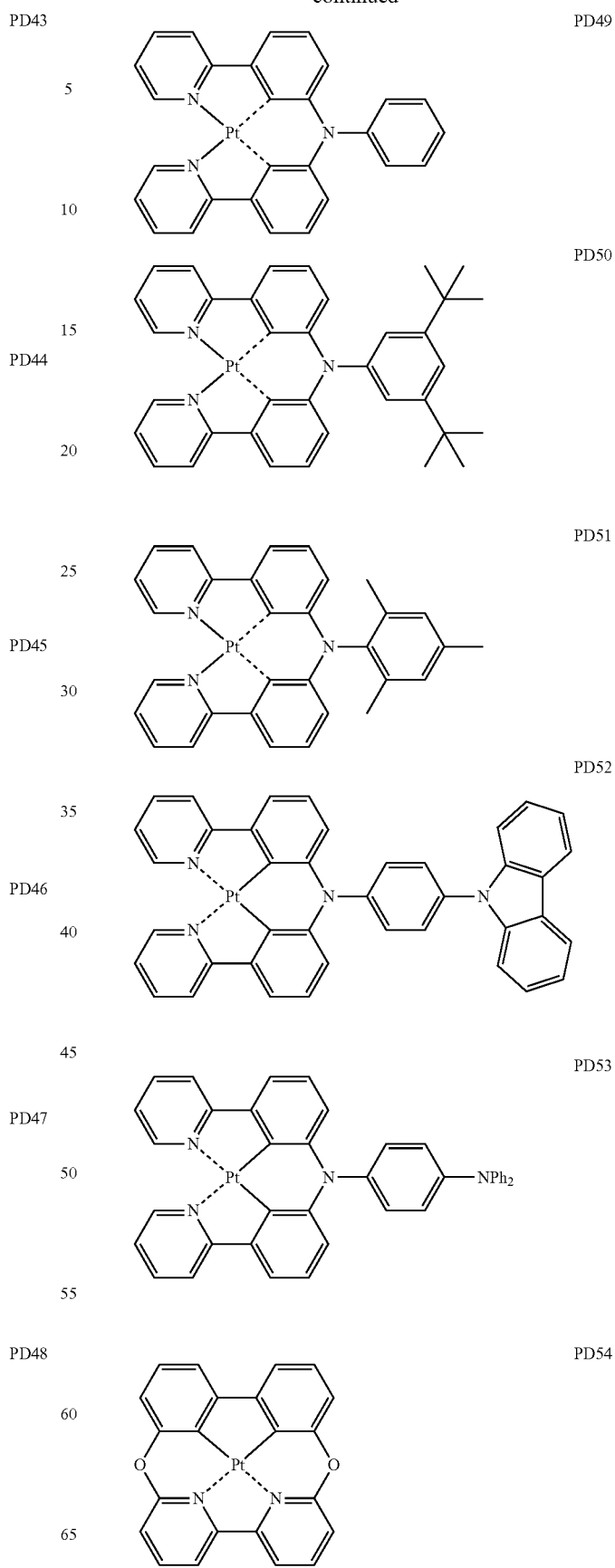

PD55
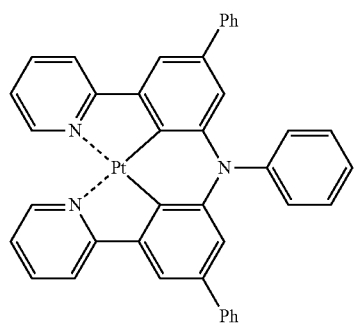
PD56
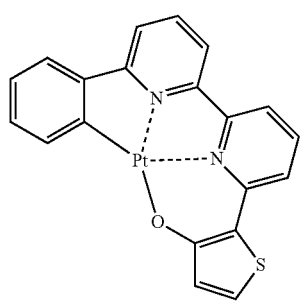
PD57
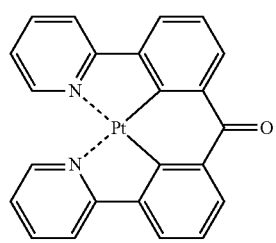
PD58
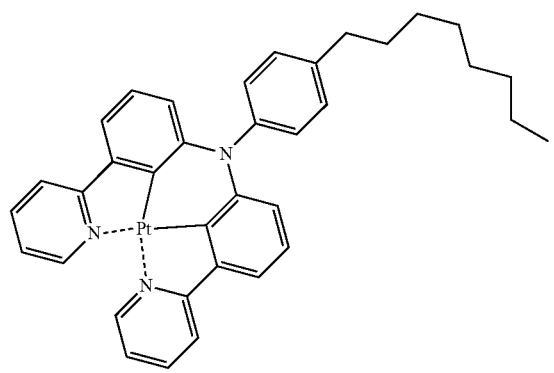
PD59
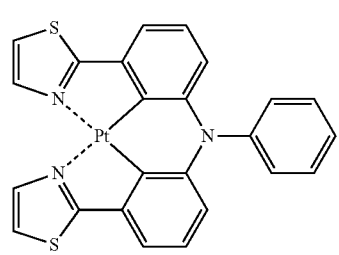
PD60
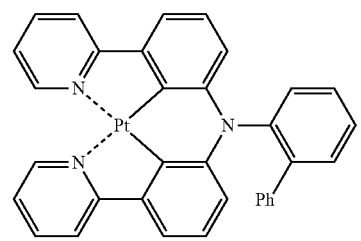
PD61
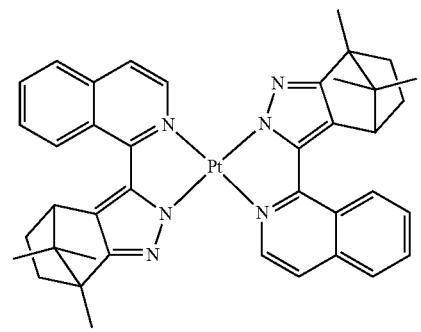
PD62
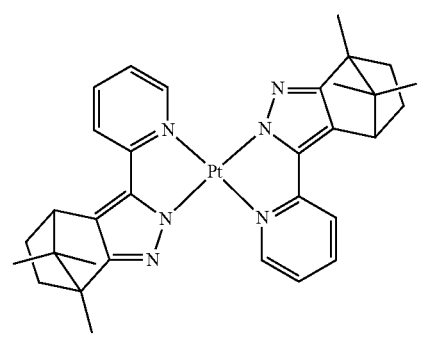
PD63
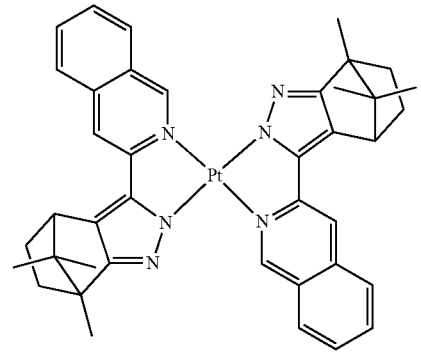
PD64
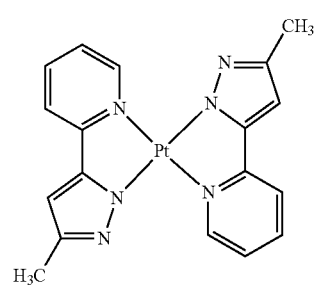

-continued
PD65
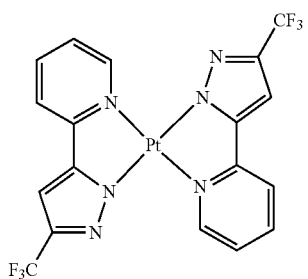
PD66
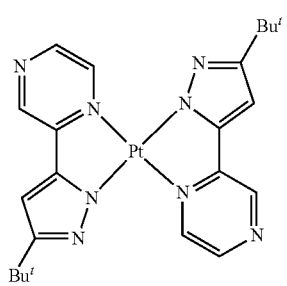
PD67
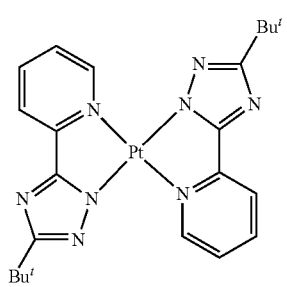
PD68
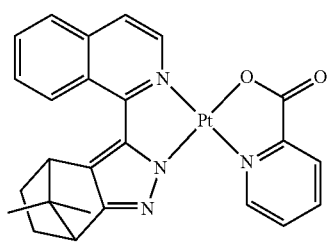
PD69
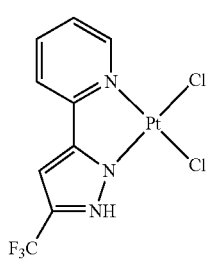
PD70
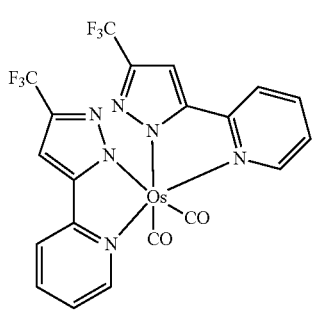
-continued
PD71
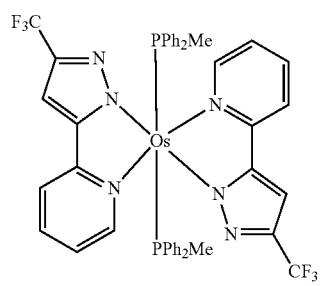
PD72
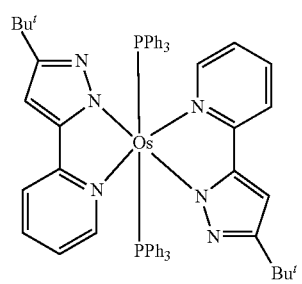
PD73
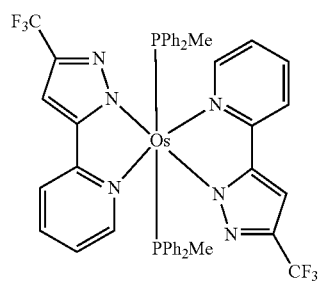
PD74
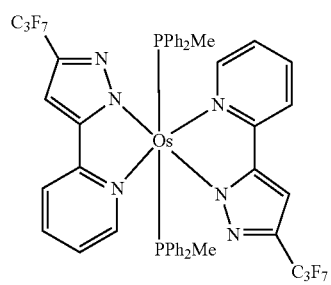
PD75
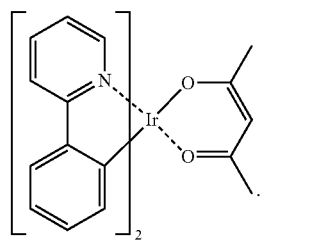
In Compounds PD1 to PD75, "Me" may refer to a methyl group, "Ph" may refer to a phenyl group, and "Bu" may refer to a tert-butyl group.

For example, the fluorescent dopant may include a compound represented by Formula 501:

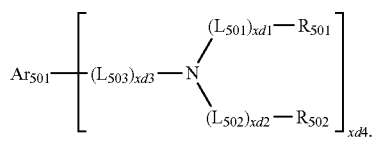

Formula 501

In Formula 501,

Ar$_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$), where $Q_{501}$ to $Q_{503}$ may be each independently selected from hydrogen, $C_1$-$C_{60}$alkyl group, a $C_2$-$C_{60}$alkenyl group, a $C_6$-$C_{60}$ aryl group, and a $C_2$-$C_{60}$ heteroaryl group;

$L_{501}$ to $L_{503}$ may be each independently defined the same as $L_1$ defined herein;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazoly group, a triazinyl group, a dibenzofuranyl group, and a dibenzothiophenyl group, and a phenyl group, a naphthyl group, a fluorenyl group, spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a phenyl group, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group;

xd1 to xd3 may be each independently selected from 0, 1, 2, and 3; and xd4 may be selected from 1, 2, 3, and 4.

For example, the fluorescent host may include at least one selected from Compounds FD1 to FD9.

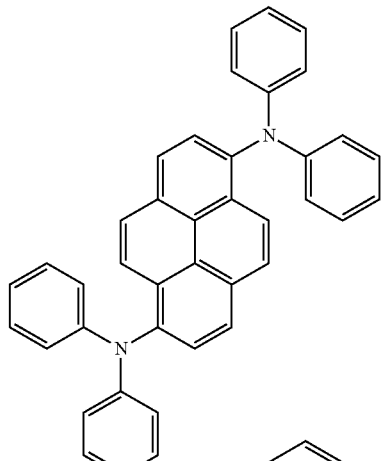

FD1

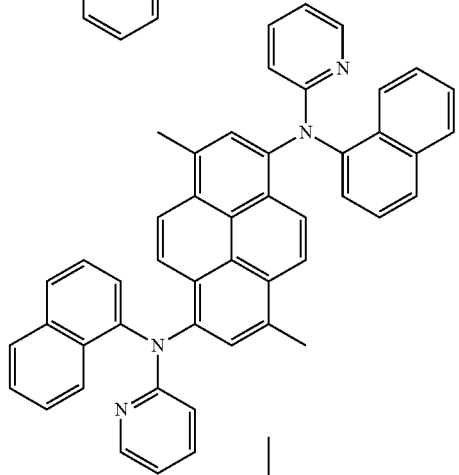

FD2

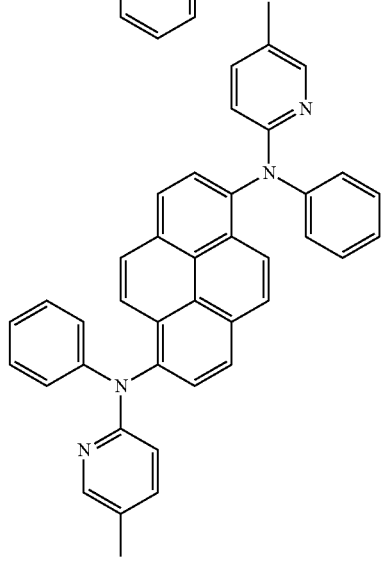

FD3

127
-continued
FD4
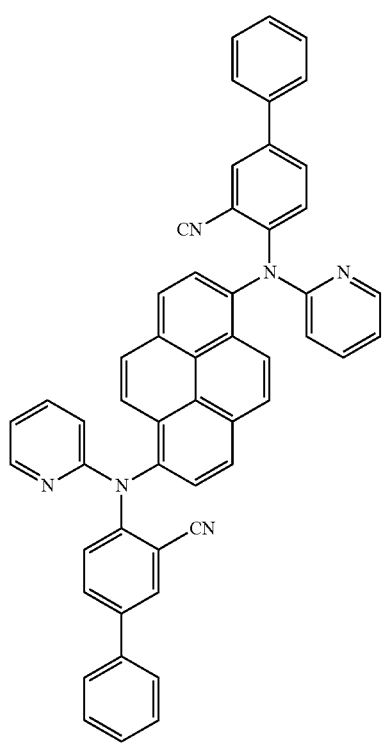
128
-continued
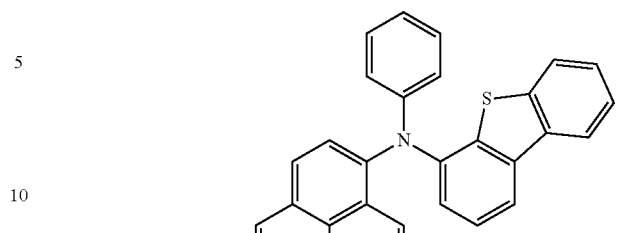
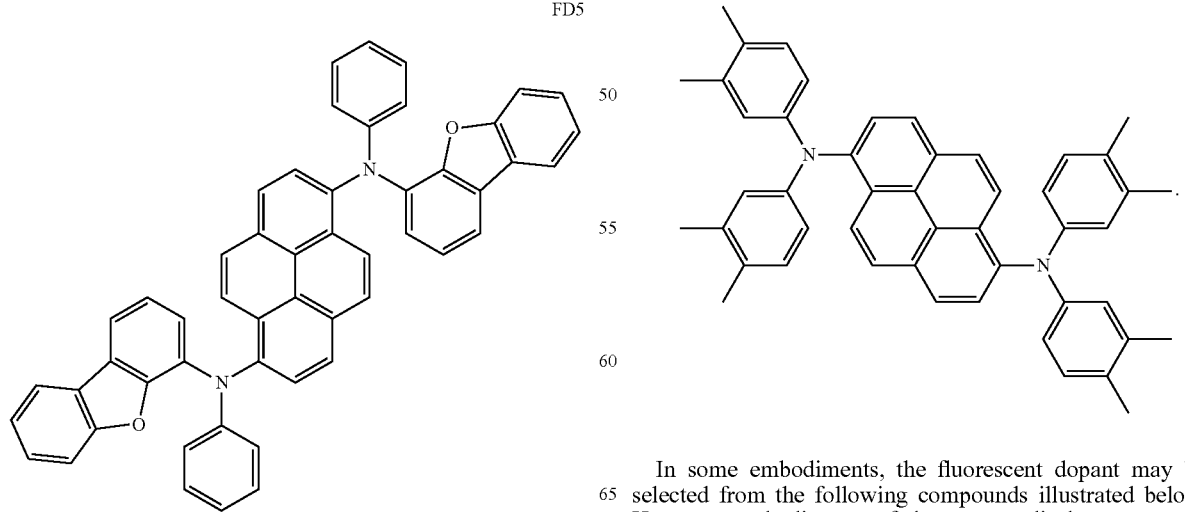
In some embodiments, the fluorescent dopant may be selected from the following compounds illustrated below. However, embodiments of the present disclosure are not limited thereto.

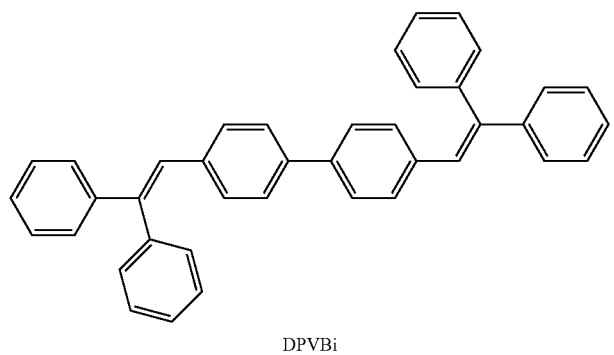
DPVBi

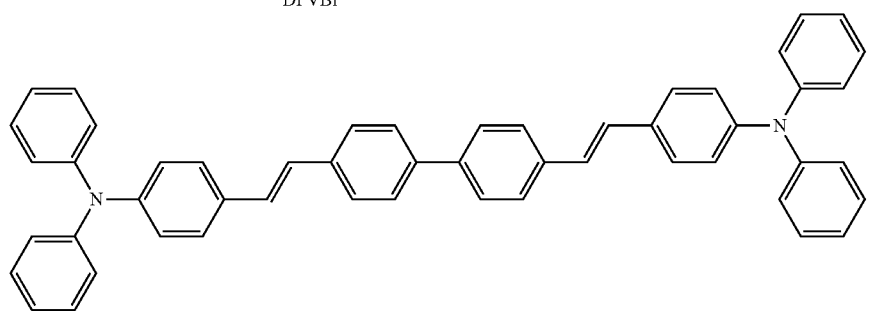
DPAVBi

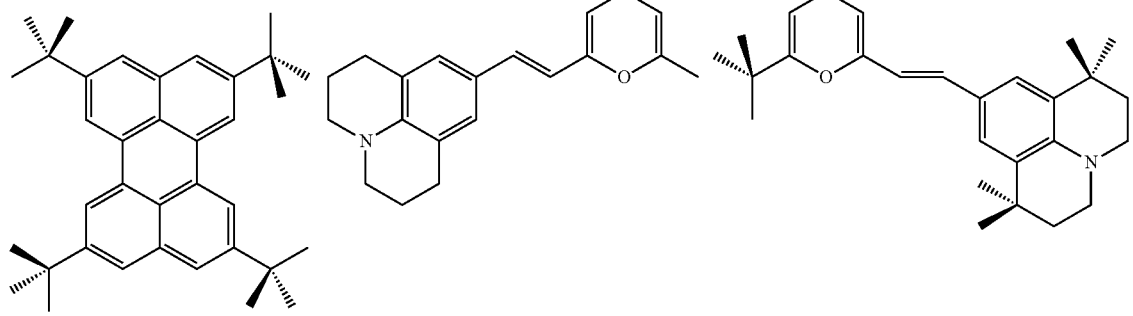

TBPe                DCM                 DCJTB

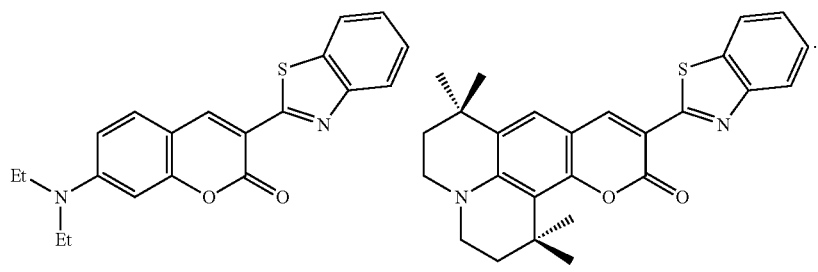

Coumarin 6            C545T

The amount of the dopant in the EML may be from about 0.01 parts to about 15 parts by weight based on 100 parts by weight of the host, but is not limited to this range.

The thickness of the EML may be about 100 Å to about 1000 Å, and in some embodiments, may be from about 200 Å to about 600 Å. When the thickness of the EML is within any of these ranges, the organic light-emitting device may have good light emitting ability without a substantial increase in driving voltage.

The electron transport region may be positioned on the EML.

The electron transport region may include at least one selected from a HBL, an ETL, and an EIL. However, embodiments of the present disclosure are not limited thereto.

In some embodiments, the electron transport region may have a structure including ETL/EIL, or a structure including HBL/ETL/EIL, wherein the layers forming the structure of the electron transport region may be sequentially stacked on the EML in the order stated above. However, embodiments of the present disclosure are not limited thereto:

In some embodiments, the organic layer 150 of the organic light-emitting device 10 may include the electron transport region between the EML and the second electrode 190.

The electron transport region may include a condensed cyclic compound of Formula 1 as described above.

The electron transport region may include a HBL. When the EML includes a phosphorescent dopant, the HBL may prevent or reduce the diffusion of triplet excitons or holes into the ETL from the EML.

When the electron transport region includes a HBL, the HBL may be formed on the EML by using any of a variety of suitable methods, for example, by using vacuum deposition, spin coating, casting, Langmuir-Blodgett (LB) deposition, inkjet printing, laser printing, laser induced thermal imaging (LITI), and/or the like. When the HBL is formed using vacuum deposition and/or spin coating, the deposition and coating conditions for forming the HBL may be similar to the above-described deposition and coating conditions for forming the HIL, and accordingly will not be described in detail.

For example, the HBL may include at least one selected from BCP and Bphen. However, embodiments of the present disclosure are not limited thereto.

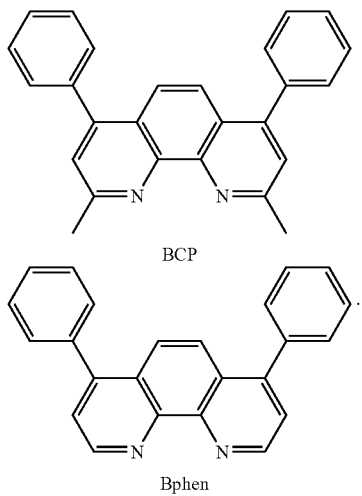

BCP

Bphen

The thickness of the HBL may be from about 20 Å to about 1,000 Å, and in some embodiments, from about 30 Å to about 300 Å. When the thickness of the HBL is within any of these ranges, the HBL may have improved hole blocking ability without a substantial increase in driving voltage.

The electron transport region may include an ETL. The ETL may be formed on the EML or the HBL by using any of a variety of suitable methods, for example, by using vacuum deposition, spin coating, casting, Langmuir-Blodgett (LB) deposition, inkjet printing, laser printing, laser induced thermal imaging (LITI), and/or the like. When the ETL is formed using vacuum deposition and/or spin coating, the deposition and coating conditions for forming the ETL may be similar to the above-described deposition and coating conditions for forming the HIL, and accordingly will not be described in detail.

The ETL may include the condensed cyclic compound of Formula 1 according to embodiments of the present disclosure.

The thickness of the ETL may be from about 100 Å to about 1,000 Å, and in some embodiments, from about 150 Å to about 500 Å. When the thickness of the ETL is within any of these ranges, the organic light-emitting device may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex include compound ET-D1 (lithium quinolate (LiQ)) and compound ET-D2 illustrated below.

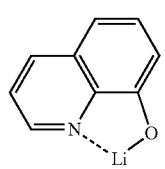

ET-D1

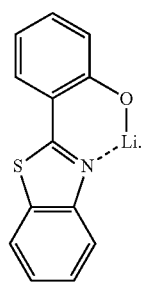

ET-D2

The electron transport region may further include an EIL that may facilitate injection of electrons from the second electrode 190.

The EIL may be formed on the ETL by using any of a variety of suitable methods, for example, by using vacuum deposition, spin coating, casting, Langmuir-Blodgett (LB) deposition, inkjet printing, laser printing, laser induced thermal imaging (LITI), and/or the like. When the EIL is formed using vacuum deposition and/or spin coating, the deposition and coating conditions for forming the EIL may be similar to the above-described deposition and coating conditions for forming the HIL, and accordingly will not be described in detail.

The EIL may include at least one selected from LiF, NaCl, CsF, Li$_2$O, BaO, and LiQ.

The thickness of the EIL may be from about 1 Å to about 100 Å, and in some embodiments, from about 3 Å to about 90 Å. When the thickness of the EIL is within any of these ranges, the EIL may have satisfactory electron injection ability without a substantial increase in driving voltage.

The second electrode 190 may be positioned on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO and/or IZO. The second electrode 190 may be a semi-transmissive electrode or a transmissive electrode.

Figure 2:
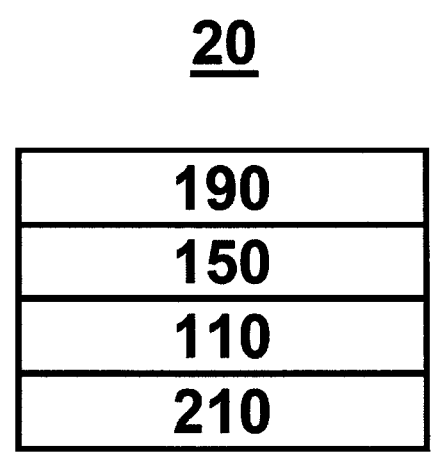
Figure 3:
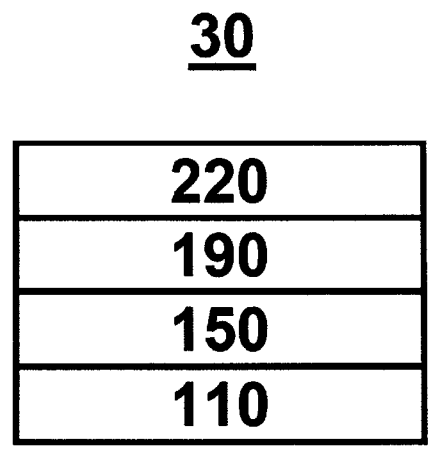
Figure 4:
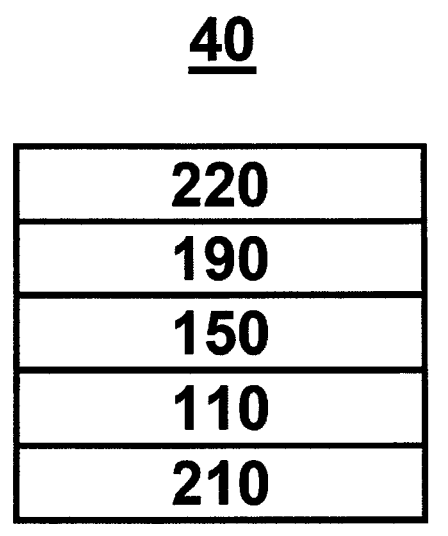

Referring to FIG. 2, an organic light-emitting device 20 according to an embodiment of the present disclosure may have a stacked structure in which a first capping layer 210, a first electrode 110, an organic layer 150, and a second electrode 190 are sequentially stacked upon one another in the stated order. Referring to FIG. 3, an organic light-emitting device 30 according to another embodiment may have a stacked structure in which a first electrode 110, an organic layer 150, a second electrode 190, and a second capping layer 220 are sequentially stacked upon one another in the stated order. Referring to FIG. 4, an organic light-emitting device 40 may have a stacked structure in which a first capping layer 210, a first electrode 110, an organic layer 150, a second electrode 190, and a second capping layer 220 are stacked upon one another in the stated order.

In FIGS. 2 to 4, the first electrode 110, the organic layer 150, and the second electrode 190 may be the same as those described above with reference to FIG. 1

In the organic light-emitting devices 20 and 40, light generated in the emission layer of the organic layer 150 may be extracted outside the organic light-emitting device through the first electrode 110 (e.g., as a semi-transmissive or transmissive electrode) and the first capping layer 210. In the organic light-emitting devices 30 and 40, light generated in the emission layer of the organic layer 150 may be extracted outside the organic light-emitting device through the second electrode 190 (e.g., as a semi-transmissive or transmissive electrode) and the second capping layer 220.

The first capping layer 210 and the second capping layer 220 may improve external emission efficiency based on the principle of constructive interference.

The first capping layer 210 of FIG. 2 and the second capping layer 220 of FIG. 3 may each include at least one selected from the condensed cyclic compounds of Formula 1.

In the organic light-emitting device of FIG. 4, at least one selected from the first capping layer 210 and the second capping layer 220 may include the at least one selected from the condensed cyclic compounds of Formula 1.

In some embodiments, in the organic light-emitting devices 20, 30, and 40 of FIGS. 2 to 4, the organic layer 150 may not include the at least one selected from the condensed cyclic compounds of Formula 1.

Although the organic light-emitting devices of FIGS. 1 to 4 have been described above, embodiments of the present disclosure are not limited thereto.

As used herein, a $C_1$-$C_{60}$ alkyl group may refer to a linear or branched aliphatic hydrocarbon monovalent group having 1 to 60 carbon atoms. Non-limiting examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl group.

As used herein, a $C_1$-$C_{60}$ alkoxy group may refer to a monovalent group represented by —$OA_{101}$ (where $A_{101}$ is the $C_1$-$C_{60}$ alkyl group as described above).

Non-limiting examples of the $C_1$-$C_{60}$ alkoxy group include a methoxy group, an ethoxy group, and an isopropyloxy group.

As used herein, a $C_2$-$C_{60}$ alkenyl group may refer to a hydrocarbon group including at least one carbon double bond at one or more positions along a carbon chain of the $C_2$-$C_{60}$ alkyl group (e.g., in the middle or at either terminal end of the $C_2$-$C_{60}$ alkyl group). Non-limiting examples of the $C_2$-$C_{60}$ alkenyl group include an ethenyl group, a propenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group may refer to a hydrocarbon group including at least one carbon triple bond at one or more positions along a carbon chain of the $C_2$-$C_{60}$ alkyl group (e.g., in the middle or at either terminal end of the $C_2$-$C_{60}$ alkyl group). Non-limiting examples of the $C_2$-$C_{60}$ alkynyl group include an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group may refer to a monovalent, monocyclic hydrocarbon group having 3 to 10 carbon atoms. Non-limiting examples of the $C_3$-$C_{10}$ cycloalkyl group include a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_1$-$C_{10}$ heterocycloalkyl group may refer to a monovalent monocyclic group having 1 to 10 carbon atoms and at least one hetero atom selected from N, O, P, and S as a ring-forming atom. Non-limiting examples of the $C_1$-$C_{10}$ heterocycloalkyl group include a tetrahydrofuranyl group and a tetrahydrothiophenyl group. A $C_1$-$C_{10}$ heterocycloalkylene group refers to a divalent group having the same structure as the $C_1$-$C_{10}$ heterocycloalkyl group.

As used herein, a $C_3$-$C_{10}$ cycloalkenyl group may refer to a monovalent monocyclic group that has 3 to 10 carbon atoms, includes at least one double bond in the ring, but does not have aromaticity. Non-limiting examples of the $C_3$-$C_{10}$ cycloalkenyl group include a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_1$-$C_{10}$ heterocycloalkenyl group used herein may refer to a monovalent monocyclic group that has 1 to 10 carbon atoms, includes at least one double bond in the ring, and in which at least one hetero atom selected from N, O, Si, P, and S is included as a ring-forming atom. Non-limiting examples of the $C_1$-$C_{10}$ heterocycloalkenyl group include a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

As used herein, a $C_6$-$C_{60}$ aryl group may refer to a monovalent, aromatic carbocyclic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include at least two rings, the rings may be fused (e.g., coupled) to each other.

As used herein, a $C_1$-$C_{60}$ heteroaryl group may refer to a monovalent, aromatic carbocyclic group having 1 to 60 carbon atoms and at least one hetero atom selected from N, O, Si, P, and S as a ring-forming atom. A $C_1$-$C_{60}$ heteroarylene group refers to a divalent, aromatic carbocyclic group having 1 to 60 carbon atoms and at least one hetero atom selected from N, O, P, and S as a ring-forming atom. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl and/or the $C_1$-$C_{60}$ heteroarylene include at least two rings, the rings may be fused (e.g., coupled) to each other.

As used herein, a $C_6$-$C_{60}$ aryloxy group may refer to a monovalent group represented by —$OA_{102}$ (where $A_{102}$ is the $C_6$-$C_{60}$ aryl group as described above), and a $C_6$-$C_{60}$ arylthio group may refer to a monovalent group represented by —$SA_{103}$ (where $A_{103}$ is the $C_6$-$C_{60}$ aryl group as described above).

As used herein, a monovalent non-aromatic condensed polycyclic group may refer to a monovalent group having at least two rings condensed to each other, in which only carbon atoms (for example, 8 to 60 carbon atoms) are exclusively included as ring-forming atoms and the entire molecule does not have overall aromaticity. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group may refer to a monovalent group having at least two rings condensed to each other, in which carbon atoms (for example, 1 to 60 carbon atoms) and at least one hetero atom selected from N, O, Si, P, and S are included as ring-forming atoms and the entire molecule does not have overall aromaticity. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group, may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$, where $Q_{11}$ to $Q_{17}$, $Q_{21}$ to $Q_{27}$, and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The acronym "Ph" used herein may refer to phenyl, the acronym "Me" used herein may refer to methyl, the acronym "Et" used herein may refer to ethyl, and the acronym "ter-Bu" or "Bu$^t$" used herein may refer to tert-butyl.

One or more embodiments of the present disclosure directed to condensed cyclic compounds, and organic light-emitting devices including the same, will now be described in more detail with reference to the following examples. However, these examples are only for illustrative purposes and are not intended to limit the scope of embodiments of the present disclosure. In the following synthesis examples, the expression "'B', instead of 'A', was used" may indicate that the amounts of 'B' and 'A' were the same in equivalent amounts.

EXAMPLES

Synthesis Example 1: Synthesis of Compound 1

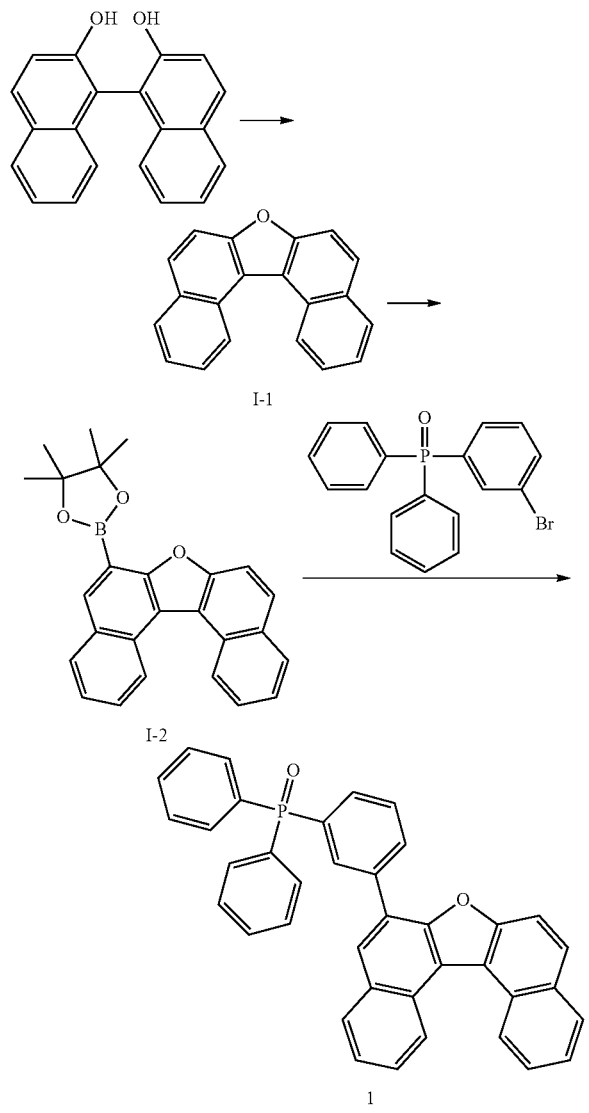

Synthesis of Intermediate I-1

5.73 g (20 mmol) of (1,1'-binaphthalene)-2,2'-diol and 4.10 g (20 mmol) of p-TsOH were dissolved in 150 mL of toluene, and then stirred at about 100° C. for about 12 hours. The resulting product was cooled down to room temperature, and an aqueous potassium carbonate solution was added thereto, followed by extraction three times with 60 mL of ethyl acetate. An organic layer was collected from the resulting product and dried using magnesium sulfate. After evaporating the solvent from the resulting product, the residue was separated and purified using silica gel column chromatography to obtain 3.76 g (Yield: 70%) of Intermediate I-1. This compound was identified using liquid chromatography-mass spectrometry (LC-MS).

$C_{20}H_{12}O$: M+1 268.3

Synthesis of Intermediate I-2

3.76 g (14 mmol) of Intermediate I-1 was dissolved in 80 mL of tetrahydrofuran (THF), and 5.6 mL of nBuLi (2.5M in Hexane) was added thereto at about −78° C. After 1 hour, 3.64 mL (18.2 mmol) of 2-isopropoxy-4,4,5,5-tetramethyl-1,3,2-dioxaborolane was added thereto at the same temperature and stirred at room temperature for about 5 hours. Water was then added thereto, followed by extraction three times with 30 mL of diethyl ether. A diethyl ether layer was collected from the resulting product, and dried using $MgSO_4$, and then under reduced pressure, the resulting residue was separated and purified using silica gel column chromatography to obtain 4.97 g (Yield: 90%) of Intermediate I-2. This compound was identified using LC-MS.

$C_{26}H_{23}BO_3$: M+1 394.3

Synthesis of Compound 1

4.97 g (12.6 mmol) of Intermediate I-2, 4.50 g (12.6 mmol) of (3-bromophenyl)-diphenylphosphine oxide, 0.73 g (0.63 mmol) of $Pd(PPh_3)_4$, and 5.22 g (37.8 mmol) of $K_2CO_3$ were dissolved in 80 mL of a mixed solution of THF and $H_2O$ (2:1 by volume) and stirred at about 80° C. for about 12 hours. The resulting product was cooled down to room temperature and extracted three times with 30 mL of water and 30 mL of ethyl acetate. An organic layer was collected and dried using magnesium sulfate. After evaporating the solvent from the resulting product, the residue was separated and purified using silica gel column chromatography to obtain 5.49 g of Compound 1 (Yield: 80%). This compound was identified using mass spectroscopy/fast atom bombardment (MS/FAB) and $^1H$ nuclear magnetic resonance spectroscopy (NMR) (results shown in Table 1).

$C_{38}H_{25}O_2P$ cal. 544.16. found 544.17.

Synthesis Example 2: Synthesis of Compound 2

5.35 g (Yield: 78%) of Compound 2 was obtained in the same (or substantially the same) manner as in Synthesis Example 1, except that (4-bromophenyl)-diphenylphosphine oxide, instead of (3-bromophenyl)-diphenylphosphine oxide used in the synthesis of Compound 1 in Synthesis Example 1, was used. This compound was identified using MS/FAB and $^1H$ NMR (results shown in Table 1).

$C_{38}H_{25}O_2P$ cal. 544.16. found 544.18.

Synthesis Example 3: Synthesis of Compound 11

4.47 g (Yield: 65%) of Compound 11 was obtained in the same (or substantially the same) manner as in Synthesis Example 1, except that (6-bromopyridine-2-yl)-diphenylphosphine oxide, instead of (3-bromophenyl)-diphenylphosphine oxide used in the synthesis of Compound 1 in Synthesis Example 1, was used. This compound was identified using MS/FAB and $^1H$ NMR (results shown in Table 1).

$C_{37}H_{24}NO_2P$ cal. 545.15. found 545.16.

Synthesis Example 4: Synthesis of Compound 23

4.09 g (Yield: 67%) of Compound 23 was obtained in the same (or substantially the same) manner as in Synthesis Example 1, except that 1-bromo-3-(phenylsulfonyl)benzene, instead of (3-bromophenyl)-diphenylphosphine oxide used in the synthesis of Compound 1 in Synthesis Example 1, was used. This compound was identified using MS/FAB and $^1H$ NMR (results shown in Table 1).

$C_{32}H_{20}O_3S$ cal. 484.11. found 484.10.

Synthesis Example 5: Synthesis of Compound 24

4.39 g (Yield: 72%) of Compound 24 was obtained in the same (or substantially the same) manner as in Synthesis Example 1, except that 1-bromo-4-(phenylsulfonyl)benzene, instead of (3-bromophenyl)-diphenylphosphine oxide used in the synthesis of Compound 1 in Synthesis Example 1, was used. This compound was identified using MS/FAB and $^1$H NMR (results shown in Table 1).

$C_{32}H_{20}O_3S$ cal. 484.11. found 484.12.

$^1$H NMR and MS/FAB data of the compounds synthesized in the above synthesis examples are shown in Table 1. Additional compounds may be synthesized using appropriate intermediate materials, according to the same (or substantially the same) synthesis method as in the synthetic pathways described above.

Synthetic pathways and source materials for synthesizing compounds not shown in Table 1 should be apparent to those of ordinary skill in the art based on the synthetic pathways and source materials in the above-described synthesis examples.

vacuum-deposited on the HIL to form a hole transport layer (HTL) having a thickness of about 300 Å.

ADN (as a host) and DPAVBi (as a dopant) were co-deposited on the HTL in a weight ratio of about 98:2 to form an emission layer (EML) having a thickness of about 300 Å.

Compound 1 was deposited on the EML to form an electron transport layer (ETL) having a thickness of about 300 Å, and then LiF was deposited on the ETL to form an electron injection layer (EIL) having a thickness of about 10 Å. Aluminum (Al) was then vacuum-deposited on the EIL to form a cathode having a thickness of about 3000 Å, thereby completing the manufacture of an organic light-emitting device.

Examples 2 to 5 and Comparative Examples 1 and 2

Organic light-emitting devices were manufactured in the same (or substantially the same) manner as in Example 1, except that compounds in Table 2, instead of Compound 1 used in Example 1, were used, respectively, to form the ETL.

TABLE 1

| Compound | $^1$H NMR (CDCl$_3$, 400 MHz) δ | MS/FAB found | calc. |
|---|---|---|---|
| 1 | 8.86-8.82 (m, 2H), 8.20-8.17 (m, 1H), 8.08-8.06 (m, 1H), 7.97-7.95 (m, 1H), 7.92-7.78 (m, 5H), 7.73 (d, 1H), 7.68-7.62 (m, 5H), 7.53-7.39 (m, 9H) | 544.17 | 544.16 |
| 2 | 8.87-8.81 (m, 2H), 7.93-7.90 (m, 3H), 7.85-7.77 (m, 7H), 7.74-7.65 (m, 5H), 7.52-7.38 (m, 8H) | 544.18 | 544.16 |
| 11 | 8.85-8.80 (m, 3H), 8.65-8.63 (m, 1H), 8.59-8.55 (m, 1H), 8.14 (d, 1H), 8.03 (dd, 1H), 7.92-7.90 (m, 2H), 7.84-7.77 (m, 6H), 7.73 (d, 1H), 7.55-7.40 (m, 8H) | 545.16 | 545.15 |
| 23 | 8.83-8.80 (m, 2H), 8.54 (t, 1H), 8.28 (d, 1H), 7.97-7.78 (m, 9H), 7.73 (d, 1H), 7.63-7.58 (m, 2H), 7.55-7.50 (m, 2H), 7.47-7.43 (m, 2H) | 484.10 | 484.11 |
| 24 | 8.85-8.81 (m, 2H), 8.33 (t, 1H), 7.97-7.88 (m, 9H), 7.84-7.78 (m, 2H), 7.72 (d, 1H), 7.59-7.55 (m, 1H), 7.52-7.43 (m, 4H) | 484.12 | 484.11 |

Example 1

A 15 Ω/cm$^2$ ITO glass substrate (having a thickness of 1200 Å, available from Corning) was cut to a size of 50 mm×50 mm×0.7 mm and then sonicated in isopropyl alcohol and deionized water each for five minutes, and then cleaned by irradiation of ultraviolet rays for 30 minutes and exposure to ozone. The resulting glass substrate with an ITO anode was mounted into a vacuum deposition device.

2-TNATA was vacuum-deposited on the ITO anode of the glass substrate to form a hole injection layer (HIL) having a thickness of 600 Å, and 4,4'-bis[N-(1-naphthyl)-N-phenylamino group]-biphenyl (hereinafter, "NPB") was then Evaluation Example 1

Driving voltages, current densities, luminances, efficiencies, and half-lifetimes of the organic light-emitting devices of Examples 1 to 5 and Comparative Examples 1 and 2 were evaluated using a Keithley Source-Measure Unit (SMU 236) and a PR650 (Spectroscan) Source Measurement Unit (available from Photo Research, Inc.). The evaluation results are shown in Table 2. A half-lifetime was measured as the time taken until a measured initial luminance (assumed as 100%) was reduced to 50%.

TABLE 2

| Example | ETL material | Driving voltage (V) | Current density (mA/cm$^2$) | Luminance (cd/m$^2$) | Efficiency (cd/A) | Emission color | Half-lifetime (hr @100 mA/cm$^2$) |
|---|---|---|---|---|---|---|---|
| Example 1 | Compound 1 | 4.35 | 50 | 3750 | 8.25 | blue | 625 |
| Example 2 | Compound 2 | 4.57 | 50 | 3800 | 7.65 | blue | 596 |
| Example 3 | Compound 11 | 4.43 | 50 | 3905 | 8.12 | blue | 553 |

TABLE 2-continued
| Example | ETL material | Driving voltage (V) | Current density (mA/cm$^2$) | Luminance (cd/m$^2$) | Efficiency (cd/A) | Emission color | Half-lifetime (hr @100 mA/cm$^2$) |
|---|---|---|---|---|---|---|---|
| Example 4 | Compound 23 | 4.01 | 50 | 3825 | 8.23 | blue | 629 |
| Example 5 | Compound 24 | 4.08 | 50 | 3655 | 8.07 | blue | 602 |
| Comparative Example 1 | Compound A | 5.32 | 50 | 3105 | 6.58 | blue | 317 |
| Comparative Example 2 | Compound B | 5.16 | 50 | 3220 | 6.62 | blue | 376 |
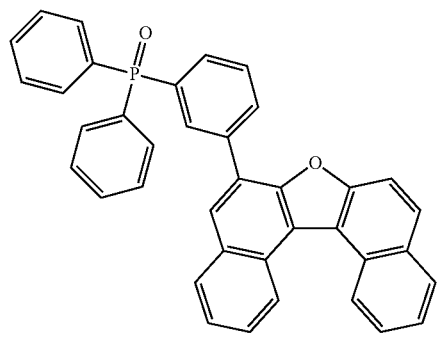
1
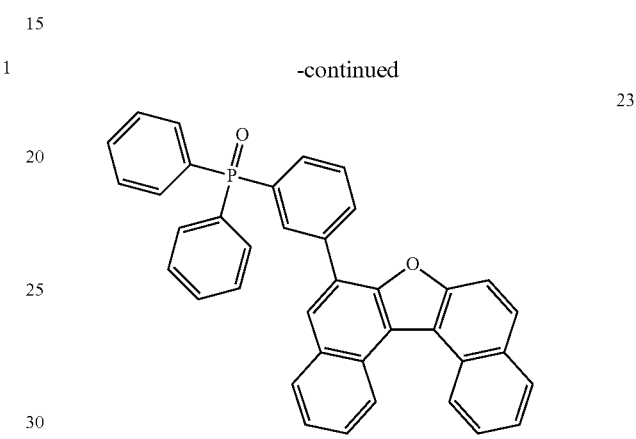
23
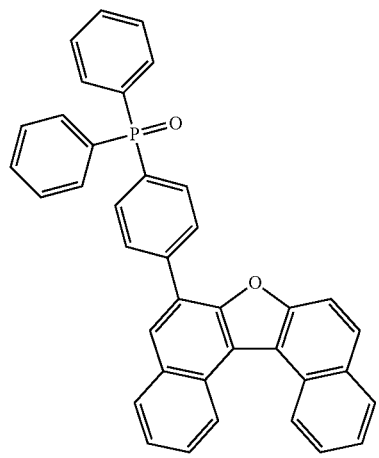
2
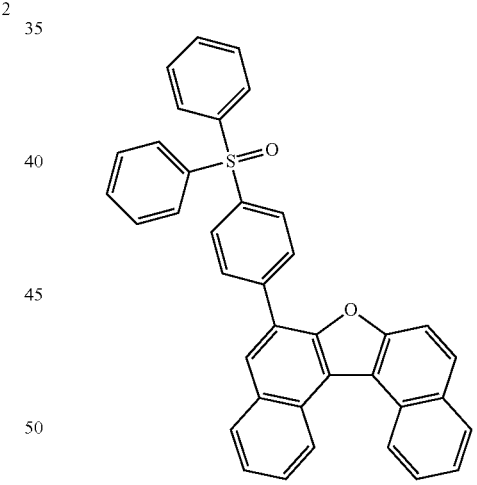
24
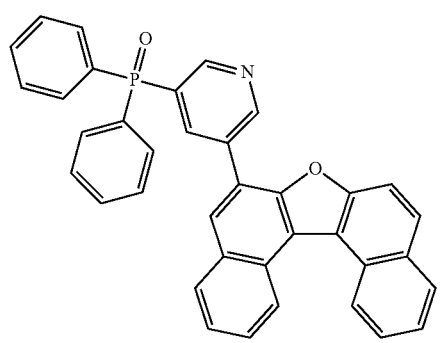
11
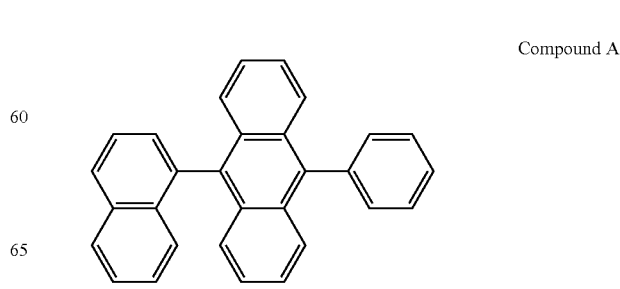
Compound A Compound B

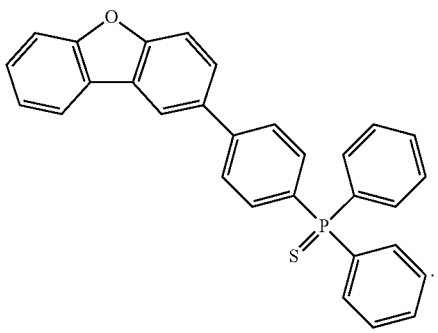

Referring to Table 1, the organic light-emitting devices of Examples 1 to 5 were found to have improved driving voltages, improved luminances, improved efficiencies, and improved half-lifetimes, as compared to those of the organic light-emitting devices of Comparative Examples 1 and 2.

As described above, according to one or more embodiments of the present disclosure, an organic light-emitting device including the condensed cyclic compound of Formula 1 may have low driving voltage, high efficiency, high luminance, and a long lifetime.

As used herein, the terms "use," "using," and "used" may be considered synonymous with the terms "utilize," "utilizing," and "utilized," respectively.

In addition, the terms "substantially," "about," and similar terms are used herein as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

It will be understood that the terms, such as "comprises," "comprising," "includes", and/or "including", when used in this specification, specify the presence of stated features, integers, steps, operations, elements, and/or components, but do not preclude the presence or addition of one or more other features, integers, steps, operations, elements, components, and/or groups thereof.

It should further be understood that the example embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims and equivalents thereof.

What is claimed is:

1. A condensed cyclic compound represented by Formula 1:

$$A_2\text{-}(A_1)_{n1},\qquad \text{Formula 1}$$

wherein, in Formula 1, $A_2$ is selected from groups represented by Formulae 2B to 2E;

$A_1$ is selected from groups represented by Formulae 2-2 to 2-4; and n1 is an integer selected from 1 to 5, wherein, when n1 is 2 or greater, at least two $A_1$s are the same as or different from each other:

Formula 2B

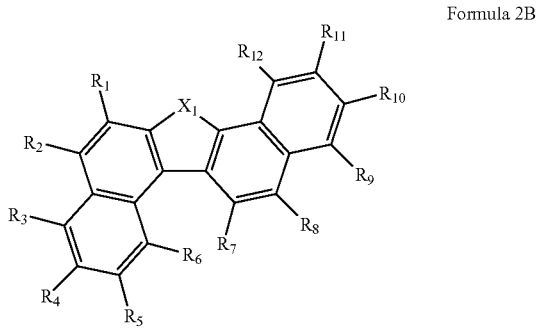

Formula 2C

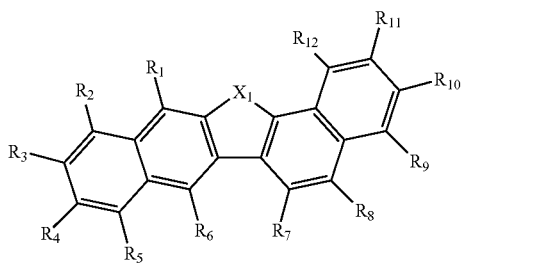

Formula 2D

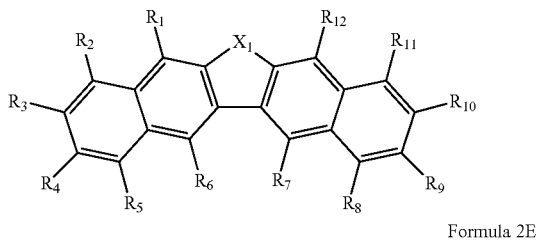

Formula 2E

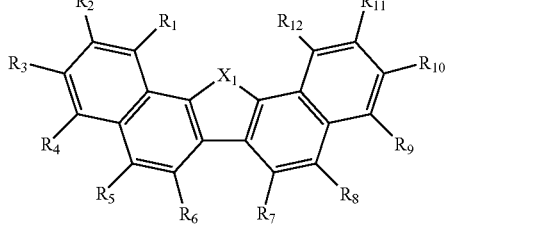

-continued

Formula 2-2

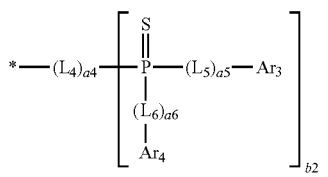

Formula 2-3

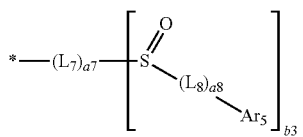

Formula 2-4

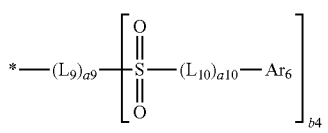

Formula 2-11

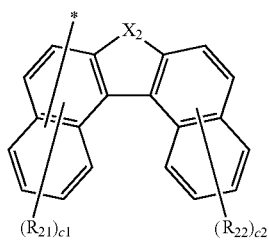

Formula 2-12

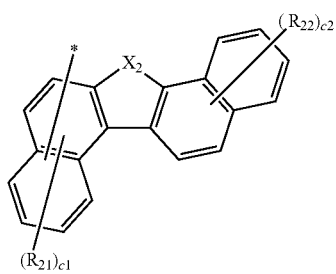

Formula 2-13

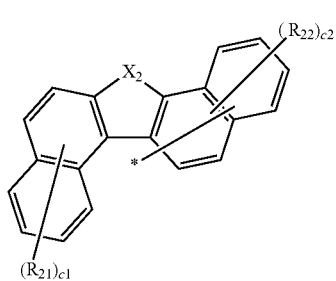

Formula 2-14

-continued

Formula 2-15

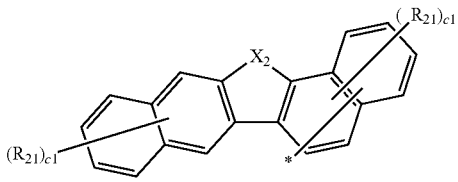

Formula 2-16

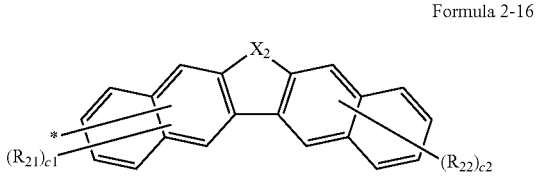

Formula 2-17

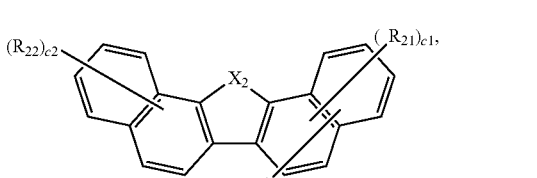

wherein, $X_1$ and $X_2$ in Formulae 2B to 2E and Formulae 2-11 to 2-17 are each independently O or S;

$R_1$ to $R_{12}$ in Formulae 2B to 2E are each independently selected from a binding site to $A_1$ in Formula 1, hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), wherein at least one selected from $R_1$ to $R_{12}$ is a binding site to $A_1$ in Formula 1, and a number of binding sites is equal to n1;

$L_4$ to $L_{10}$ in Formulae 2-2 to 2-4 are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a4 to a10 in Formulae 2-2 to 2-4 are each independently an integer selected from 0 to 5;

$Ar_3$ to $Ar_6$ in Formulae 2-2 to 2-4 are each independently selected from groups represented by Formulae 2-11 to 2-17, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b2 to b4 in Formulae 2-2 to 2-4 are each independently an integer selected from 1 to 5;

$R_{21}$ and $R_{22}$ in Formulae 2-11 to 2-17 are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

c1 in Formulae 2-11 to 2-17 is an integer selected from 0 to 5; and c2 in Formulae 2-11 to 2-17 is an integer selected from 0 to 6, wherein at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein $X_1$ and $X_2$ are both O.

3. The condensed cyclic compound of claim 1, wherein $R_1$ to $R_{12}$ are each independently selected from:

a binding site to $A_1$ in Formula 1, hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group and an imidazopyrimidinyl group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ are each independently selected from a $C_1$-$C_{10}$ alkyl group, a $C_1$-$C_{10}$ alkoxy group, a phenyl group, and a naphthyl group, and wherein at least one selected from $R_1$ to $R_{12}$ is a binding site to $A_1$ in Formula 1, and a number of binding sites is equal to n1.

4. The condensed cyclic compound of claim 1, wherein n1 is 1 or 2.

5. The condensed cyclic compound of claim 1, wherein $L_4$ to $L_{10}$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, and a naphthyl group.

6. The condensed cyclic compound of claim 1, wherein $L_4$ to $L_{10}$ are each independently selected from groups represented by Formula 3-1 to Formula 3-42:

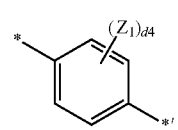

Formula 3-1

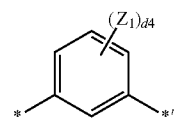

Formula 3-2

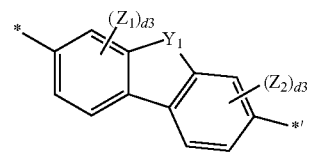

Formula 3-3

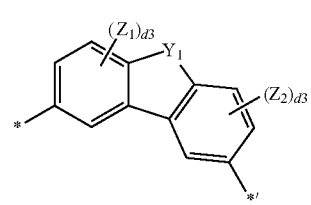

Formula 3-4

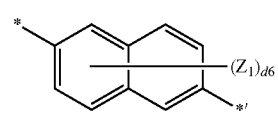

Formula 3-5

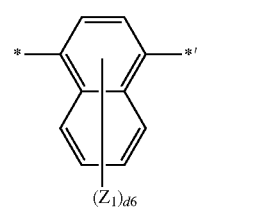

Formula 3-6

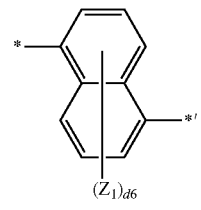

Formula 3-7

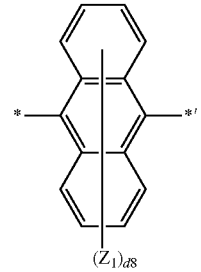

Formula 3-8

-continued
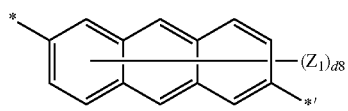
Formula 3-9
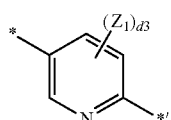
Formula 3-10
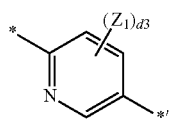
Formula 3-11
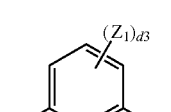
Formula 3-12
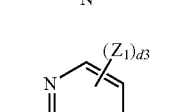
Formula 3-13
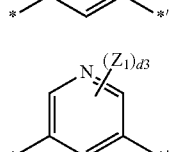
Formula 3-14
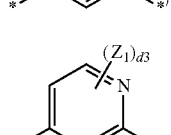
Formula 3-15
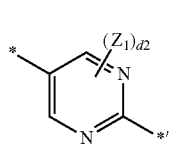
Formula 3-16
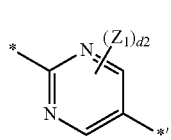
Formula 3-17
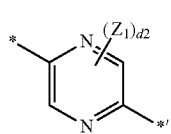
Formula 3-18
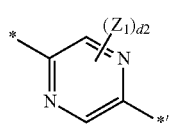
Formula 3-19
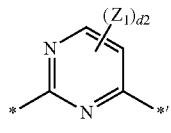
Formula 3-20
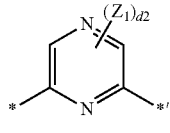
Formula 3-21
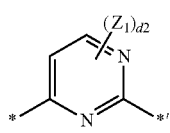
Formula 3-22
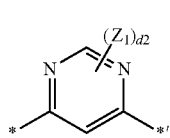
Formula 3-23
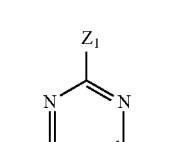
Formula 3-24
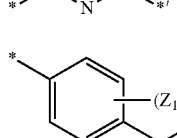
Formula 3-25
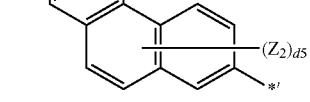
Formula 3-26
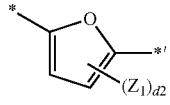
Formula 3-27
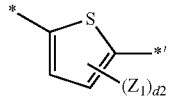
Formula 3-28
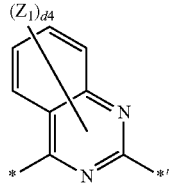
Formula 3-29
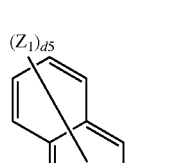
Formula 3-30
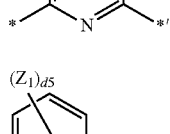
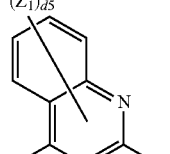

Formula 3-31
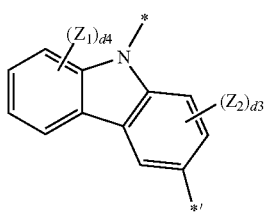

Formula 3-32
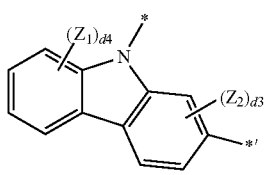

Formula 3-33
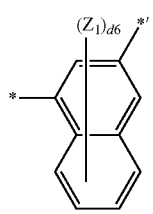

Formula 3-34
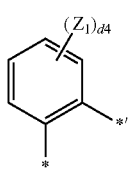

Formula 3-35
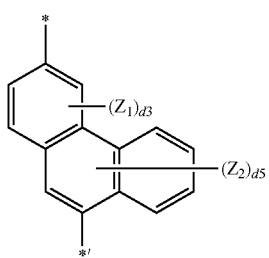

Formula 3-36
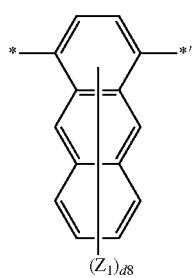

Formula 3-37
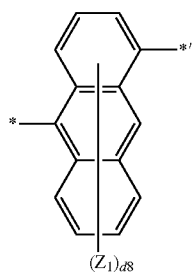

Formula 3-38
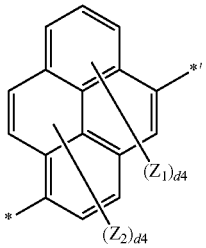

Formula 3-39
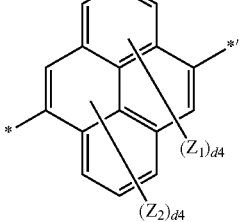

Formula 3-40
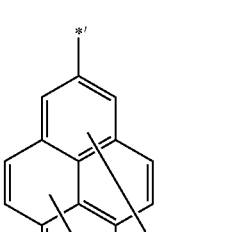

Formula 3-41
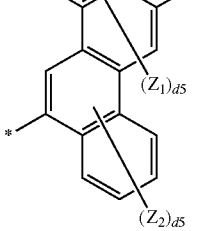

Formula 3-42
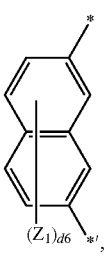

wherein, in Formulae 3-1 to 3-42, $Y_1$ is selected from O, S, $C(Z_3)(Z_4)$, $N(Z_5)$, and $Si(Z_6)(Z_7)$;

$Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, and a naphthyl group;

d2 is 1 or 2;

d3 is an integer selected from 1 to 3;

d4 is an integer selected from 1 to 4;

d5 is an integer selected from 1 to 5;

d6 is an integer selected from 1 to 6;

d8 is an integer selected from 1 to 8; and

\* and \*' are each independently a binding site with an adjacent atom.

7. The condensed cyclic compound of claim 1, wherein $L_4$ to $L_{10}$ are each independently selected from groups represented by Formula 4-1 to Formula 4-36:

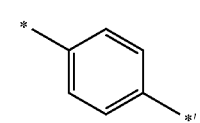

Formula 4-1

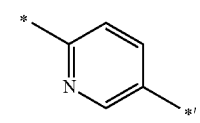

Formula 4-2

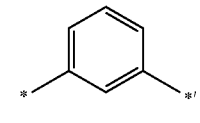

Formula 4-3

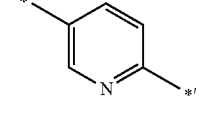

Formula 4-4

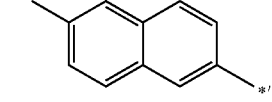

Formula 4-5

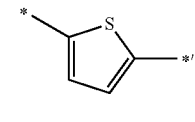

Formula 4-6

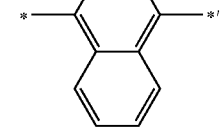

Formula 4-7

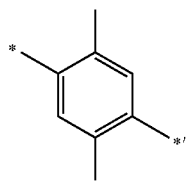

Formula 4-8

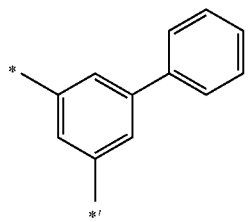

Formula 4-9

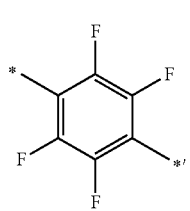

Formula 4-10

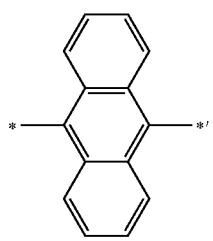

Formula 4-11

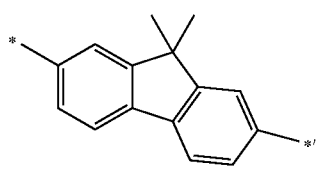

Formula 4-12

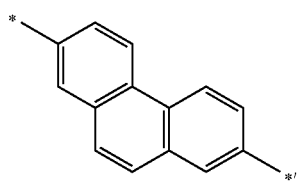

Formula 4-13

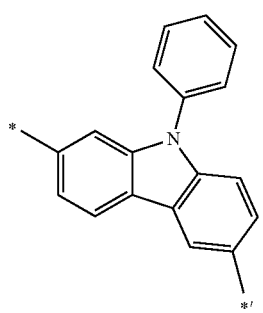

Formula 4-14

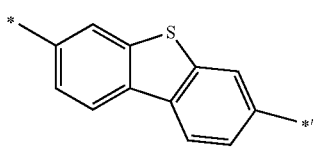
Formula 4-15
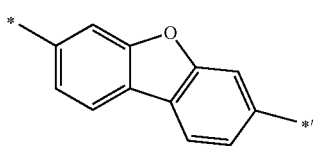
Formula 4-16
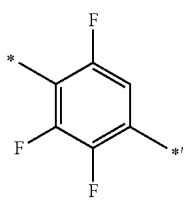
Formula 4-17
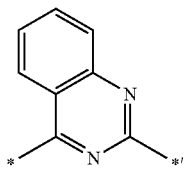
Formula 4-18
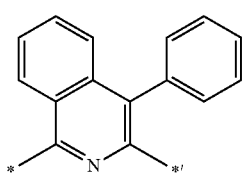
Formula 4-19
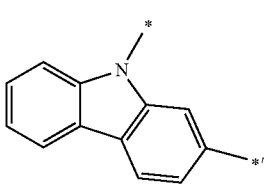
Formula 4-20
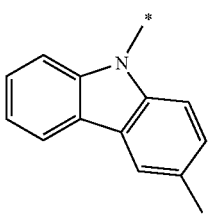
Formula 4-21
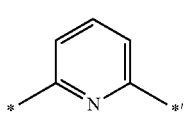
Formula 4-22
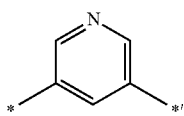
Formula 4-23
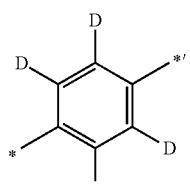
Formula 4-24
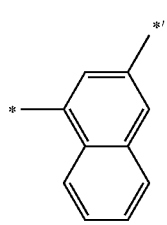
Formula 4-25
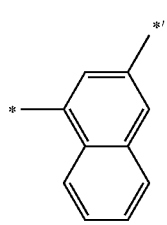
Formula 4-26
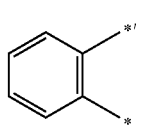
Formula 4-27
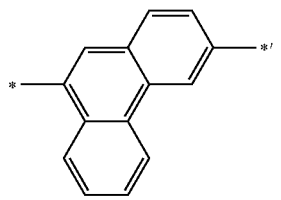
Formula 4-28
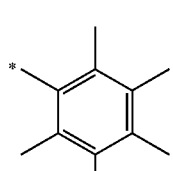
Formula 4-29
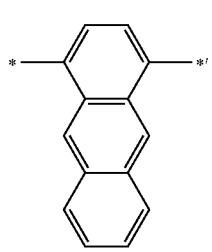
Formula 4-30
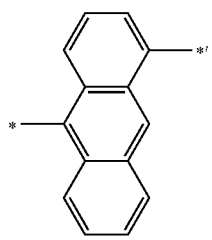
Formula 4-31
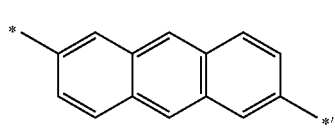

-continued

Formula 4-32

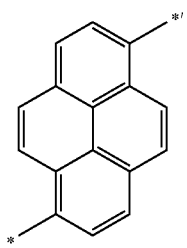

Formula 4-33

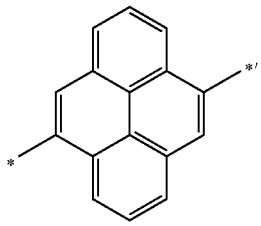

Formula 4-34

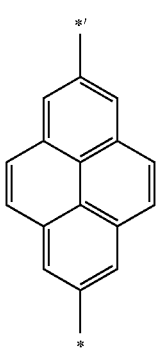

Formula 4-35

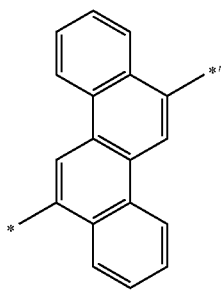

Formula 4-36

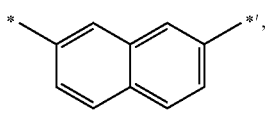

wherein, in Formulae 4-1 and 4-36, * and *' are each independently a binding site with an adjacent atom.

8. The condensed cyclic compound of claim 1, wherein a4, a7, and a9 are each independently selected from 1, 2, and 3.

9. The condensed cyclic compound of claim 1, wherein $Ar_3$ to $Ar_6$ are each independently selected from:

groups represented by Formula 2-11 to Formula 2-17, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, and a naphthyl group.

10. The condensed cyclic compound of claim 1, wherein $Ar_3$ to $Ar_6$ are each independently selected from:

groups represented by any of Formulae 2-11(1), 2-11(2), 2-12(1), 2-12(2), 2-14(1), 2-16(1), and 2-17(1), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si(Q$_{33}$)(Q$_{34}$)(Q$_{35}$), wherein Q$_{33}$ to Q$_{35}$ are each independently selected from a C$_1$-C$_{10}$ alkyl group, a C$_1$-C$_{10}$ alkoxy group, a phenyl group, and a naphthyl group:

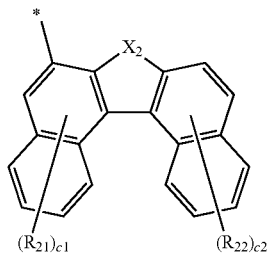

Formula 2-11(1)

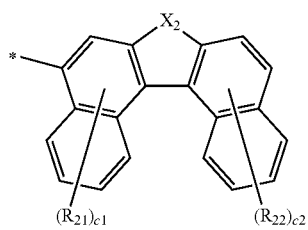

Formula 2-11(2)

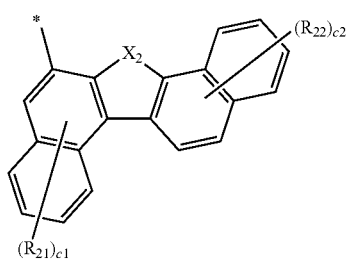

Formula 2-12(1)

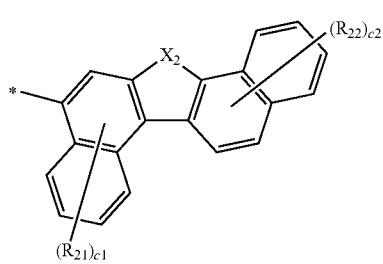

Formula 2-12(2)

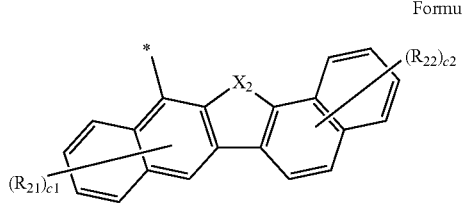

Formula 2-14(1)

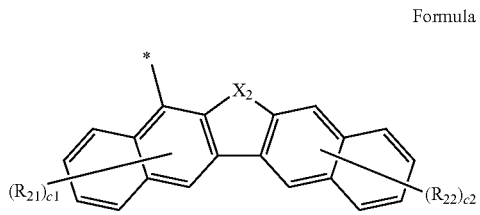

Formula 2-16(1)

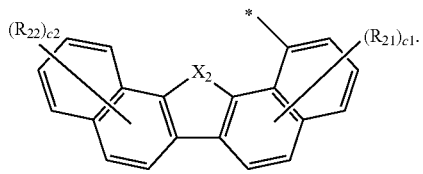

Formula 2-17(1)

11. The condensed cyclic compound of claim 1, wherein R$_1$ to R$_{12}$ in Formulae 2B to 2E are each independently selected from a binding site to A$_1$ in Formula 1, hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, groups represented by Formulae 5-1 to 5-75, and —Si(Q$_3$)(Q$_4$)(Q$_5$), wherein at least one selected from R$_1$ to R$_{12}$ is a binding site to A$_1$ in Formula 1, and a number of binding sites is equal to n1;

Ar$_3$ to Ar$_6$ in Formulae 2-2 to 2-4 are each independently selected from groups represented by Formulae 2-11 to 2-17 and groups represented by Formulae 5-1 to 5-75; and R$_{21}$ and R$_{22}$ in Formulae 2-11 to 2-17 are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, groups represented by Formulae 5-1 to 5-75, and —Si(Q$_3$)(Q$_4$)(Q$_5$), wherein Q$_3$ to Q$_5$ are each independently selected from a C$_1$-C$_{10}$ alkyl group, a C$_1$-C$_{10}$ alkoxy group, a phenyl group, and a naphthyl group:

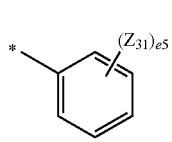

Formula 5-1

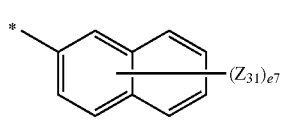

Formula 5-2

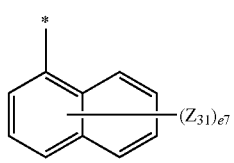

Formula 5-3

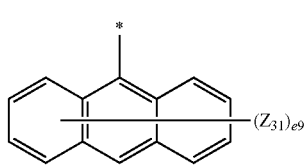

Formula 5-4

-continued
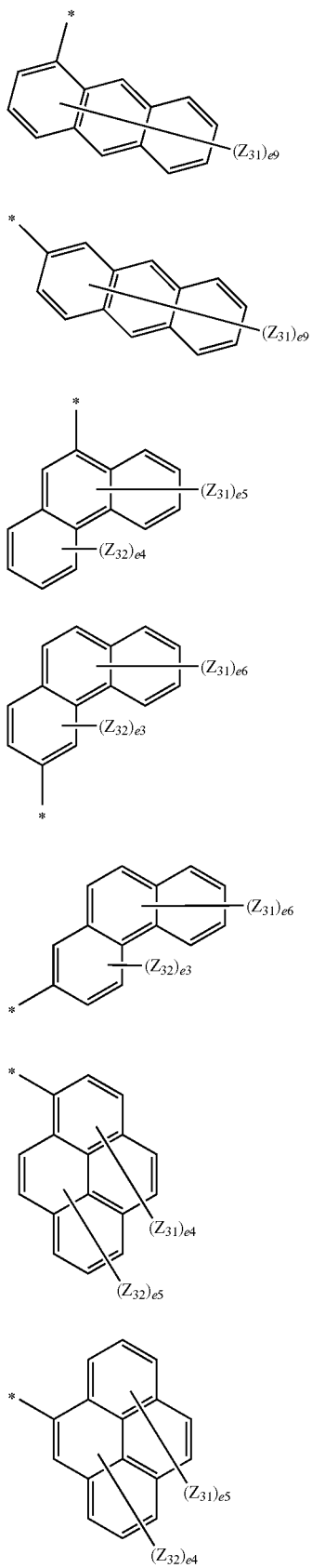
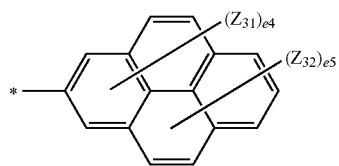
Formula 5-5
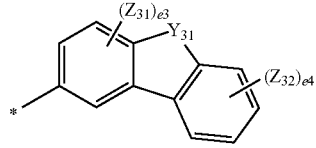
Formula 5-6
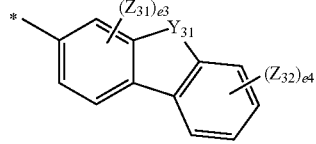
Formula 5-7
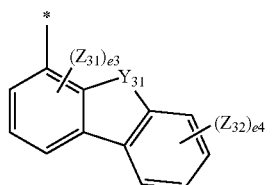
Formula 5-8
Formula 5-9
Formula 5-10
Formula 5-11
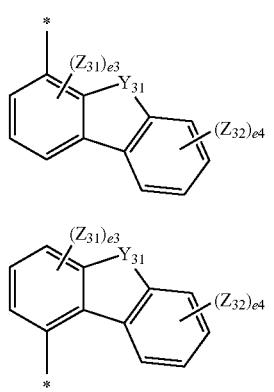
Formula 5-12
Formula 5-13
Formula 5-14
Formula 5-15
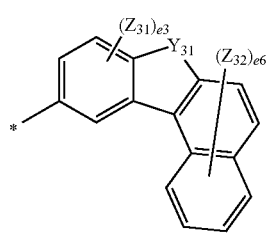
Formula 5-16
Formula 5-17
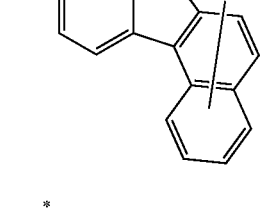
Formula 5-18
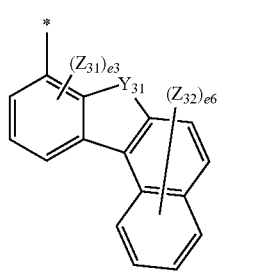
Formula 5-19

169
-continued
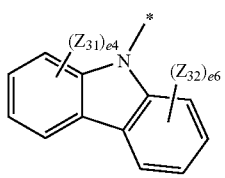
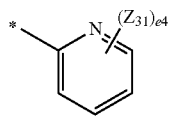
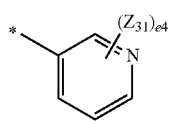
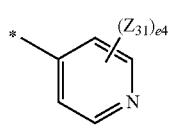
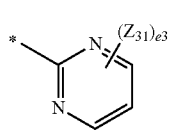
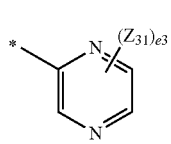
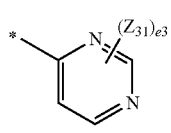
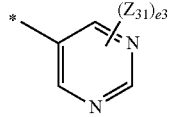
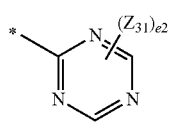
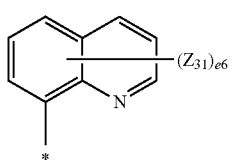
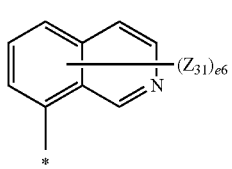
170
-continued
Formula 5-20
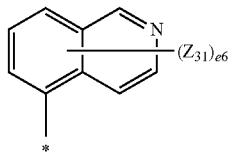
Formula 5-21
Formula 5-22
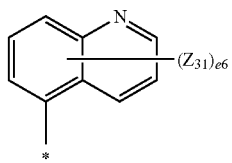
Formula 5-23
Formula 5-24
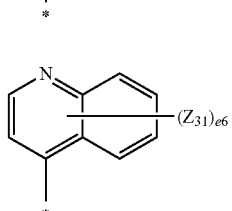
Formula 5-25
Formula 5-26
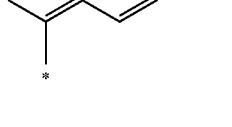
Formula 5-27
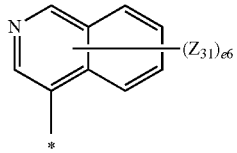
Formula 5-28
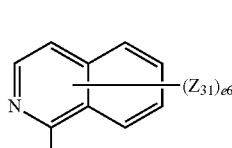
Formula 5-29
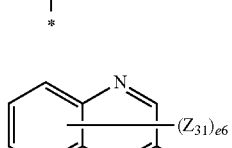
Formula 5-30
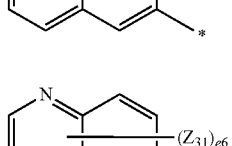
Formula 5-31
Formula 5-32
Formula 5-33
Formula 5-34
Formula 5-35
Formula 5-36
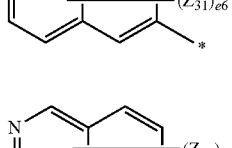
Formula 5-37
Formula 5-38
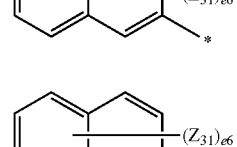
Formula 5-39
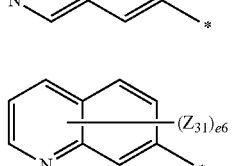
Formula 5-40

| | |
|---|---|
| Formula 5-41 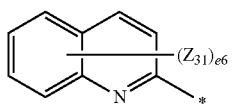 | Formula 5-53 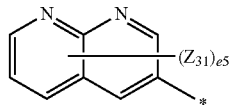 |
| Formula 5-42 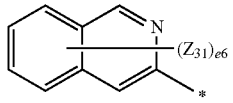 | Formula 5-54 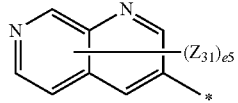 |
| Formula 5-43 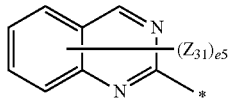 | Formula 5-55 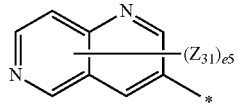 |
| Formula 5-44 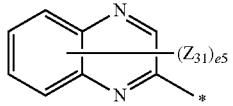 | Formula 5-56 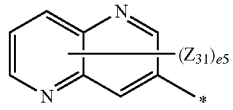 |
| Formula 5-45 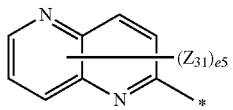 | Formula 5-57 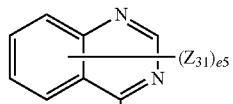 |
| Formula 5-46 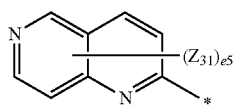 | Formula 5-58 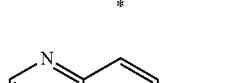 |
| Formula 5-47 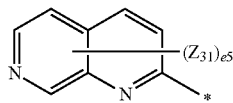 | Formula 5-59 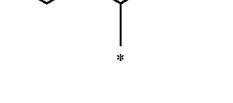 |
| Formula 5-48 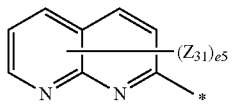 | Formula 5-60 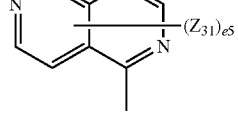 |
| Formula 5-49 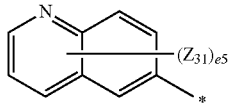 | Formula 5-61 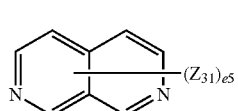 |
| Formula 5-50 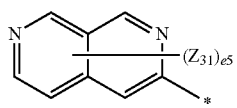 | Formula 5-62 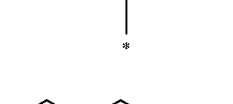 |
| Formula 5-51 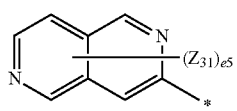 | |
| Formula 5-52 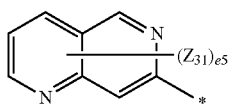 | | wherein, in Formulae 5-1 to 5-75, $Y_{31}$ is selected from O, S, $C(Z_{33})(Z_{34})$, $N(Z_{35})$, and $Si(Z_{36})(Z_{37})$;

$Z_{31}$ to $Z_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e2 is an integer selected from 1 and 2 e3 is an integer selected from 1 to 3;

e4 is an integer selected from 1 to 4;

e5 is an integer selected from 1 to 5;

e6 is an integer selected from 1 to 6;

e7 is an integer selected from 1 to 7;

e8 is an integer selected from 1 to 8;

e9 is an integer selected from 1 to 9; and

\* is a binding site with an adjacent atom.

12. The condensed cyclic compound of claim 1, wherein $R_1$ to $R_{12}$ in Formulae 2B to 2E are each independently selected from a binding site to $A_1$ in Formula 1, hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, groups represented by Formulae 6-1 to 6-43, groups represented by Formula 10-1 to 10-117, and —$Si(Q_3)(Q_4)(Q_5)$, wherein at least one selected from $R_1$ to $R_{12}$ is a binding site to $A_1$ in Formula 1, and a number of binding sites is equal to n1;

$Ar_3$ to $Ar_6$ in Formulae 2-2 to 2-4 are each independently selected from groups represented by Formulae 2-11 to 2-17, groups represented by Formulae 6-1 to 6-43, and groups represented by Formulae 10-1 to 10-117; and $R_{21}$ and $R_{22}$ in Formulae 2-11 to 2-17 are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, groups represented by Formulae 6-1 to 6-43, groups represented by Formulae 10-1 to 10-117, and —Si($Q_3$)($Q_4$)($Q_5$), wherein $Q_3$ to $Q_5$ are each independently selected from a $C_1$-$C_{10}$ alkyl group, a $C_1$-$C_{10}$ alkoxy group, a phenyl group, and a naphthyl group:

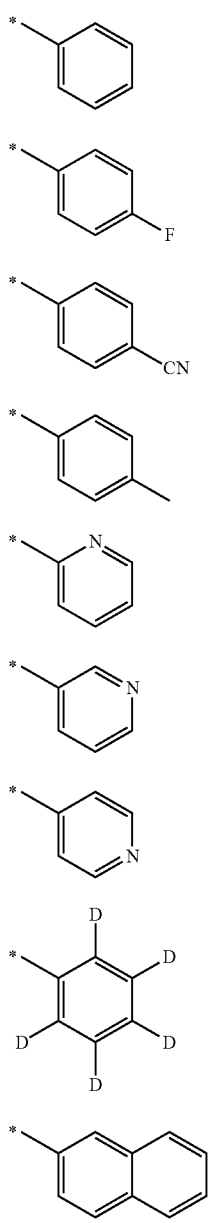

Formula 6-1

Formula 6-2

Formula 6-3

Formula 6-4

Formula 6-5

Formula 6-6

Formula 6-7

Formula 6-8

Formula 6-9

-continued

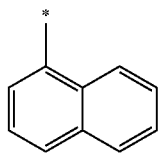

Formula 6-10

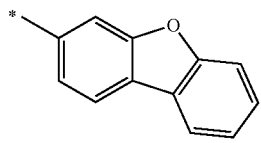

Formula 6-11

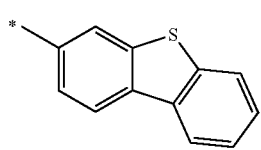

Formula 6-12

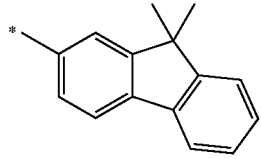

Formula 6-13

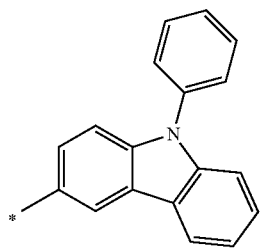

Formula 6-14

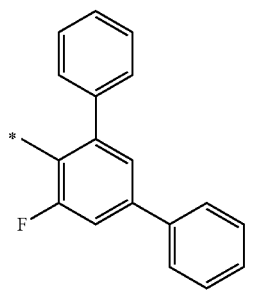

Formula 6-15

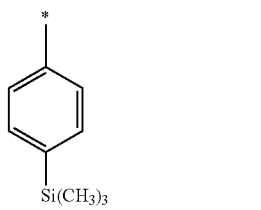

Formula 6-16

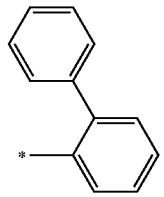

Formula 6-17

-continued
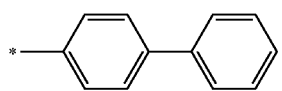
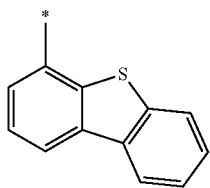
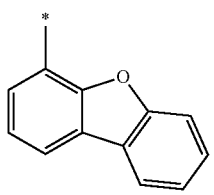
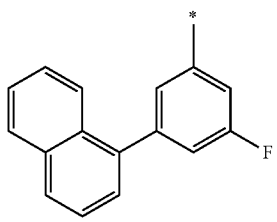
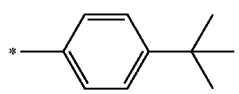
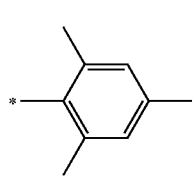
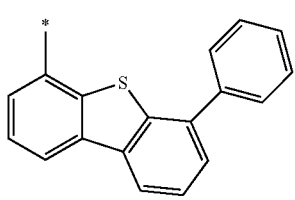
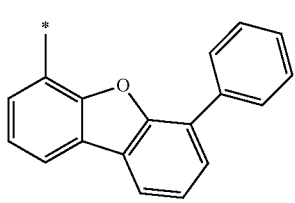
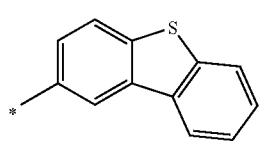
-continued
Formula 6-18
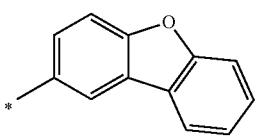
Formula 6-19
Formula 6-20
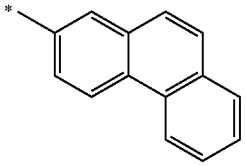
Formula 6-21
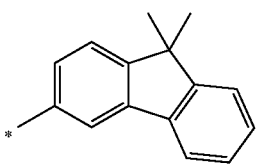
Formula 6-22
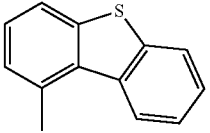
Formula 6-23
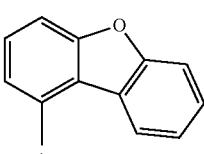
Formula 6-24
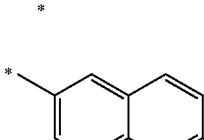
Formula 6-25
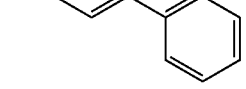
Formula 6-26
Formula 6-27
Formula 6-28
Formula 6-29
Formula 6-30
Formula 6-31
Formula 6-32
Formula 6-33
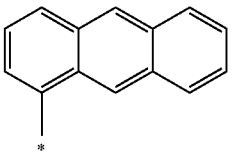
Formula 6-34
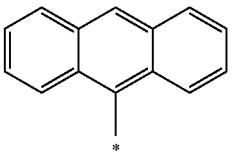
Formula 6-35
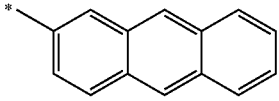

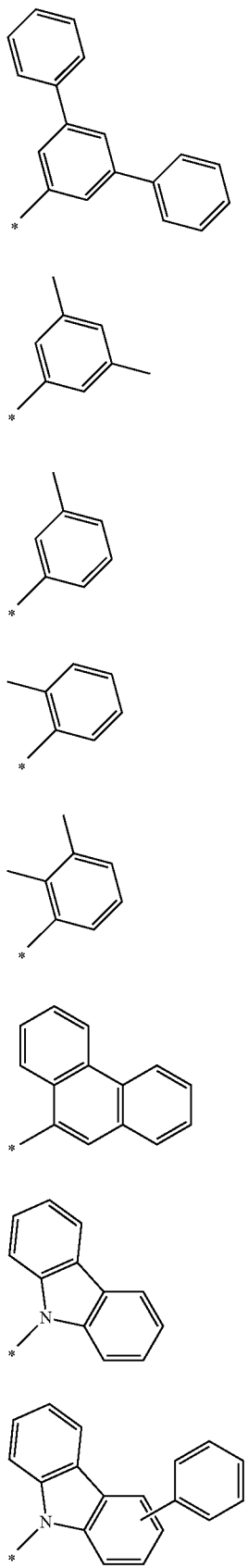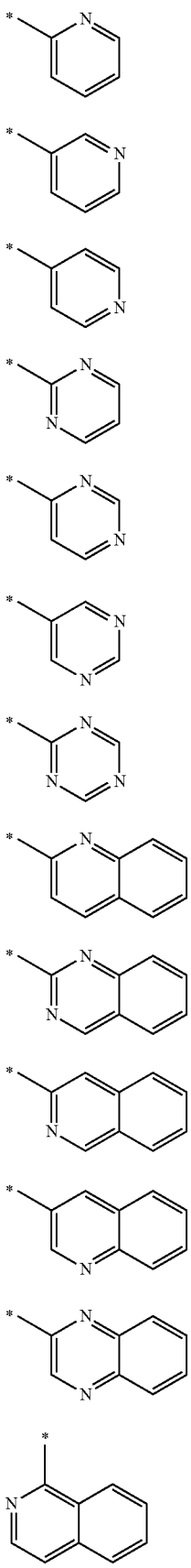
Formula 6-36
Formula 6-37
Formula 6-38
Formula 6-39
Formula 6-40
Formula 6-41
Formula 6-42
Formula 6-43
Formula 10-1
Formula 10-2
Formula 10-3
Formula 10-4
Formula 10-5
Formula 10-6
Formula 10-7
Formula 10-8
Formula 10-9
Formula 10-10
Formula 10-11
Formula 10-12
Formula 10-13

-continued
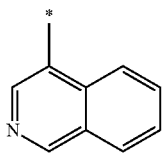
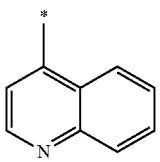
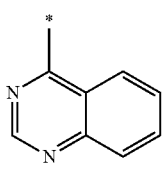
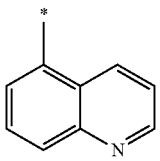
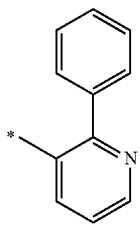
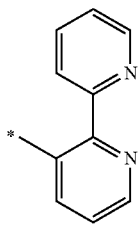
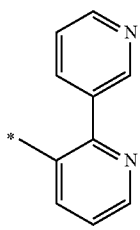
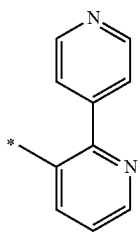
-continued
Formula 10-14
Formula 10-15
Formula 10-16
Formula 10-17
Formula 10-18
Formula 10-19
Formula 10-20
Formula 10-21
Formula 10-22
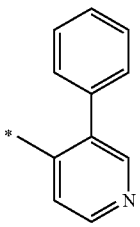
Formula 10-23
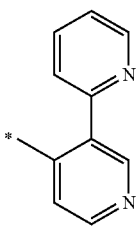
Formula 10-24
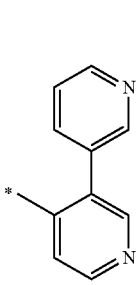
Formula 10-25
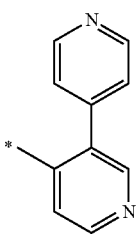
Formula 10-26
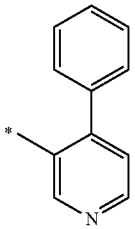
Formula 10-27
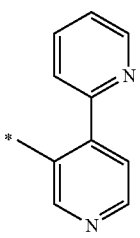

-continued
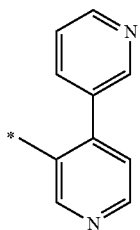
Formula 10-28
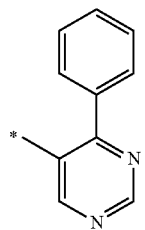
Formula 10-34
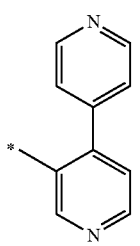
Formula 10-29
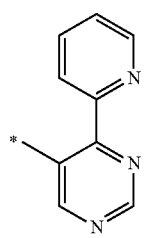
Formula 10-35
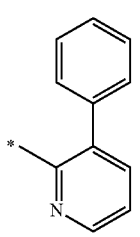
Formula 10-30
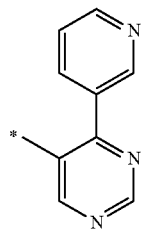
Formula 10-36
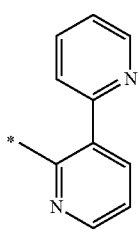
Formula 10-31
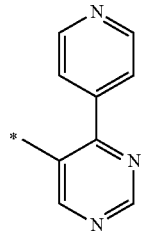
Formula 10-37
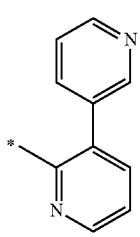
Formula 10-32
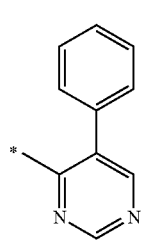
Formula 10-38
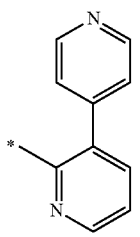
Formula 10-33
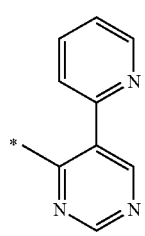
Formula 10-39

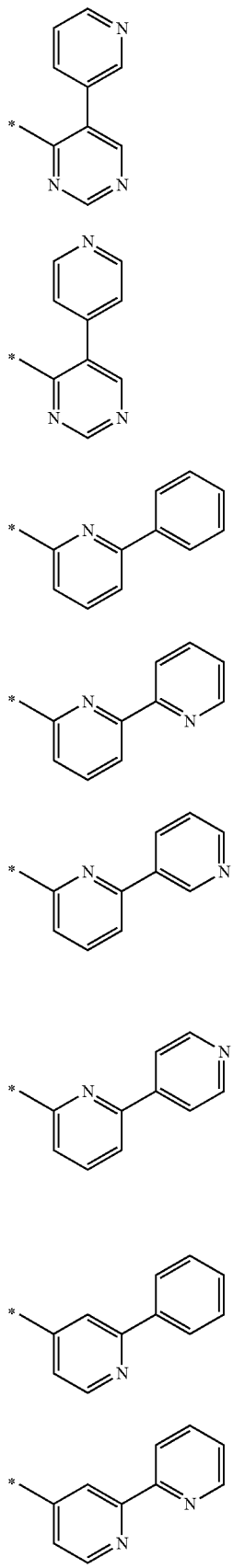
Formula 10-40
Formula 10-41
Formula 10-42
Formula 10-43
Formula 10-44
Formula 10-45
Formula 10-46
Formula 10-47
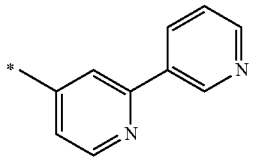
Formula 10-48
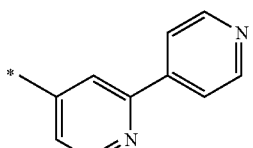
Formula 10-49
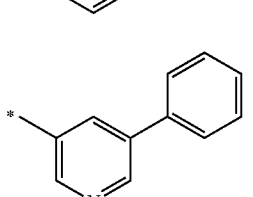
Formula 10-50
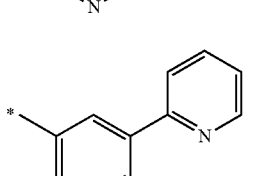
Formula 10-51
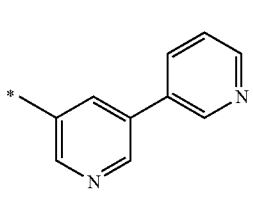
Formula 10-52
Formula 10-53
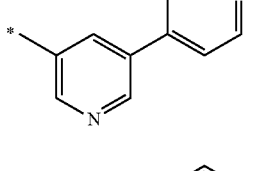
Formula 10-54
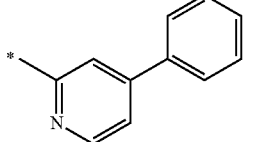
Formula 10-55
Formula 10-56

Formula 10-57
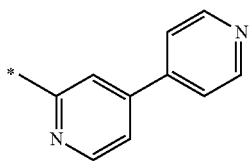
Formula 10-58
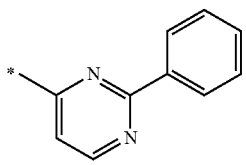
Formula 10-59
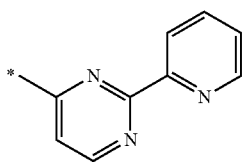
Formula 10-60
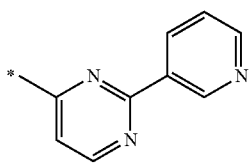
Formula 10-61
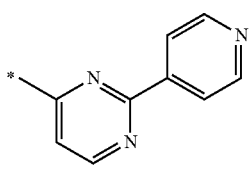
Formula 10-62
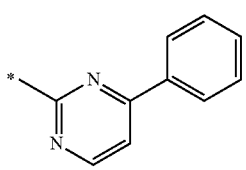
Formula 10-63
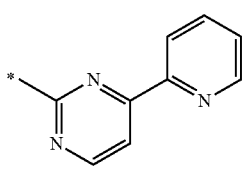
Formula 10-64
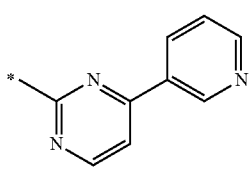
Formula 10-65
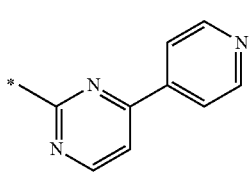
Formula 10-66
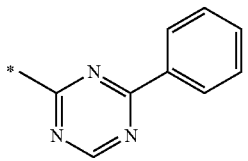
Formula 10-67
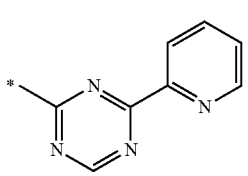
Formula 10-68
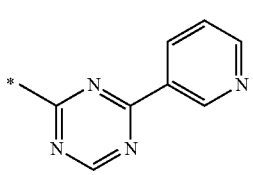
Formula 10-69
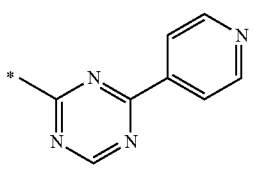
Formula 10-70
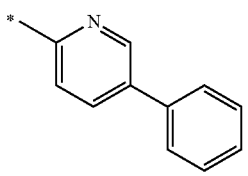
Formula 10-71
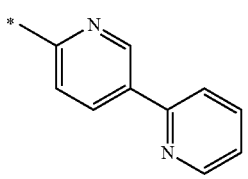
Formula 10-72
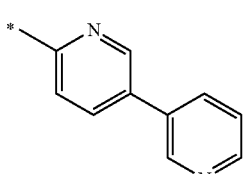
Formula 10-73
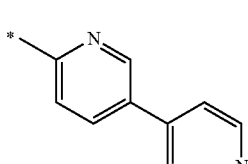
Formula 10-74
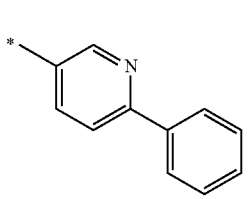

-continued
Formula 10-75
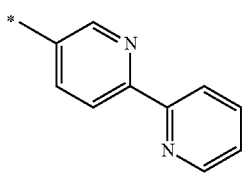
Formula 10-76
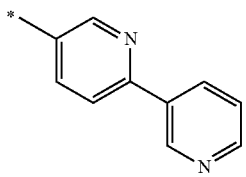
Formula 10-77
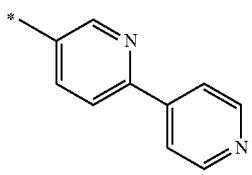
Formula 10-78
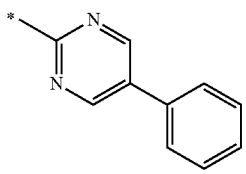
Formula 10-79
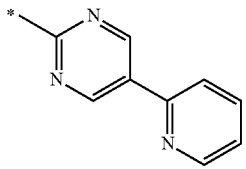
Formula 10-80
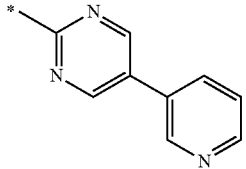
Formula 10-81
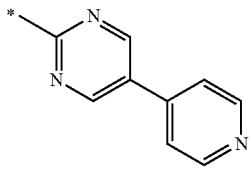
Formula 10-82
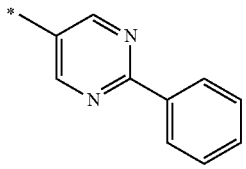
Formula 10-83
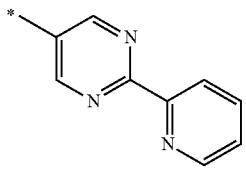
-continued
Formula 10-84
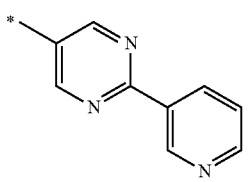
Formula 10-85
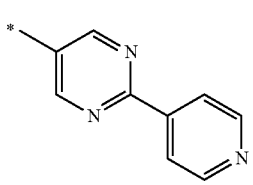
Formula 10-86
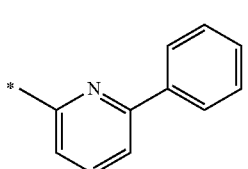
Formula 10-87
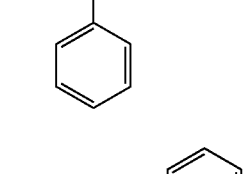
Formula 10-88
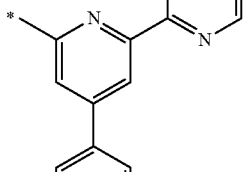
Formula 10-89
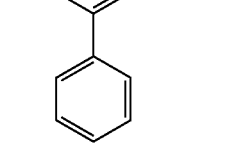

Formula 10-90
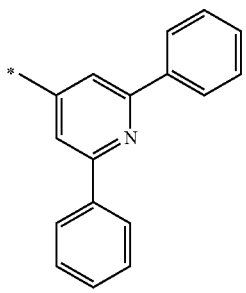
Formula 10-95
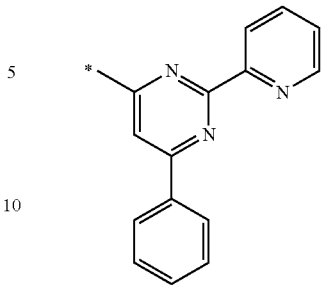
Formula 10-91
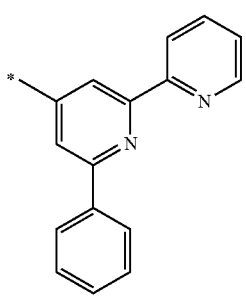
Formula 10-96
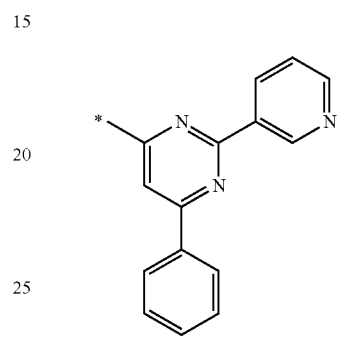
Formula 10-92
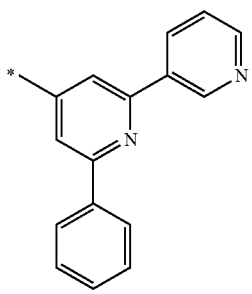
Formula 10-97
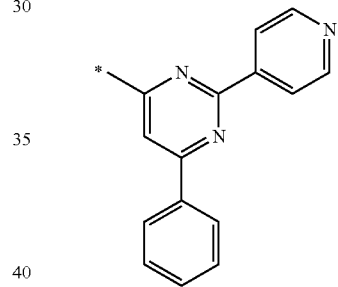
Formula 10-93
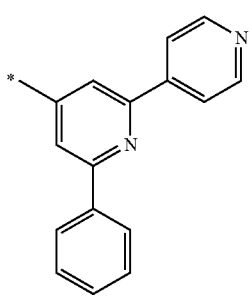
Formula 10-98
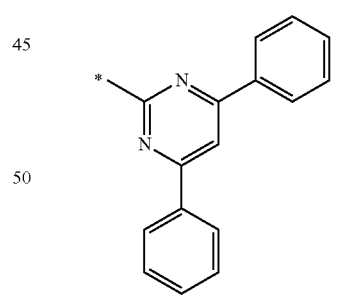
Formula 10-94
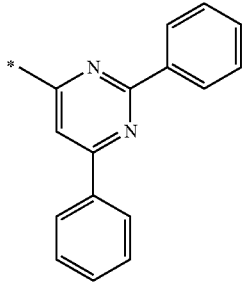
Formula 10-99
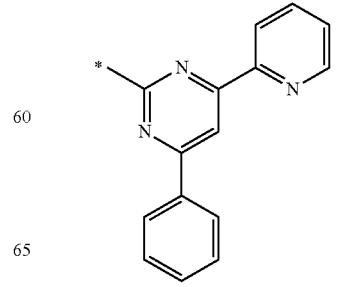

Formula 10-100
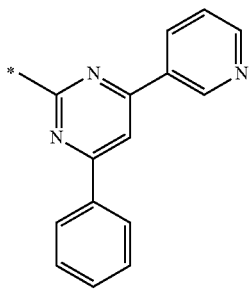
Formula 10-101
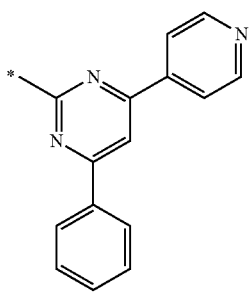
Formula 10-102
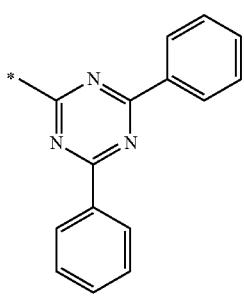
Formula 10-103
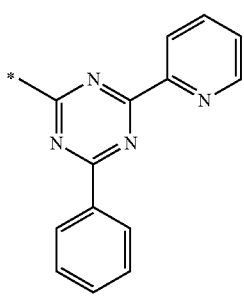
Formula 10-104
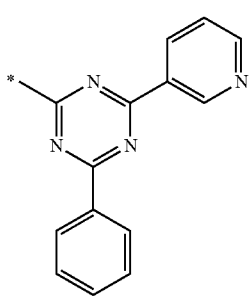
Formula 10-105
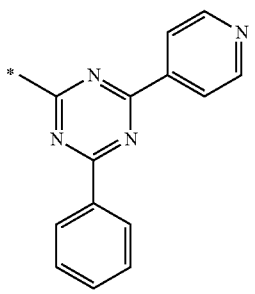
Formula 10-106
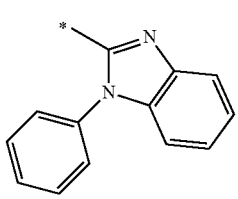
Formula 10-107
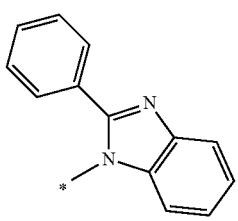
Formula 10-108
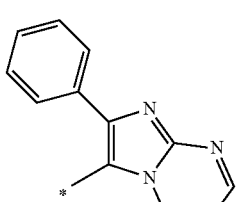
Formula 10-109
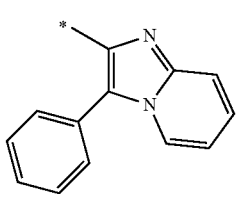
Formula 10-110
Formula 10-111
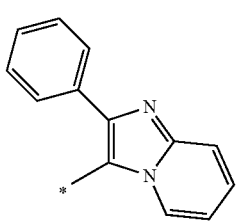

Formula 10-112
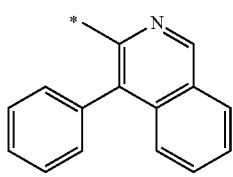
Formula 10-113
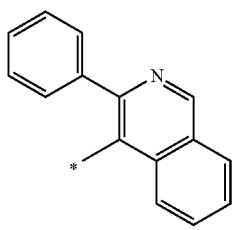
Formula 10-114
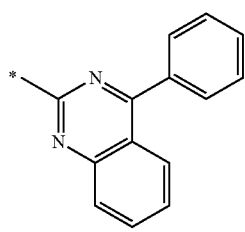
Formula 10-115
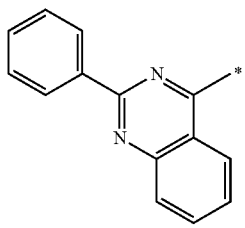
Formula 10-116
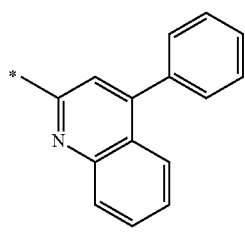
Formula 10-117
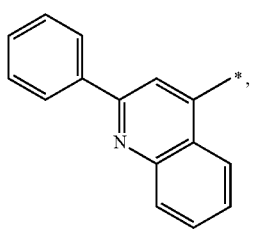
wherein, in Formulae 6-1 to 6-43 and 10-1 to 10-117, * is a binding site with an adjacent atom.
13. The condensed cyclic compound of claim 1, wherein the condensed cyclic compound is represented by one of Formulae 2B-1 to 2E-1:
Formula 2B-1
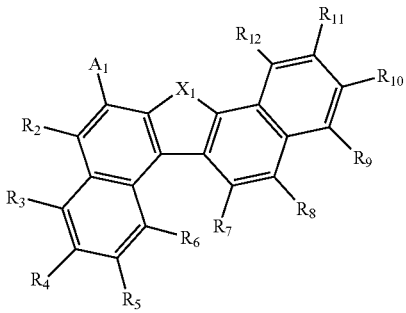
Formula 2B-2
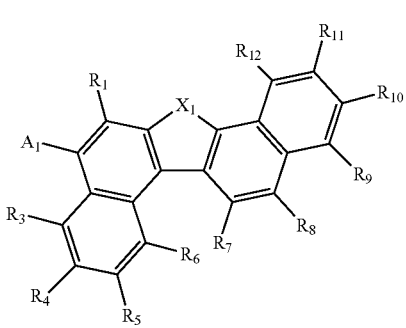
Formula 2C-1
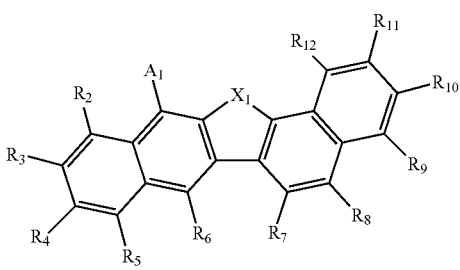
Formula 2D-1
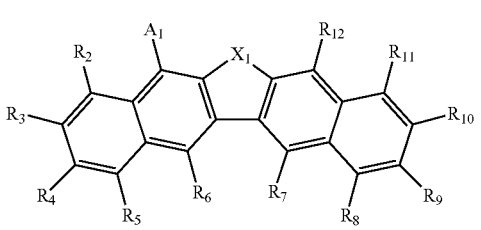
Formula 2E-1
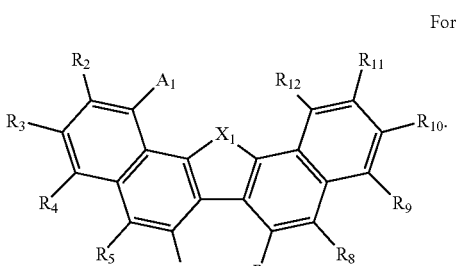

14. The condensed cyclic compound of claim 1, wherein the condensed cyclic compound is represented by one of Formulae 1(3) to 1(8):

Formula 1(3)

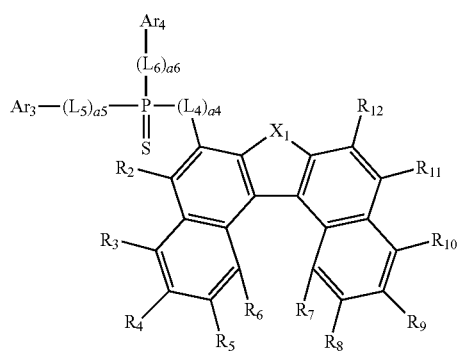

Formula 1(4)

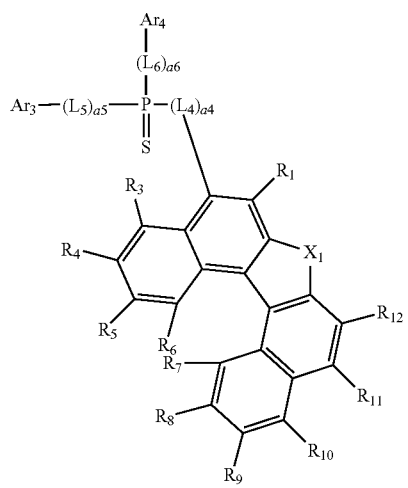

Formula 1(5)

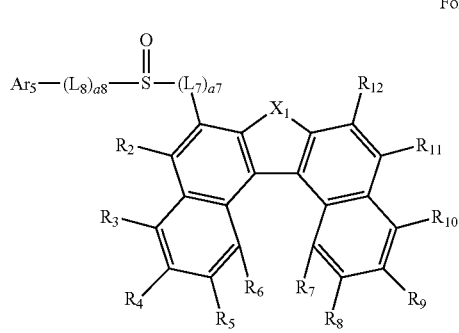

Formula 1(6)

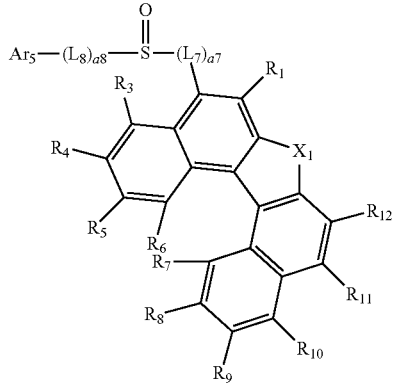

Formula 1(7)

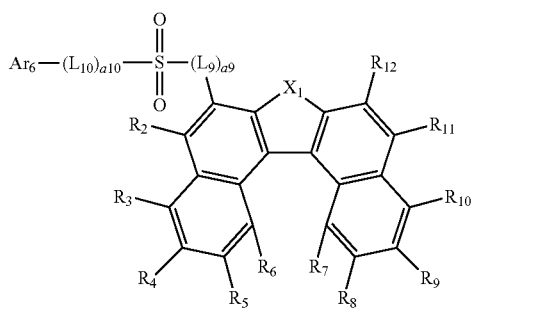

Formula 1(8)

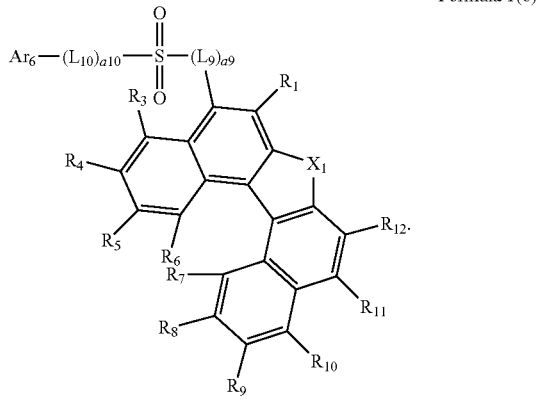

15. The condensed cyclic compound of claim 1, wherein $X_1$ is O;
$L_4$ to $L_{10}$ are each independently selected from:
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$);

a4, a7, and a9 are each independently selected from 1 and 2;

a5, a6, a8, and a10 are each independently selected from 0, 1, and 2;

$R_1$ to $R_{12}$ are each independently selected from a binding site to $A_1$ in Formula 1, hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, groups represented by Formulae 5-1 to 5-75, and —Si($Q_3$)($Q_4$)($Q_5$), wherein at least one selected from $R_1$ to $R_{12}$ is a binding site to $A_1$ in Formula 1, and a number of binding sites is equal to n1;

$Ar_3$ to $Ar_6$ are each independently selected from groups represented by Formulae 2-11 to 2-17, and groups represented by Formulae 5-1 to 5-75; and $R_{21}$ and $R_{22}$ in Formulae 2-11 to 2-17 are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, groups represented by Formulae 5-1 to 5-75, and —Si($Q_3$)($Q_4$)($Q_5$), wherein $Q_3$ to $Q_5$ and $Q_{33}$ to $Q_{35}$ are each independently selected from a $C_1$-$C_{10}$ alkyl group, a $C_1$-$C_{10}$ alkoxy group, a phenyl group, and a naphthyl group:

Formula 5-1

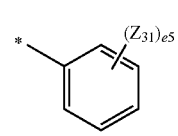

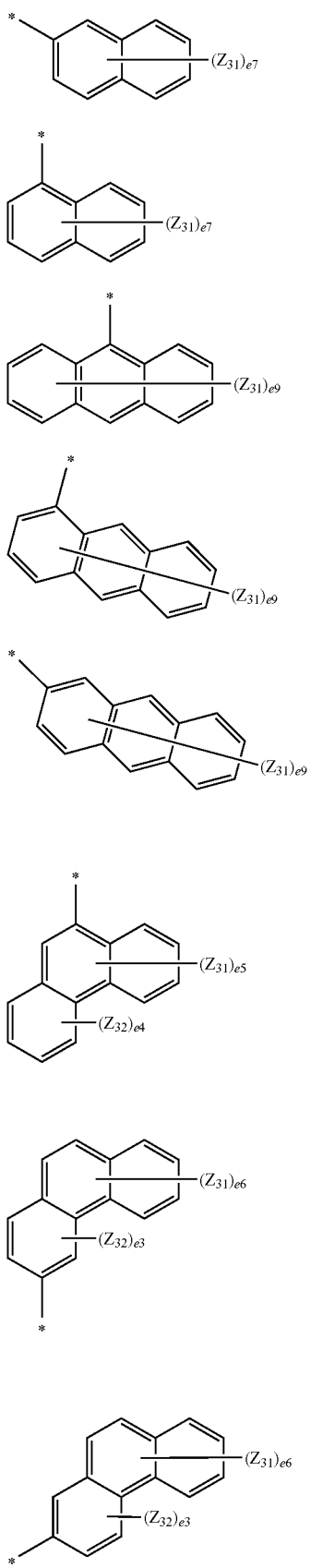
Formula 5-2
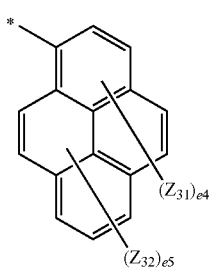
Formula 5-3
Formula 5-4
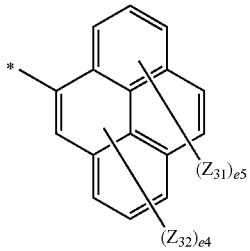
Formula 5-5
Formula 5-6
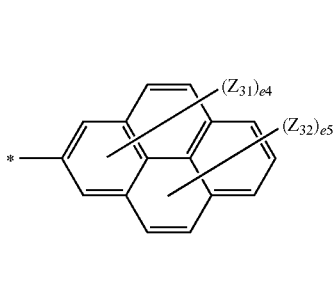
Formula 5-7
Formula 5-8
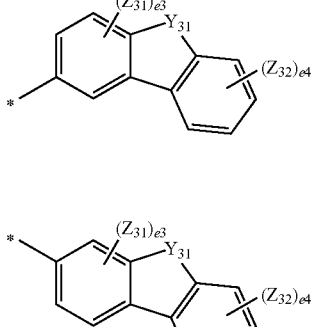
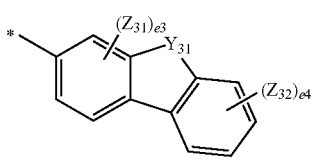
Formula 5-9
Formula 5-10
Formula 5-11
Formula 5-12
Formula 5-13
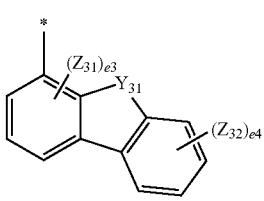
Formula 5-14
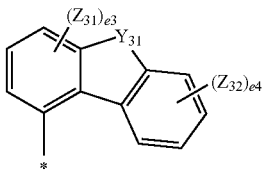
Formula 5-15
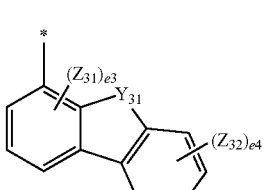
Formula 5-16
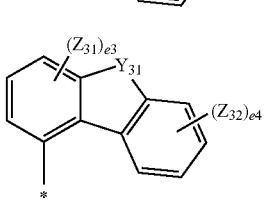

-continued
Formula 5-17
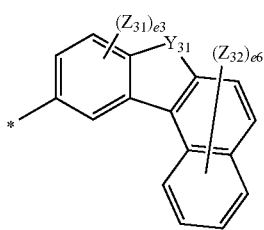
Formula 5-18
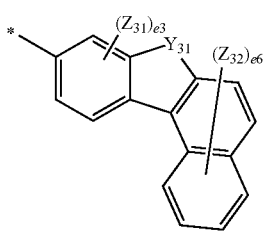
Formula 5-19
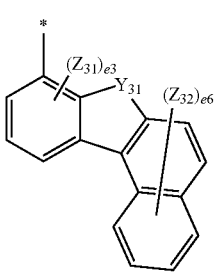
Formula 5-20
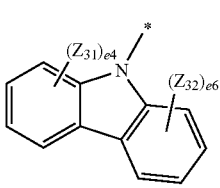
Formula 5-21
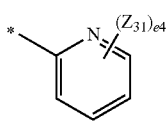
Formula 5-22
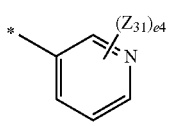
Formula 5-23
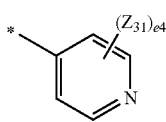
Formula 5-24
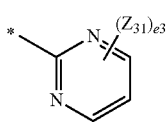
Formula 5-25
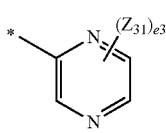
-continued
Formula 5-26
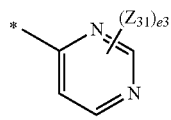
Formula 5-27
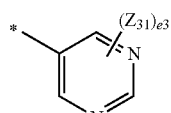
Formula 5-28
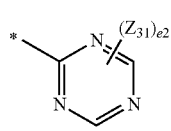
Formula 5-29
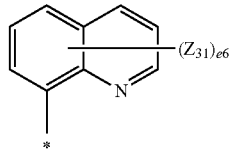
Formula 5-30
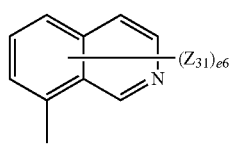
Formula 5-31
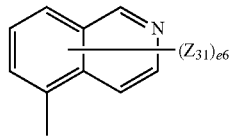
Formula 5-32
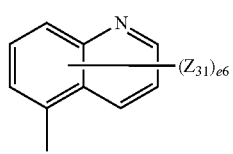
Formula 5-33
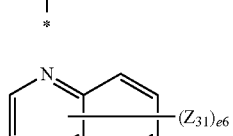
Formula 5-34
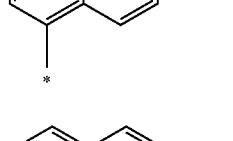
Formula 5-35
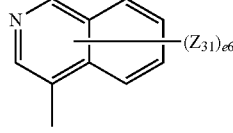
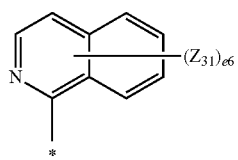

| | |
|---|---|
| Formula 5-36 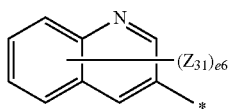 | Formula 5-48 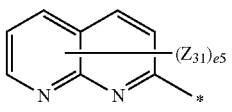 |
| Formula 5-37 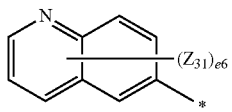 | Formula 5-49 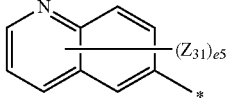 |
| Formula 5-38 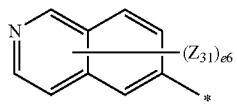 | Formula 5-50 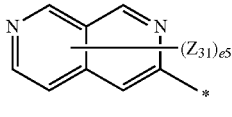 |
| Formula 5-39 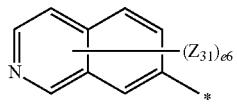 | Formula 5-51 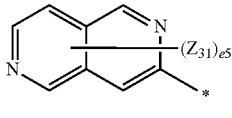 |
| Formula 5-40 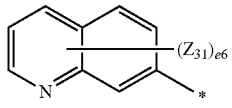 | Formula 5-52 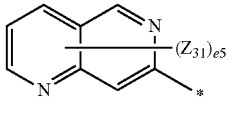 |
| Formula 5-41 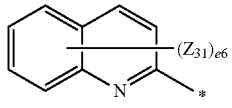 | Formula 5-53 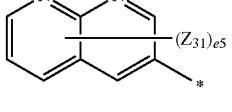 |
| Formula 5-42 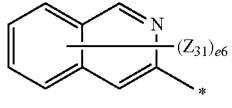 | Formula 5-54 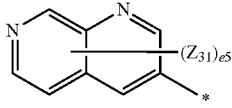 |
| Formula 5-43 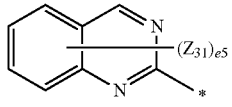 | Formula 5-55 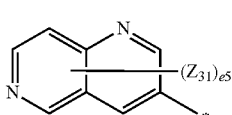 |
| Formula 5-44 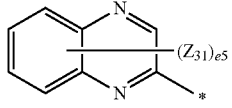 | Formula 5-56 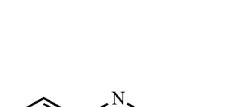 |
| Formula 5-45 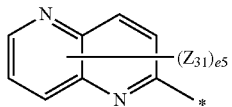 | Formula 5-57 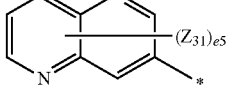 |
| Formula 5-46 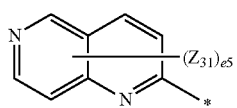 | Formula 5-58 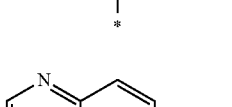 |
| Formula 5-47 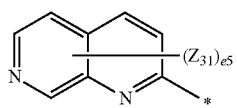 | |

-continued

Formula 5-59
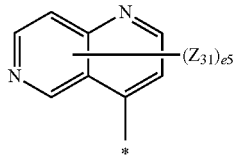

Formula 5-60
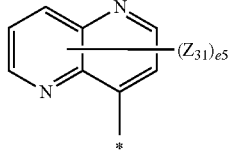

Formula 5-61
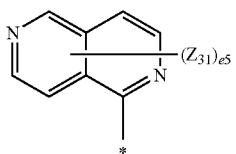

Formula 5-62
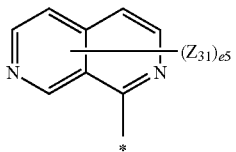

Formula 5-63
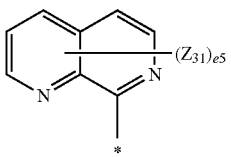

Formula 5-64
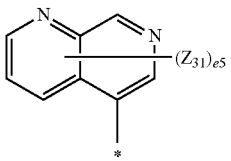

Formula 5-65
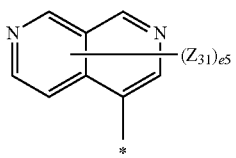

Formula 5-66
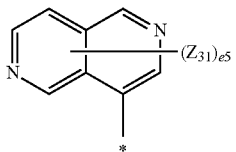

Formula 5-67
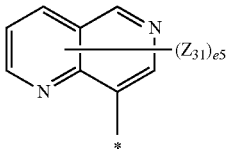

-continued

Formula 5-68
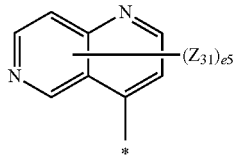

Formula 5-69
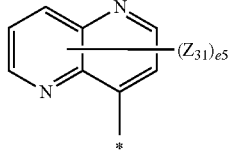

Formula 5-70
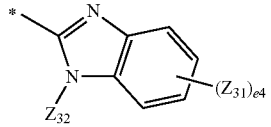

Formula 5-71
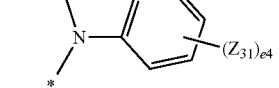

Formula 5-72
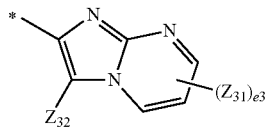

Formula 5-73
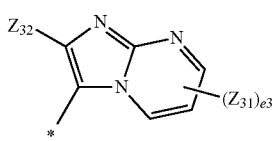

Formula 5-74

Formula 5-75

wherein, in Formulae 5-1 to 5-75, $Y_{31}$ is selected from O, S, C($Z_{33}$)($Z_{34}$), N($Z_{35}$), and Si($Z_{36}$)($Z_{37}$);

$Z_{31}$ to $Z_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —Si($Q_{33}$)($Q_{34}$)($Q_{35}$), wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e2 is an integer selected from 1 and 2;
e3 is an integer selected from 1 to 3;
e4 is an integer selected from 1 to 4;
e5 is an integer selected from 1 to 5;
e6 is an integer selected from 1 to 6;
e7 is an integer selected from 1 to 7;
e8 is an integer selected from 1 to 8;
e9 is an integer selected from 1 to 9; and
* is a binding site with an adjacent atom.

16. An organic light-emitting device comprising: a first electrode; a second electrode facing the first electrode; and an organic layer between the first electrode and the second electrode, the organic layer comprising an emission layer,
   wherein the organic layer further comprises the condensed cyclic compound of claim 1.

17. The organic light-emitting device of claim 16, wherein the first electrode is an anode;
   the second electrode is a cathode;
   the organic layer comprises:
      a hole transport region between the first electrode and the emission layer, the hole transport region comprising at least one selected from a hole injection layer, a hole transport layer, a buffer layer, and an electron blocking layer, and
   an electron transport region between the emission layer and the second electrode, the electron transport region comprising at least one selected from a hole blocking layer, an electron transport layer, and an electron injection layer; and
   at least one selected from the emission layer and the electron transport region comprises the condensed cyclic compound.

18. The organic light-emitting device of claim 17, wherein the electron transport region comprises an electron transport layer, and the electron transport layer comprises the condensed cyclic compound.

19. A condensed cyclic compound being one of Compounds 5, 7 to 11, 16, and 18 to 45:

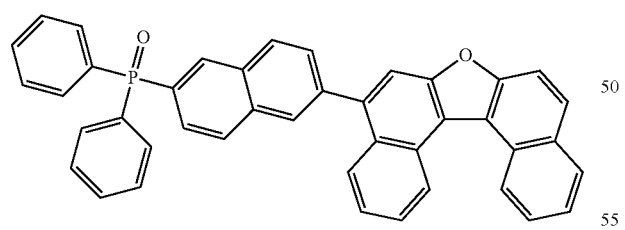
5

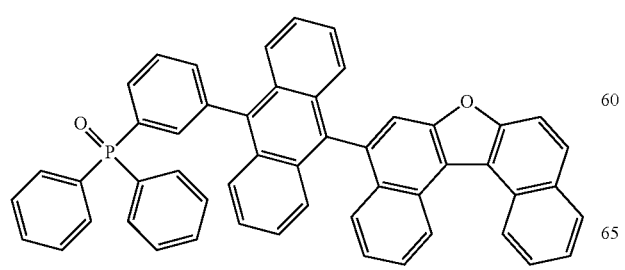
7

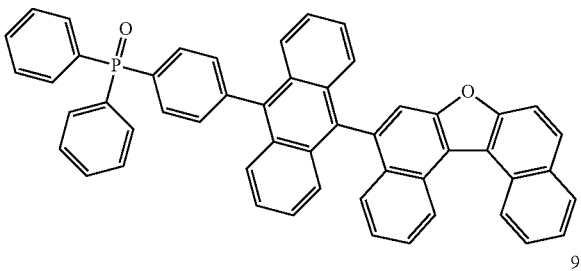
8

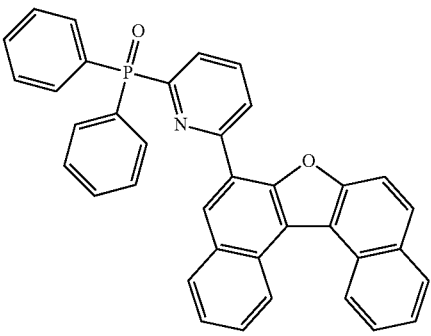
9

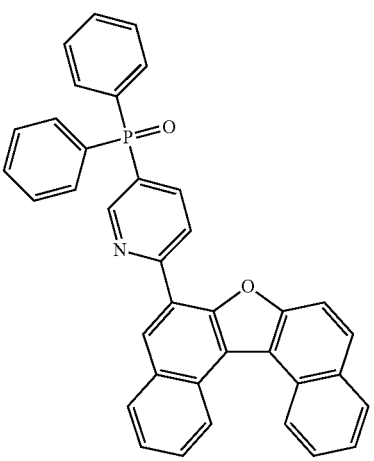
10

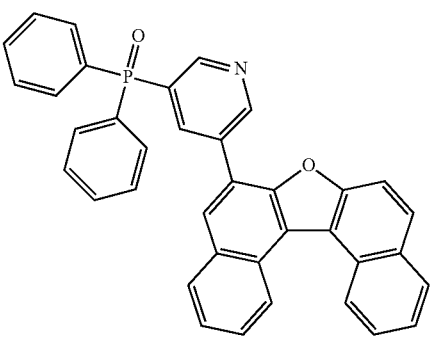
11

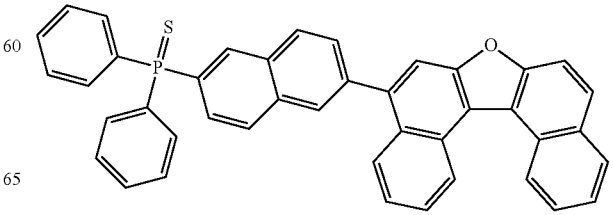
16

211
-continued
18
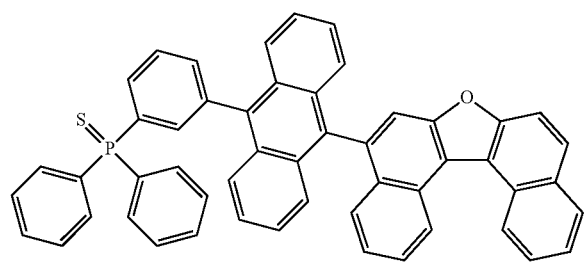
19
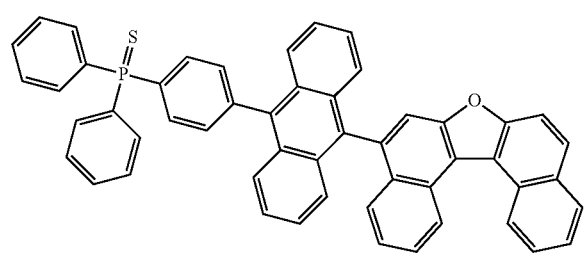
20
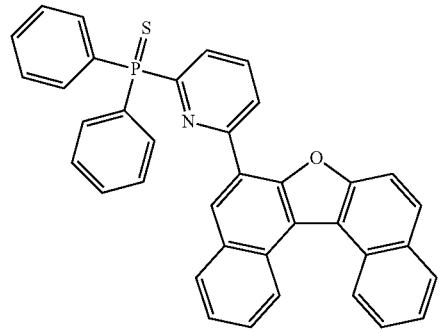
21
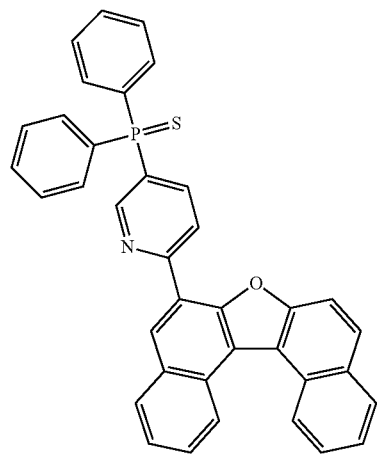
212
-continued
22
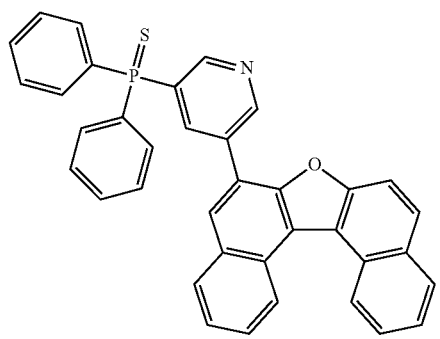
23
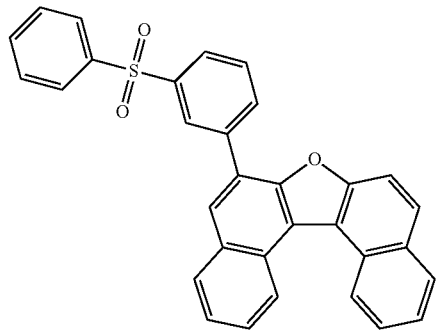
24
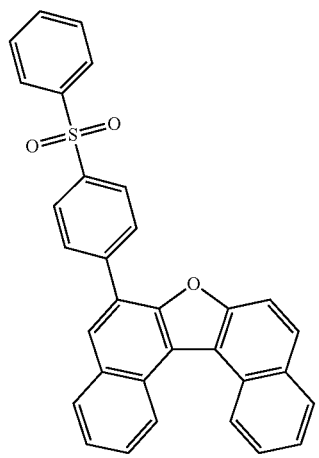
25
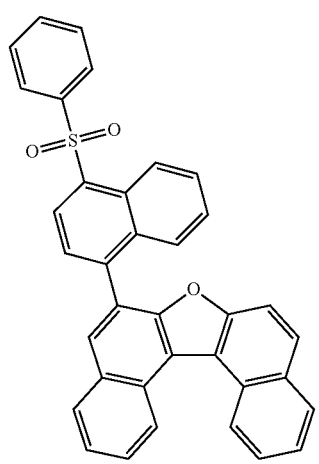

26
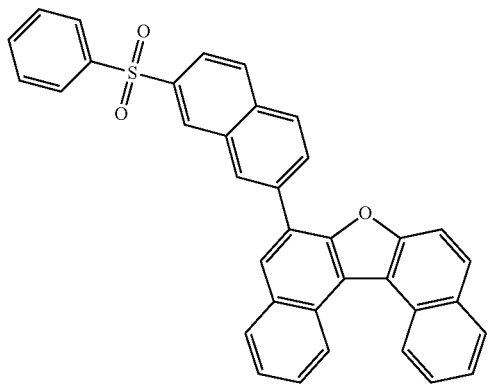
27
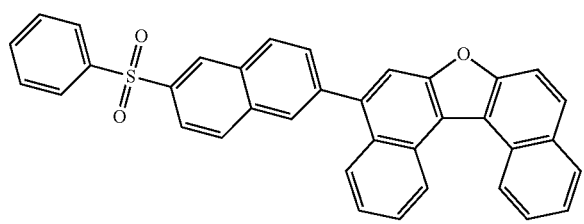
28
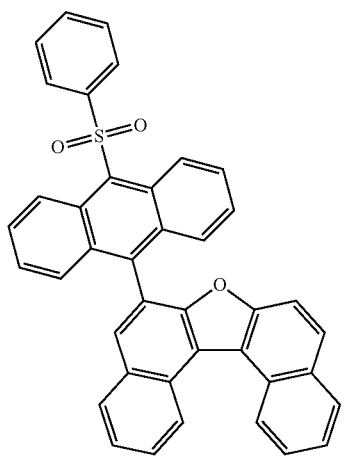
29
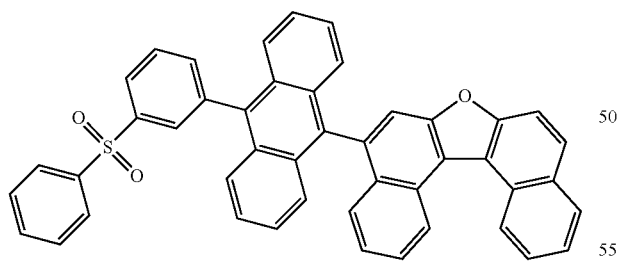
30
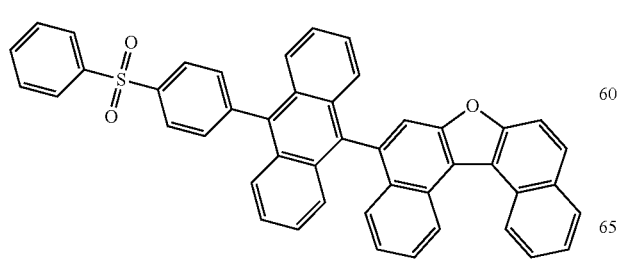
31
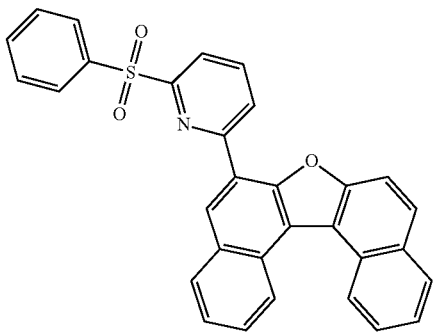
32
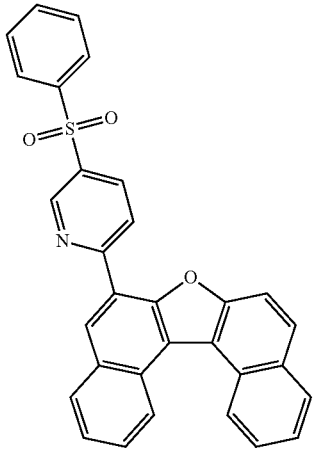
33
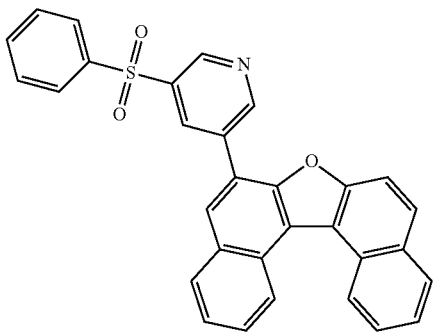
34
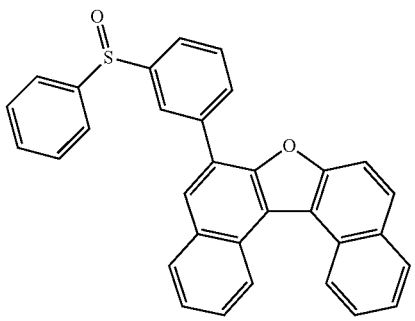

35
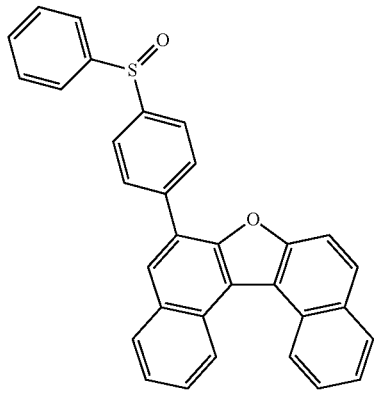
36
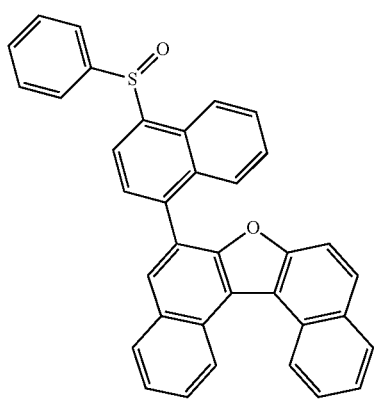
37
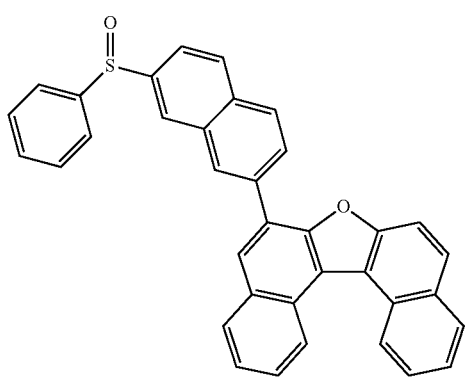
38
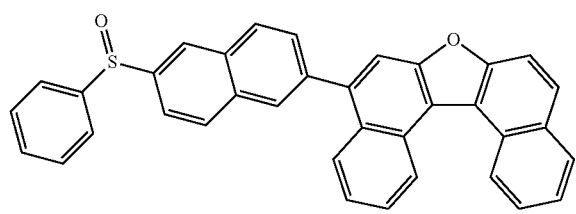
39
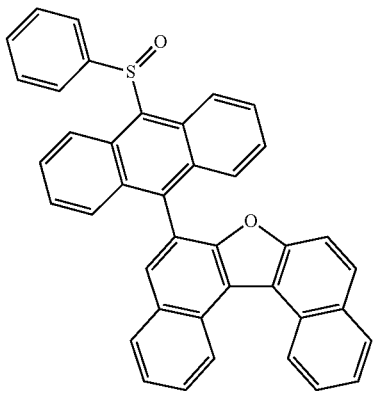
40
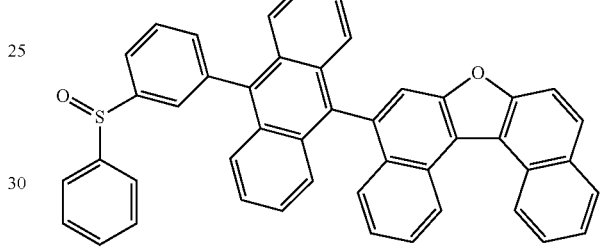
41
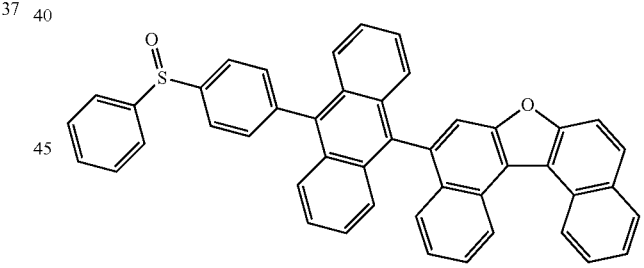
42
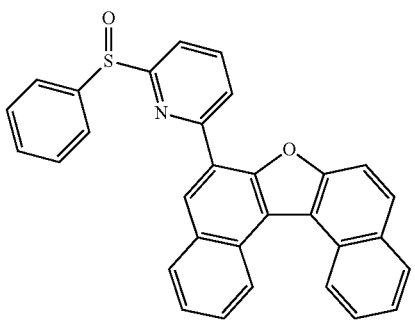

-continued

43

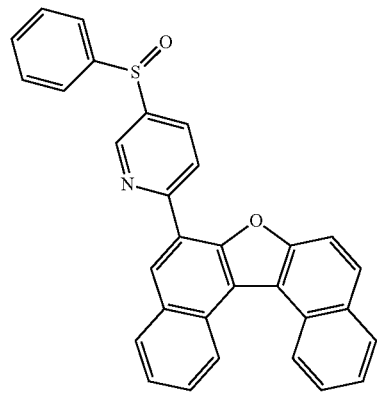

44

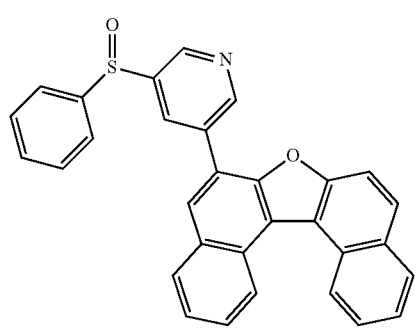

45

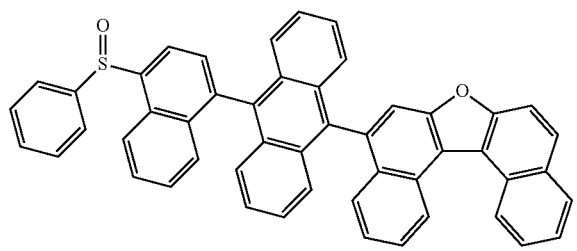

20. An organic light-emitting device comprising:
a first electrode;
a second electrode facing the first electrode; and
an organic layer between the first electrode and the second electrode, the organic layer comprising an emission layer, wherein the emission layer comprises a condensed cyclic compound represented by Formula 1:

$$A_2\text{-}(A_1)_{n1},\qquad \text{Formula 1}$$

wherein, in Formula 1,
$A_2$ is selected from groups represented by Formulae 2A to 2E;
$A_1$ is selected from groups represented by Formulae 2-1 to 2-4; and
n1 is an integer selected from 1 to 5, wherein, when n1 is 2 or greater, at least two $A_1$s are the same as or different from each other:

Formula 2A
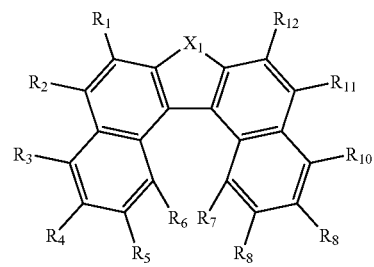

Formula 2B
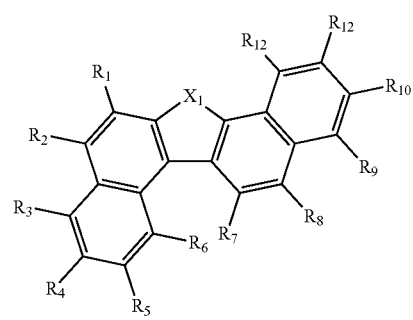

Formula 2C
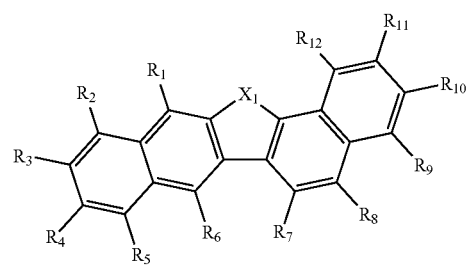

Formula 2D
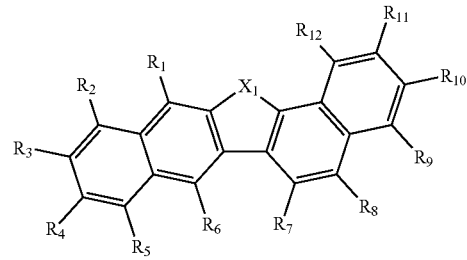

Formula 2E
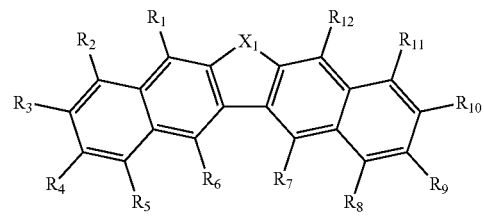

Formula 2-1
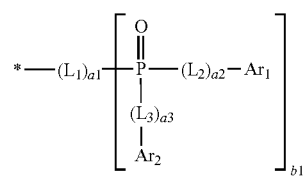

-continued

Formula 2-2

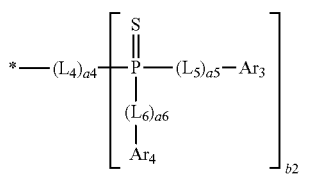

Formula 2-3

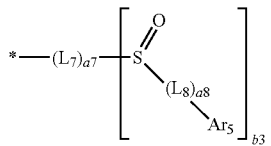

Formula 2-4

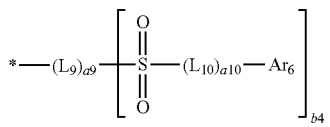

Formula 2-11

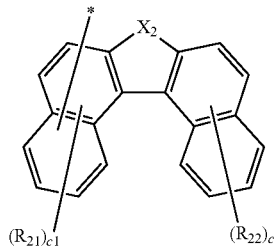

Formula 2-12

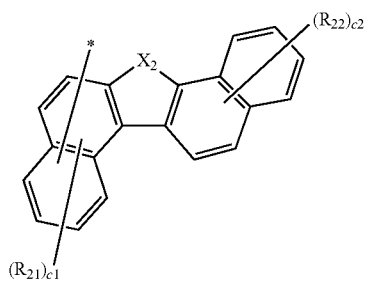

Formula 2-13

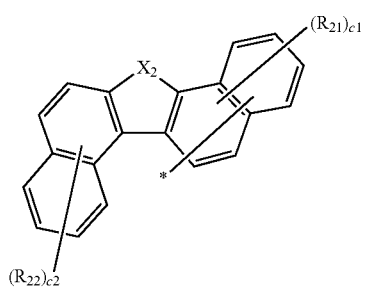

Formula 2-14

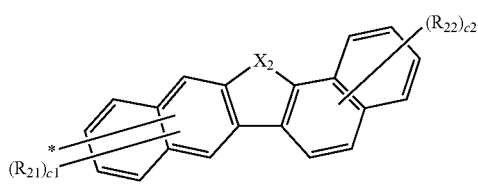

-continued

Formula 2-15

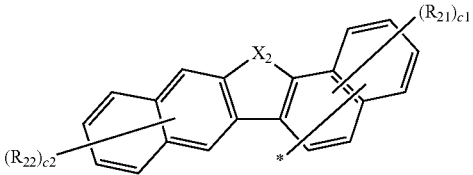

Formula 2-16

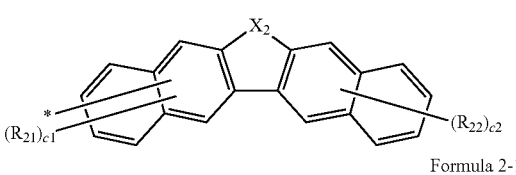

Formula 2-17

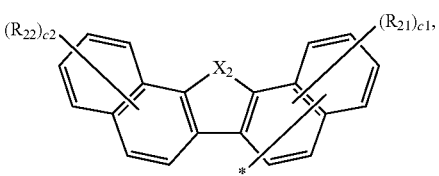

wherein, $X_1$ and $X_2$ in Formulae 2A to 2E and Formulae 2-11 to 2-17 are each independently O or S;

$R_1$ to $R_{12}$ in Formulae 2A to 2E are each independently selected from a binding site to $A_1$ in Formula 1, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), wherein at least one selected from $R_1$ to $R_{12}$ is a binding site to $A_1$ in Formula 1, and a number of binding sites is equal to n1;

$L_1$ to $L_{10}$ in Formulae 2-1 to 2-4 are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a10 in Formulae 2-1 to 2-4 are each independently an integer selected from 0 to 5;

$Ar_1$ to $Ar_6$ in Formulae 2-1 to 2-4 are each independently selected from groups represented by Formulae 2-11 to 2-17, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b1 to b4 in Formulae 2-1 to 2-4 are each independently an integer selected from 1 to 5;

$R_{21}$ and $R_{22}$ in Formulae 2-11 to 2-17 are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

c1 in Formulae 2-11 to 2-17 is an integer selected from 0 to 5; and c2 in Formulae 2-11 to 2-17 is an integer selected from 0 to 6, wherein at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

21. A condensed cyclic compound represented by Formula 2A-1:

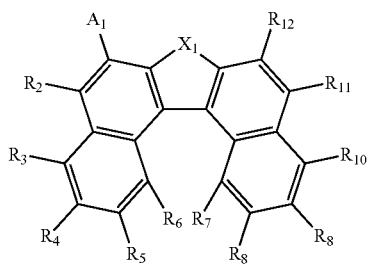

Formula 2A-1

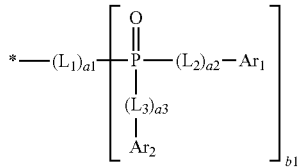

Formula 2-1

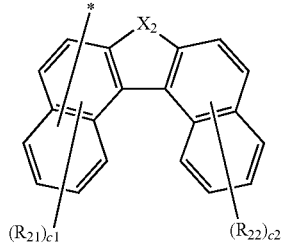

Formula 2-11

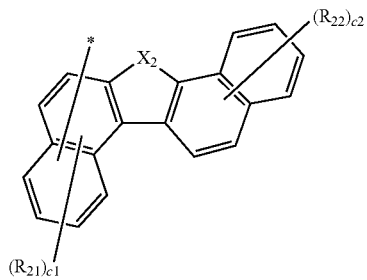

Formula 2-12

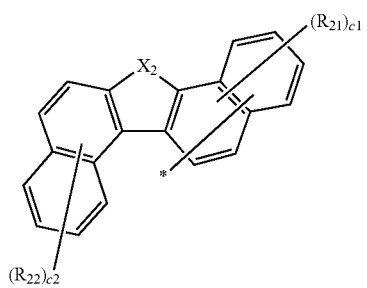

Formula 2-13

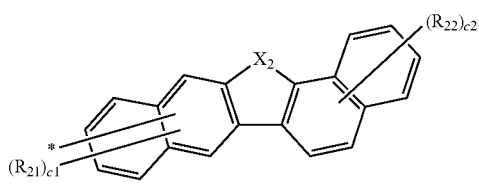

Formula 2-14

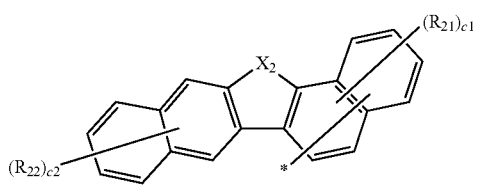

Formula 2-15

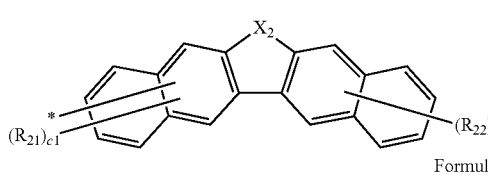

Formula 2-16

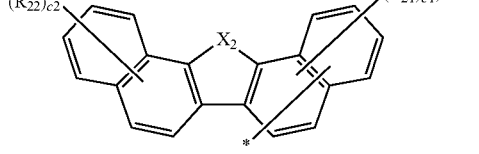

Formula 2-17 wherein
$X_1$ is S or O;
$A_1$ is represented by Formula 2-1;
$L_1$ to $L_3$ are each independently selected from:
a pentalenylene group, an indenylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si$(Q_{33})(Q_{34})(Q_{35})$;

a1 is selected from 1 and 2;

a2 and a3 are each independently selected from 0, 1, and 2;

$R_2$ to $R_{12}$ are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75, and —Si$(Q_3)(Q_4)(Q_5)$;

$Ar_1$ and $Ar_2$ are each independently selected from groups represented by Formulae 2-11 to 2-17 and groups represented by Formulae 5-1 to 5-75;

$R_{21}$ and $R_{22}$ in Formulae 2-11 to 2-17 are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N$(Q_1)(Q_2)$, —Si$(Q_3)(Q_4)(Q_5)$, and —B$(Q_6)(Q_7)$;

c1 in Formulae 2-11 to 2-17 is an integer selected from 0 to 5;

c2 in Formulae 2-11 to 2-17 is an integer selected from 0 to 6; and wherein $Q_3$ to $Q_5$ and $Q_{33}$ to $Q_{35}$ are each independently selected from a $C_1$-$C_{10}$ alkyl group, a $C_1$-$C_{10}$ alkoxy group, a phenyl group, and a naphthyl group:

Formula 5-1

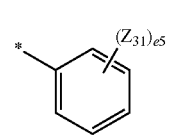

-continued
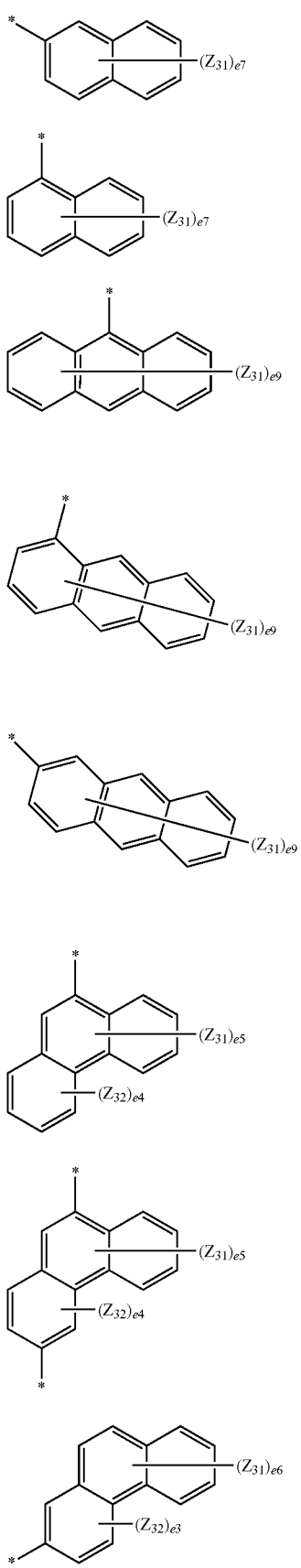
-continued
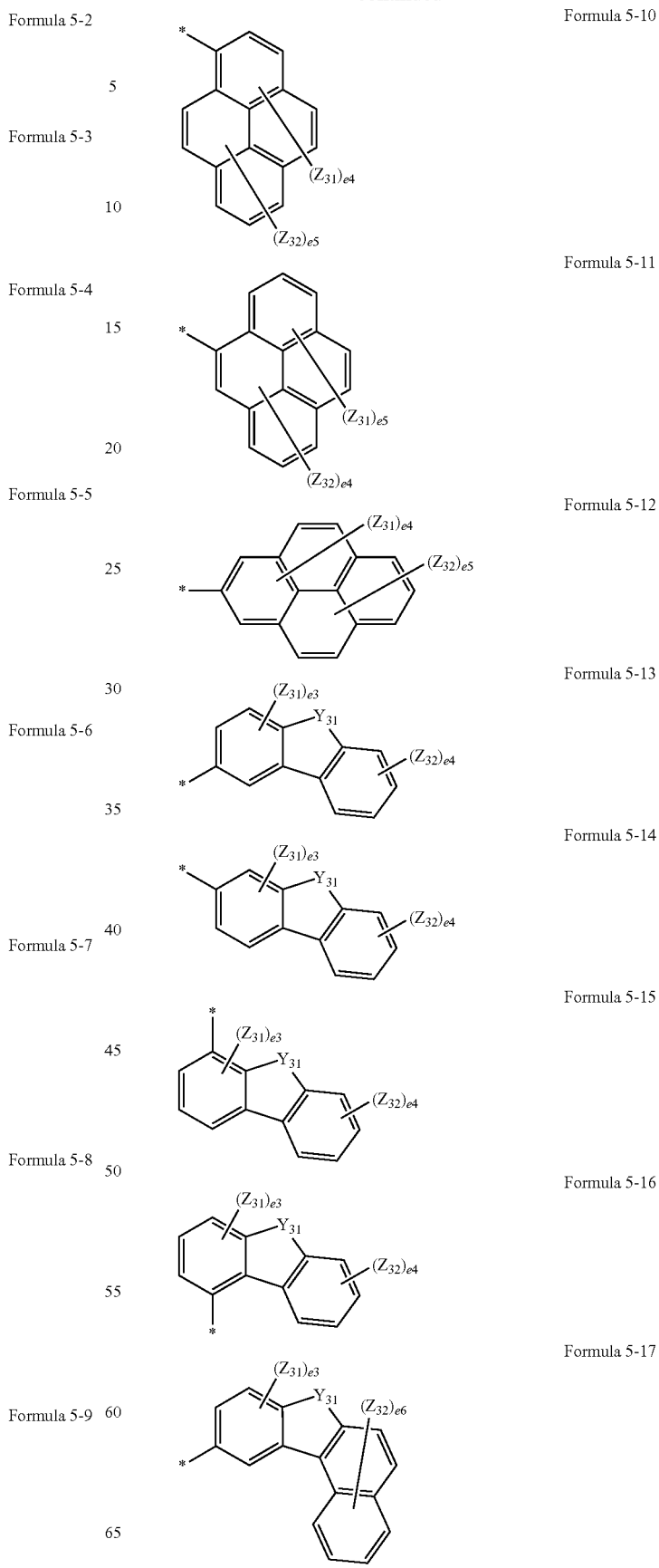

-continued
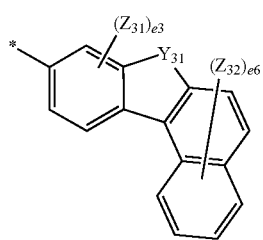
Formula 5-18
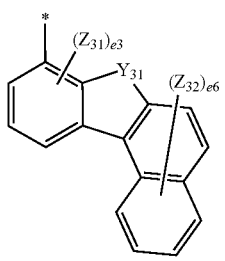
Formula 5-19
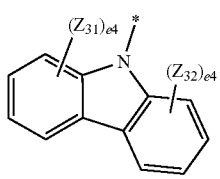
Formula 5-20
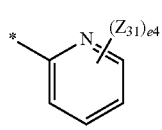
Formula 5-21
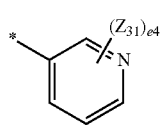
Formula 5-22
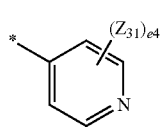
Formula 5-23
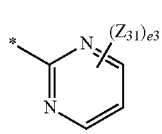
Formula 5-24
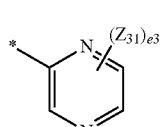
Formula 5-25
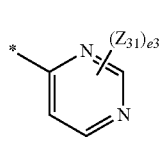
Formula 5-26
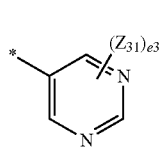
Formula 5-27
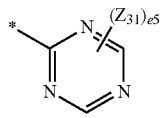
Formula 5-28
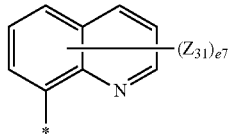
Formula 5-29
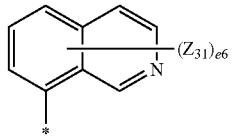
Formula 5-30
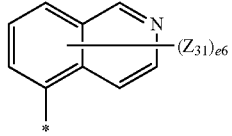
Formula 5-31
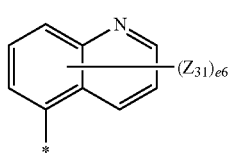
Formula 5-32
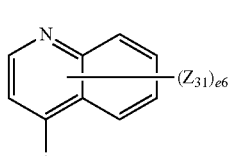
Formula 5-33
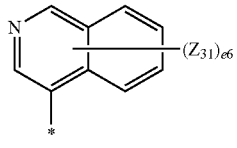
Formula 5-34
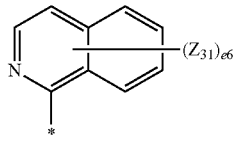
Formula 5-35
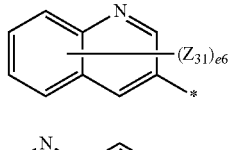
Formula 5-36
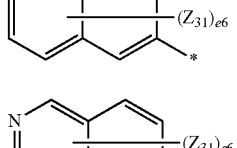
Formula 5-37
Formula 5-38

-continued
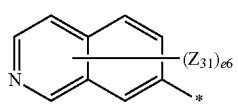 Formula 5-39
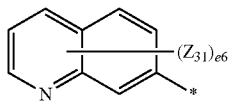 Formula 5-40
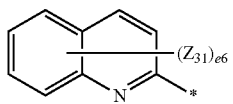 Formula 5-41
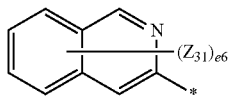 Formula 5-42
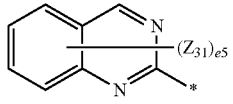 Formula 5-43
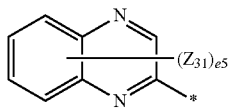 Formula 5-44
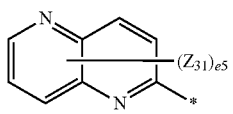 Formula 5-45
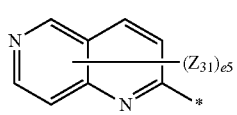 Formula 5-46
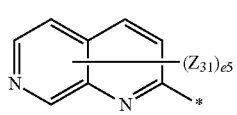 Formula 5-47
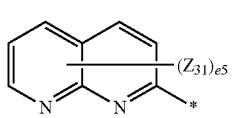 Formula 5-48
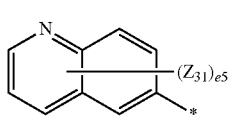 Formula 5-49
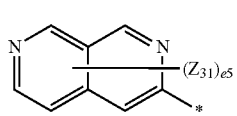 Formula 5-50
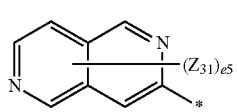 Formula 5-51
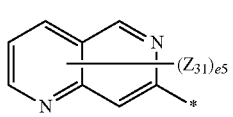 Formula 5-52
-continued
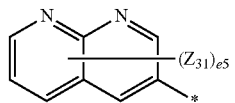 Formula 5-53
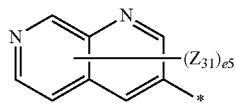 Formula 5-54
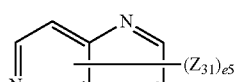 Formula 5-55
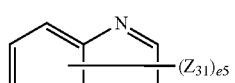 Formula 5-56
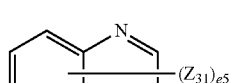 Formula 5-57
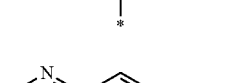 Formula 5-58
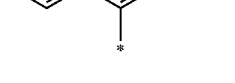 Formula 5-59
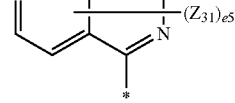 Formula 5-60
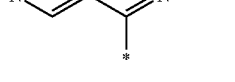 Formula 5-61
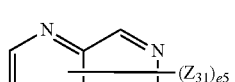 Formula 5-62
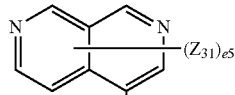 Formula 5-63

Formula 5-64
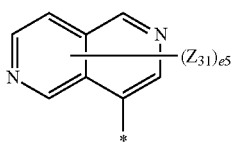

Formula 5-65
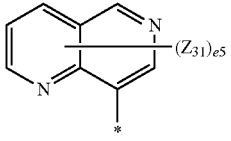

Formula 5-66
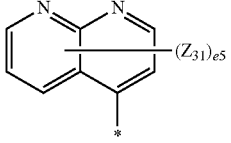

Formula 5-67
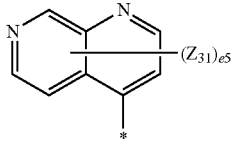

Formula 5-68
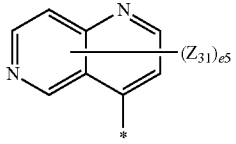

Formula 5-69
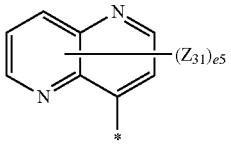

Formula 5-70
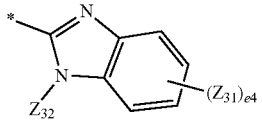

Formula 5-71
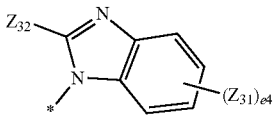

Formula 5-72
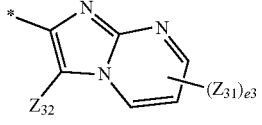

Formula 5-73
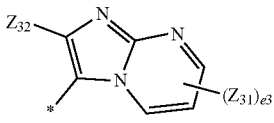

Formula 5-74
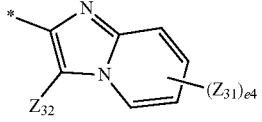

Formula 5-75
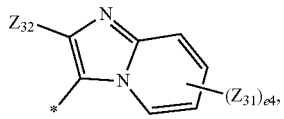

wherein, in Formulae 5-1 to 5-75, $Y_{31}$ is selected from O, S, $C(Z_{33})(Z_{34})$, $N(Z_{35})$, and $Si(Z_{36})(Z_{37})$;

$Z_{31}$ to $Z_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e3 is an integer selected from 1 to 3;
e4 is an integer selected from 1 to 4;
e5 is an integer selected from 1 to 5;
e6 is an integer selected from 1 to 6;
e7 is an integer selected from 1 to 7;
e9 is an integer selected from 1 to 9; and
* is a binding site with an adjacent atom.

22. An organic light-emitting device comprising:
a first electrode;
a second electrode facing the first electrode; and
an organic layer between the first electrode and the second electrode, the organic layer comprising an emission layer,
wherein the organic layer further comprises the condensed cyclic compound of claim 21.

23. A condensed cyclic compound represented by Formula 2A-2:

Formula 2A-2
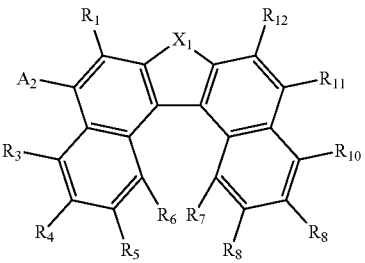

Formula 2-1
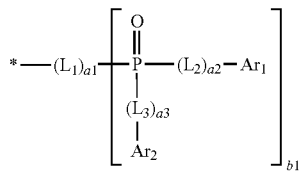

-continued

Formula 2-11
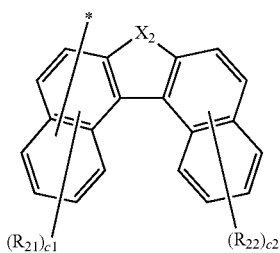

Formula 2-12
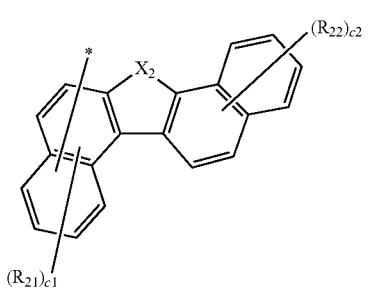

Formula 2-13
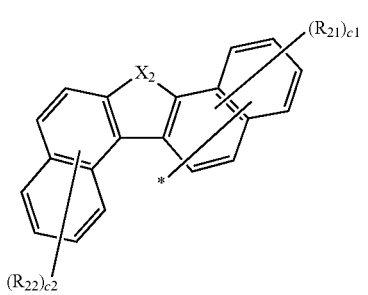

Formula 2-14
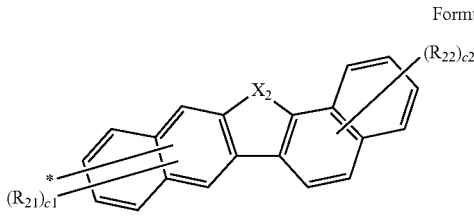

Formula 2-15
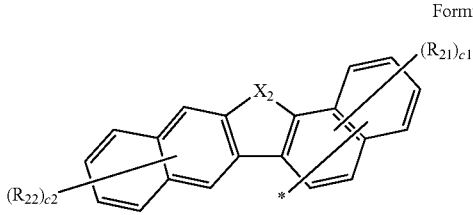

Formula 2-16
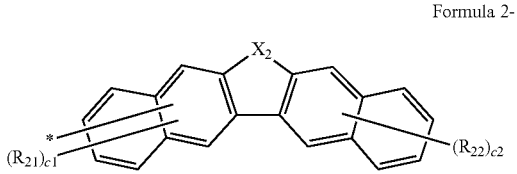

Formula 2-17
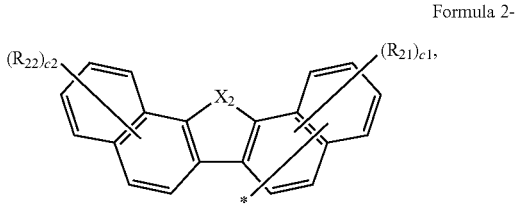

wherein
$X_1$ is S or O;
$A_1$ is represented by Formula 2-1;
$L_1$ to $L_3$ are each independently selected from:
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, and
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$);

a1 is selected from 1 and 2;

a2 and a3 are each independently selected from 0, 1, and 2;

$R_2$ to $R_{12}$ are each independently selected from hydrogen, deuterium, —F, —Cl, —Br, —I, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups represented by Formulae 5-1 to 5-75, and —Si($Q_3$)($Q_4$)($Q_5$);

$Ar_1$ and $Ar_2$ are each independently selected from groups represented by Formulae 2-11 to 2-17, and groups represented by Formulae 5-1 to 5-75;

$R_{21}$ and $R_{22}$ in Formulae 2-11 to 2-17 are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

c1 in Formulae 2-11 to 2-17 is an integer selected from 0 to 5;

c2 in Formulae 2-11 to 2-17 is an integer selected from 0 to 6; and wherein $Q_3$ to $Q_5$ and $Q_{33}$ to $Q_{35}$ are each independently selected from a $C_1$-$C_{10}$ alkyl group, a $C_1$-$C_{10}$ alkoxy group, a phenyl group, and a naphthyl group:

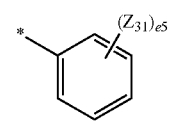

Formula 5-1

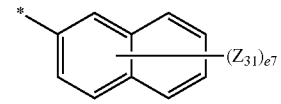

Formula 5-2

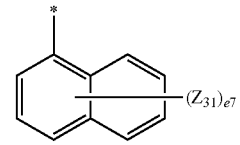

Formula 5-3

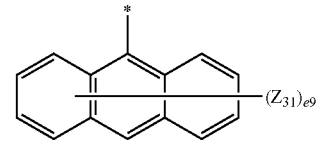

Formula 5-4

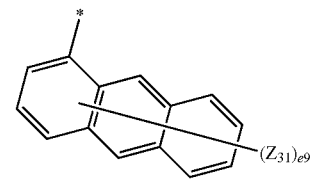

Formula 5-5

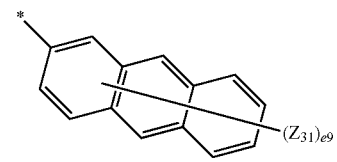

Formula 5-6

-continued
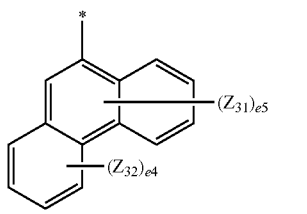
Formula 5-7
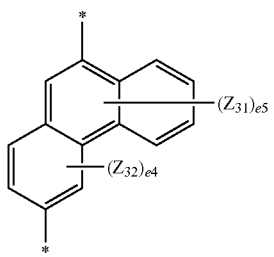
Formula 5-8
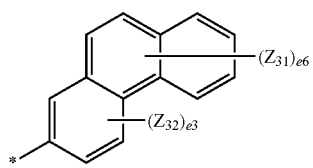
Formula 5-9
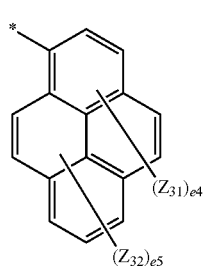
Formula 5-10
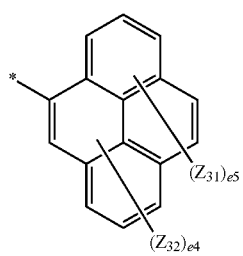
Formula 5-11
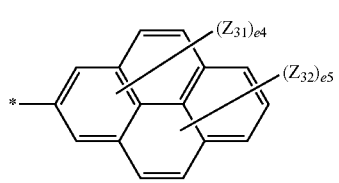
Formula 5-12
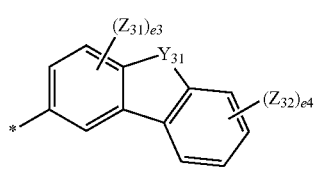
Formula 5-13
-continued
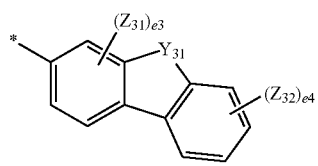
Formula 5-14
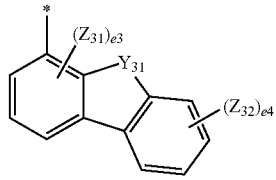
Formula 5-15
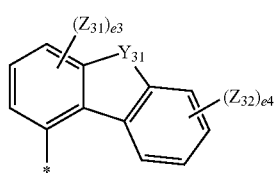
Formula 5-16
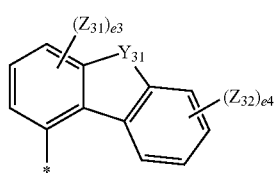
Formula 5-17
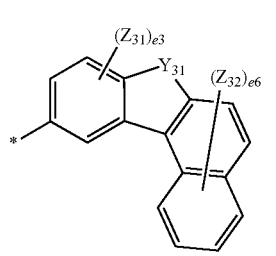
Formula 5-18
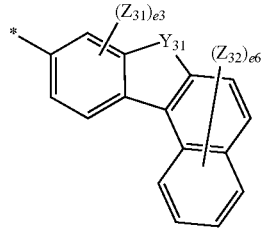
Formula 5-19
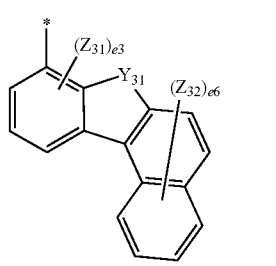
Formula 5-20
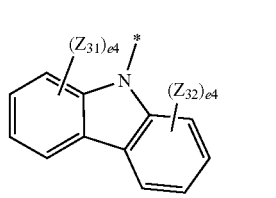
Formula 5-21
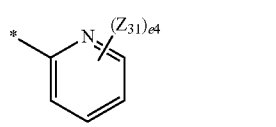

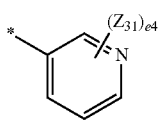
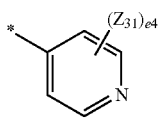
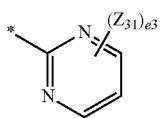
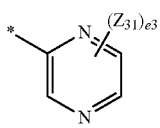
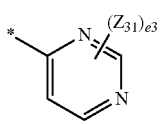
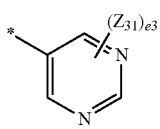
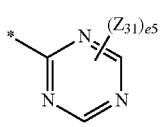
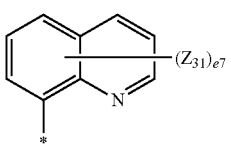
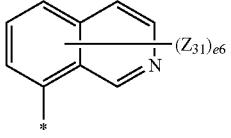
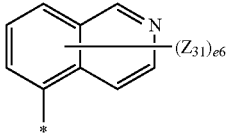
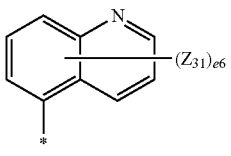
Formula 5-22
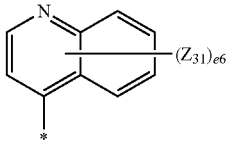
Formula 5-23
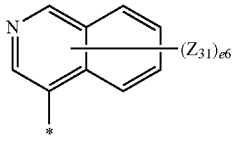
Formula 5-24
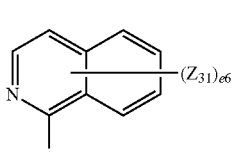
Formula 5-25
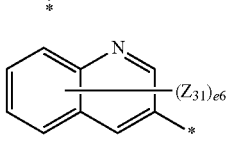
Formula 5-26
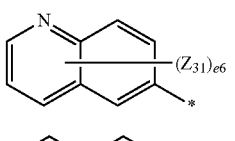
Formula 5-27
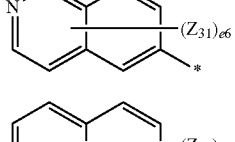
Formula 5-28
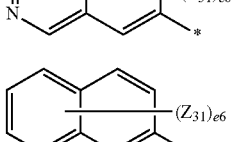
Formula 5-29
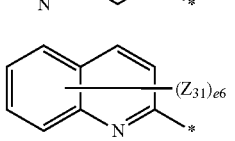
Formula 5-30
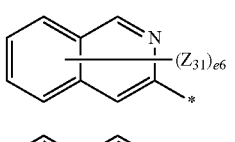
Formula 5-31
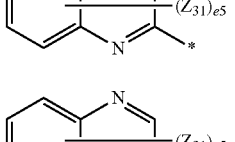
Formula 5-32
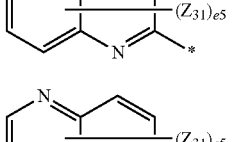
Formula 5-33
Formula 5-34
Formula 5-35
Formula 5-36
Formula 5-37
Formula 5-38
Formula 5-39
Formula 5-40
Formula 5-41
Formula 5-42
Formula 5-43
Formula 5-44
Formula 5-45
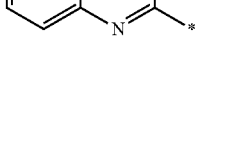

Formula 5-46
Formula 5-47
Formula 5-48
Formula 5-49
Formula 5-50
Formula 5-51
Formula 5-52
Formula 5-53
Formula 5-54
Formula 5-55
Formula 5-56
Formula 5-57
Formula 5-58

Formula 5-59
Formula 5-60
Formula 5-61
Formula 5-62
Formula 5-63
Formula 5-64
Formula 5-65
Formula 5-66
Formula 5-67
Formula 5-68

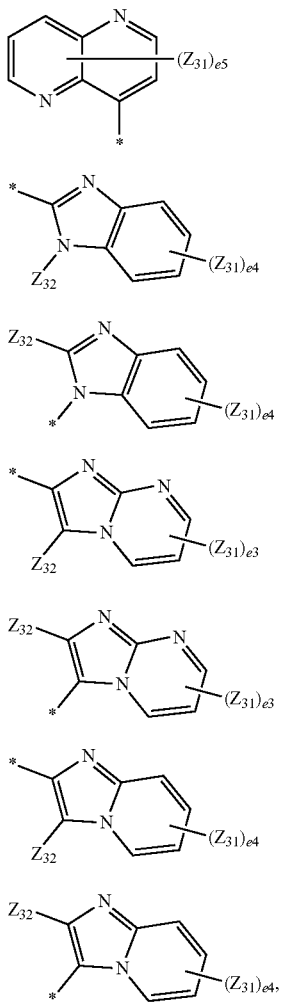

Formula 5-69

Formula 5-70

Formula 5-71

Formula 5-72

Formula 5-73

Formula 5-74

Formula 5-75 wherein, in Formulae 5-1 to 5-75, $Y_{31}$ is selected from O, S, $C(Z_{33})(Z_{34})$, $N(Z_{35})$, and $Si(Z_{36})(Z_{37})$;

$Z_{31}$ to $Z_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e3 is an integer selected from 1 to 3;

e4 is an integer selected from 1 to 4;

e5 is an integer selected from 1 to 5;

e6 is an integer selected from 1 to 6;

e7 is an integer selected from 1 to 7;

e9 is an integer selected from 1 to 9; and

* is a binding site with an adjacent atom.

24. An organic light-emitting device comprising:

a first electrode;

a second electrode facing the first electrode; and an organic layer between the first electrode and the second electrode, the organic layer comprising an emission layer, wherein the organic layer further comprises the condensed cyclic compound of claim 23.

* * * * *